(12) United States Patent
Zion et al.

(10) Patent No.: US 11,667,689 B2
(45) Date of Patent: Jun. 6, 2023

(54) INSULIN-FC FUSION PROTEINS AND METHODS OF USE TO TREAT CANCER

(71) Applicant: Akston Biosciences Corporation, Beverly, MA (US)

(72) Inventors: Todd C. Zion, Salem, MA (US); Thomas M. Lancaster, Wenham, MA (US)

(73) Assignee: Akston Biosciences Corporation, Beverly, MA (US)

( * ) Notice: Subject to any disclaimer, the term of this patent is extended or adjusted under 35 U.S.C. 154(b) by 0 days.

(21) Appl. No.: 17/814,285

(22) Filed: Jul. 22, 2022

(65) Prior Publication Data

US 2023/0072260 A1 Mar. 9, 2023

Related U.S. Application Data

(60) Provisional application No. 63/224,991, filed on Jul. 23, 2021.

(51) Int. Cl.
| | | |
|---|---|---|
| *C07K 14/62* | (2006.01) | |
| *A61P 3/10* | (2006.01) | |
| *A61K 9/00* | (2006.01) | |
| *C07K 14/435* | (2006.01) | |
| *C12N 15/62* | (2006.01) | |

(52) U.S. Cl.
CPC ............ *C07K 14/62* (2013.01); *A61K 9/0019* (2013.01); *A61P 3/10* (2018.01); *C07K 14/435* (2013.01); *C12N 15/62* (2013.01); *C07K 2319/30* (2013.01); *C07K 2319/70* (2013.01)

(58) Field of Classification Search
CPC .......................... C07K 14/62; C07K 2319/30
USPC ...................................................... 435/69.7
See application file for complete search history.

(56) References Cited

U.S. PATENT DOCUMENTS

| | | | |
|---|---|---|---|
| 8,188,231 B2 | 5/2012 | Lazar et al. | |
| 8,933,207 B2 | 1/2015 | Chen et al. | |
| 9,074,015 B2 | 7/2015 | Lancaster et al. | |
| 9,855,318 B2 | 1/2018 | Baldwin et al. | |
| 10,597,435 B2 | 3/2020 | Lancaster et al. | |
| 10,709,766 B2 | 7/2020 | Baldwin et al. | |
| 10,822,386 B2 | 11/2020 | Weiss | |
| 10,851,147 B2 | 12/2020 | Lancaster et al. | |
| 10,870,686 B2 | 12/2020 | Lancaster et al. | |
| 10,894,089 B2 | 1/2021 | Heo et al. | |
| 10,947,292 B2 | 3/2021 | Lancaster et al. | |
| 10,961,294 B2 | 3/2021 | Lancaster et al. | |
| 11,186,623 B2 | 11/2021 | Lancaster et al. | |
| 11,192,930 B2 | 12/2021 | Lancaster et al. | |
| 11,198,719 B2 | 12/2021 | Zion et al. | |
| 11,261,229 B2 | 3/2022 | Lancaster et al. | |
| 11,267,862 B2 | 3/2022 | Lancaster et al. | |
| 11,352,407 B2 | 6/2022 | Lancaster et al. | |
| 11,359,001 B2 | 6/2022 | Lancaster et al. | |
| 2003/0040601 A1 | 2/2003 | Diers et al. | |
| 2012/0093814 A1 | 4/2012 | Canada et al. | |
| 2013/0142795 A1 | 6/2013 | Bai et al. | |
| 2013/0190475 A1 | 7/2013 | Chen et al. | |
| 2013/0190476 A1 | 7/2013 | Lancaster et al. | |
| 2014/0037699 A1 | 2/2014 | Zion et al. | |
| 2014/0302028 A1 | 10/2014 | Zha | |
| 2016/0289290 A1 | 10/2016 | Meehl et al. | |
| 2016/0324932 A1 | 11/2016 | Baldwin et al. | |
| 2018/0009869 A1 | 1/2018 | Lu et al. | |
| 2018/0161448 A1 | 6/2018 | Heo et al. | |
| 2018/0177851 A1 | 6/2018 | Baldwin et al. | |
| 2019/0315828 A1 | 10/2019 | Lancaster et al. | |
| 2019/0382439 A1 | 12/2019 | Kim et al. | |
| 2020/0085925 A1 | 3/2020 | Burkart et al. | |
| 2020/0131243 A1 | 4/2020 | Lancaster et al. | |
| 2020/0140516 A1 | 5/2020 | Weiss | |
| 2020/0140517 A1 | 5/2020 | Weiss | |
| 2020/0157169 A1 | 5/2020 | Lancaster et al. | |
| 2020/0157170 A1 | 5/2020 | Lancaster et al. | |
| 2020/0157171 A1 | 5/2020 | Lancaster et al. | |
| 2020/0231646 A1 | 7/2020 | Lancaster et al. | |
| 2020/0299343 A1 | 9/2020 | Doerner et al. | |
| 2020/0407413 A1 | 12/2020 | Lancaster et al. | |
| 2020/0407414 A1 | 12/2020 | Lancaster et al. | |
| 2022/0009990 A1 | 1/2022 | Lancaster et al. | |
| 2022/0017590 A1 | 1/2022 | Lancaster et al. | |
| 2022/0056098 A1 | 2/2022 | Lancaster et al. | |
| 2022/0064250 A1 | 3/2022 | Lancaster et al. | |
| 2022/0064251 A1 | 3/2022 | Lancaster et al. | |
| 2022/0098266 A1 | 3/2022 | Zion et al. | |

FOREIGN PATENT DOCUMENTS

| | | |
|---|---|---|
| CN | 101891823 | 11/2010 |
| CN | 103509118 | 1/2014 |
| EP | 3303380 | 4/2018 |
| EP | 3517544 | 7/2019 |
| EP | 2963056 | 11/2019 |
| EP | 3656792 | 5/2020 |

(Continued)

OTHER PUBLICATIONS

Pollak, M., Nature Reviews Cancer, 12: 159-169, 2012.*
Burtrum et al., Cancer Research 63: 8912-8921, (2003).*
Heiden et al. Nature Reviews(Drug discovery) 10: 671-684, (2011).*
Sahra et al., Mol. Cancer Ther. 9: 1092-1099, (2010).*
Alleva, et al., "Immunological characterization and therapeutic activity of an altered-peptide ligand, NBI-6024, based on the immunodominant type 1 diabetes autoantigen insulin B-chain (9-23) peptide", Diabetes, 2002, 51(7) pp. 2126-2134.
Baeshen, et al., "Cell factories for insulin production", Microbial Cell Factories, 2014,13(141).
Brüggemann, et al., "The immunogenicity of chimeric antibodies", Journal of Experimental Medicine, 1989, 170(6) pp. 2153-2157.
Hua, et al., "Design of an Active Ultrastable Single-chain Insulin Analog", Journal of Biological Chemistry, 2008, 283 (21) pp. 14703-14716.

(Continued)

*Primary Examiner* — Gyan Chandra
(74) *Attorney, Agent, or Firm* — Hovey Williams LLP

(57) ABSTRACT

The present disclosure relates to compositions of fusion proteins, e.g., insulin-Fc fusion proteins, and their use to treat cancer cells and cancer tumors.

13 Claims, 8 Drawing Sheets

Specification includes a Sequence Listing.

(56) References Cited

FOREIGN PATENT DOCUMENTS

| | | |
|---|---|---|
| WO | 2010117760 | 10/2010 |
| WO | 2016044676 | 3/2016 |
| WO | 2016119023 | 8/2016 |
| WO | 2016177771 | 11/2016 |
| WO | 2016178905 | 11/2016 |
| WO | 2018009921 | 1/2018 |
| WO | 2018073185 | 4/2018 |
| WO | 2018107117 | 6/2018 |
| WO | 2019035010 | 2/2019 |
| WO | 2019204206 | 10/2019 |
| WO | 2020006529 | 1/2020 |
| WO | 2020070276 | 4/2020 |
| WO | 2020106748 | 5/2020 |
| WO | 2020236762 | 11/2020 |
| WO | 2021011827 | 1/2021 |
| WO | 2021022149 | 2/2021 |

OTHER PUBLICATIONS

Strietzel, et al., "In Vitro functional characterization of feline IgGs", Veterinary Immunology and Immunopathology, 2014, 158(3-4) pp. 214-223 (abstract attached).

Tang, et al., "Cloning and characterization of cDNAs encoding four different canine immunoglobulin γ chains", Veterinary Immunology and Immunopathology, 2001, 80(3-4) pp. 259-270 (abstract attached).

Terada, et al., "A chimeric human-cat Fcγ-Fel d1 fusion protein inhibits systemic, pulmonary, and cutaneous allergic reactivity to intratracheal challenge in mice sensitized to Fel d1, the major cat allergen", Clinical Immunology, 2006, 120(1) pp. 45-56 (abstract attached).

Wang, et al., "Proinsulin-Transferrin Fusion Protein as a Novel Long-Acting Insulin Analog for the Inhibition of Hepatic Glucose Production", Diabetes, 2014, 63 pp. 1779-1788.

Yourgenome.org, "What does DNA do?", 2016, https://www.yourgenome.org/facts/what-does-dna-do.

Wang, et al., "IgG Fc engineering to modulate antibody effector functions", Protein Cell, Jan. 2018, 9(1), pp. 63-73.

Kim, et al., "Mammalian cell transfection: the present and the future", Analytical and Bioanalytical Chemistry, 2010, 397(8), pp. 3173-3178.

Fan, et al., "Improving the efficiency of CHO cell line generation using glutamine synthetase gene knockout cells", Biotechnology and Bioengineering, 2012, 109(4), pp. 1007-1015 (abstract attached).

Lodish, et al., Molecular Cell Biology, Molecular Cell Biology, 4th edition, 2000, www.ncbi.nlm.gov/books/NBK21654 (abstract attached).

Horvath, et al., "An automated DNA synthesizer employing deoxynucleoside 3'-phosphoramidites", Methods in Enzymology, Academic Press, 1987, 154, pp. 314-326 (abstract attached).

Dumont, et al., "Human cell lines for biopharmaceutical manufacturing: history, status, and future perspectives", Critical Reviews in Biotechnology, 2016, 36(6), pp. 1110-1122.

Singh, et al., "Combined blockade of HER2 and VEGF exerts greater growth inhibition of HER2-overexpressing gastric cancer xenografts than individual blockade", Experimental and Molecular Medicine, 2013, 45, 11 pages.

Huang, et al., "Production of recombinant murine-human chimeric IgM and IgG anti-Jsb for use in the clinical laboratory", Transfusion, 2003, 43(6), pp. 758-764 (abstract attached).

International Search Report and Written Opinion in corresponding PCT/US2022/74036, dated Jan. 5, 2023.

\* cited by examiner

```
SEQ ID NO: 2  atggaatggagctgggtctttctcttcttcctgtcagtaacgactggtgtccactccttc
SEQ ID NO: 1   M  E  W  S  W  V  F  L  F  F  L  S  V  T  T  G  V  H  S  F
              gtgaaccagcacctgtgcggctccgacctggtggaagctctggctctcgtgtgcggcgag
               V  N  Q  H  L  C  G  S  D  L  V  E  A  L  A  L  V  C  G  E
              cggggcttcttctacaccgatccactggaggccgtccacgcagaggcatcgtggaacag
               R  G  F  F  Y  T  D  P  T  G  G  P  R  R  G  I  V  E  Q
              tgctgccactccatctgctccctgtaccagctggaaaactactgcaatggcggaggtggt
               C  C  H  S  I  C  S  L  Y  Q  L  E  N  Y  C  N  G  G  G
              gcaggaggcggtggagacaaaactcacacatgccacccgtcccagcacctgaactcctg
               A  G  G  G  D  K  T  H  T  C  P  P  C  P  A  P  E  L  L
              gggggaccgtcagtcttcctcttccccccaaaacccaaggacacccttcatgatctcccgg
               G  G  P  S  V  F  L  F  P  P  K  P  K  D  T  L  M  I  S  R
              acccctgaggtcacatgcgtggtggtggacgtgagccacgaagaccctgaggtcaagttc
               T  P  E  V  T  C  V  V  V  D  V  S  H  E  D  P  E  V  K  F
              aactggtacgtggacggcgtggaggtgcataatgccaagacaaagccgcgggaggagcag
               N  W  Y  V  D  G  V  E  V  H  N  A  K  T  K  P  R  E  Q
              tacaacagcacgtaccgtgtggtcagcgtcctcaccgtcctgcaccaggactggctgaat
               Y  N  S  T  Y  R  V  V  S  V  L  T  V  L  H  Q  D  W  L  N
              ggcaaggagtacaagtgcaaggtctccaacaaagccctcccagcccccatcgagaaaacc
               G  K  E  Y  K  C  K  V  S  N  K  A  L  P  A  P  I  E  K  T
              atctccaaagccaaagggcagccccgagaaccacaggtgtacaccctgcccccatcccgg
               I  S  K  A  K  G  Q  P  R  E  P  Q  V  Y  T  L  P  P  S  R
              gatgagctgaccaagaaccaggtcagcctgacctgcctggtcaaaggcttctatcccagc
               D  E  L  T  K  N  Q  V  S  L  T  C  L  V  K  G  F  Y  P  S
              gacatcgccgtggagtgggagagcaatgggcagccggagaacaactacaagaccacgcct
               D  I  A  V  E  W  E  S  N  G  Q  P  E  N  N  Y  K  T  T  P
              cccgtgctggactccgacggctccttcttcctctacagcaagctcaccgtggacaagagc
               P  V  L  D  S  D  G  S  F  F  L  Y  S  K  L  T  V  D  K  S
              aggtggcagcaggggaacgtcttctcatgctccgtgatgcatgaggctctgcacaaccac
               R  W  Q  Q  G  N  V  F  S  C  S  V  M  H  E  A  L  H  N  H
              tacacgcagaagagcctctccctgtctccgggttag
               Y  T  Q  K  S  L  S  L  S  P  G  -
```

FIG. 2

SEQ ID NO: 4　atggaatggagctgggtctttctcttcttcctgtcagtaacgactggtgtccactccttc
SEQ ID NO: 3　 M   E   W   S   W   V   F   L   F   F   L   S   V   T   T   G   V   H   S   F
　　　　　　　gtgaaccagcacctgtgcggctcccacctggtggaagctctggaactcgtgtgcggcgag
　　　　　　　 V   N   Q   H   L   C   G   S   H   L   V   E   A   L   E   L   V   C   G   E
　　　　　　　cggggcttccactacgggggtggcggaggaggttctggtggcggcggaggcatcgtggaa
　　　　　　　 R   G   F   H   Y   G   G   G   G   S   G   G   G   G   I   V   E
　　　　　　　cagtgctgcacctccacctgctccctggaccagctggaaaactactgcggtggcggaggt
　　　　　　　 Q   C   C   T   S   T   C   S   L   D   Q   L   E   N   Y   C   G   G   G
　　　　　　　ggtcaaggaggcggtggacagggtggaggtgggcagggaggaggcggggagacaaaact
　　　　　　　 G   Q   G   G   G   Q   G   G   G   Q   G   G   G   S   D   K   T
　　　　　　　cacacatgcccaccgtgcccagcacctgaactcctggggggaccgtcagtcttcctcttc
　　　　　　　 H   T   C   P   P   C   P   A   P   E   L   L   G   P   S   V   F   L   F
　　　　　　　cccccaaaacccaaggacaccctcatgatctcccggacccctgaggtcacatgcgtggtg
　　　　　　　 P   P   K   P   K   D   T   L   M   I   S   R   T   P   E   V   T   C   V   V
　　　　　　　gtggacgtgagccacgaagaccctgaggtcaagttcaactggtacgtggacggcgtggag
　　　　　　　 V   D   V   S   H   E   D   P   E   V   K   F   N   W   Y   V   D   G   V   E
　　　　　　　gtgcataatgccaagacaaagccgcgggaggagcagtacaacagcacgtaccgtgtggtc
　　　　　　　 V   H   N   A   K   T   K   P   R   E   E   Q   Y   N   S   T   Y   R   V   V
　　　　　　　agcgtcctcaccgtcctgcaccaggactggctgaatggcaaggagtacaagtgcaaggtc
　　　　　　　 S   V   L   T   V   L   H   Q   D   W   L   N   G   K   E   Y   K   C   K   V
　　　　　　　tccaacaaagccctcccagcccccatcgagaaaaccatctccaaagccaaagggcagccc
　　　　　　　 S   N   K   A   L   P   A   P   I   E   K   T   I   S   K   A   K   G   Q   P
　　　　　　　cgagaaccacaggtgtacaccctgcccccatcccgggatgagctgaccaagaaccaggtc
　　　　　　　 R   E   P   Q   V   Y   T   L   P   P   S   R   D   E   L   T   K   N   Q   V
　　　　　　　agcctgacctgcctggtcaaaggcttctatccagcgacatcgccgtggagtgggagagc
　　　　　　　 S   L   T   C   L   V   K   G   F   Y   P   S   D   I   A   V   E   W   E   S
　　　　　　　aatgggcagccggagaacaactacaagaccacgcctcccgtgctggactccgacggctcc
　　　　　　　 N   G   Q   P   E   N   N   Y   K   T   T   P   P   V   L   D   S   D   G   S
　　　　　　　ttcttcctctacagcaagctcaccgtggacaagagcaggtggcagcaggggaacgtcttc
　　　　　　　 F   F   L   Y   S   K   L   T   V   D   K   S   R   W   Q   Q   G   N   V   F
　　　　　　　tcatgctccgtgatgcatgaggctctgcacaaccactacacgcagaagagcctctccctg
　　　　　　　 S   C   S   V   M   H   E   A   L   H   N   H   Y   T   Q   K   S   L   S   L
　　　　　　　tctccgggttag
　　　　　　　 S   P   G   -

FIG. 3

```
SEQ ID NO:3     FVNQHLCGSHLVEALELVCGERGFHYGGGGGSGGGGGIVEQCCTSTCSLDQLENYCGGG    60
SEQ ID NO:28    FVNQHLCGSHLVEALALVCGERGFFYT-PKGG-GPRRGIVEQCCYSICSLYQLENYCNGG  58
SEQ ID NO:24    FVNQHLCGSDLVEALALVCGERGFFYTDPTGG-GPRRGIVEQCCHSICSLYQLENYCN--  57
SEQ ID NO:22    FVNQHLCGSDLVEALALVCGERGFFYTDPTGG-GPRRGIVEQCCHSICSLYQLENYCNGG  59
SEQ ID NO:20    FVNQHLCGSDLVEALALVCGERGFFYTDPTGG-GPRRGIVEQCCHSICSLYQLENYCGG-  58
SEQ ID NO:18    FVNQHLCGSDLVEALALVCGERGFFYTDPTGG-GPRRGIVEQCCHSICSLYQLENYCNGG  59
SEQ ID NO:1     FVNQHLCGSDLVEALALVCGERGFFYTDPTGG-GPRRGIVEQCCHSICSLYQLENYCNGG  59
SEQ ID NO:26    FVNQHLCGSHLVEALALVCGERGFFYTDPTGG-GPRRGIVEQCCHSICSLYQLENYCNGG  59
                ********* ***** ******** *       ** *  ******* * *** ******.

SEQ ID NO:3     GGQGGGKQGGGGQGGGGKDKTHTCPPCPAPELLGGPSVFLFPPKPKDTLMISRTPEVTCV  120
SEQ ID NO:28    GGAG-----------GGGGDKTHTCPPCPAPELLGGPSVFLFPPKPKDTLMISRTPEVTCV  107
SEQ ID NO:24    ------------------DKTHTCPPCPAPELLGGPSVFLFPPKPKDTLMISRTPEVTCV  99
SEQ ID NO:22    ----------------GGGDKTHTCPPCPAPELLGGPSVFLFPPKPKDTLMISRTPEVTCV  103
SEQ ID NO:20    -----GGA------GGGGDKTHTCPPCPAPELLGGPSVFLFPPKPKDTLMISRTPEVTCV  107
SEQ ID NO:18    GGAGGGGA------GGGGDKTHTCPPCPAPELLGGPSVFLFPPKPKDTLMISRTPEVTCV  113
SEQ ID NO:1     GGA-----------GGGGDKTHTCPPCPAPELLGGPSVFLFPPKPKDTLMISRTPEVTCV  108
SEQ ID NO:26    GGA-----------GGGGDKTHTCPPCPAPELLGGPSVFLFPPKPKDTLMISRTPEVTCV  108
                                  ******************************************

SEQ ID NO:3     VVDVSHEDPEVKFNWYVDGVEVHNAKTKPREEQYNSTYRVVSVLTVLHQDWLNGKEYKCK  180
SEQ ID NO:28    VVDVSHEDPEVKFNWYVDGVEVHNAKTKPREEQYNSTYRVVSVLTVLHQDWLNGKEYKCK  167
SEQ ID NO:24    VVDVSHEDPEVKFNWYVDGVEVHNAKTKPREEQYNSTYRVVSVLTVLHQDWLNGKEYKCK  159
SEQ ID NO:22    VVDVSHEDPEVKFNWYVDGVEVHNAKTKPREEQYNSTYRVVSVLTVLHQDWLNGKEYKCK  163
SEQ ID NO:20    VVDVSHEDPEVKFNWYVDGVEVHNAKTKPREEQYNSTYRVVSVLTVLHQDWLNGKEYKCK  167
SEQ ID NO:18    VVDVSHEDPEVKFNWYVDGVEVHNAKTKPREEQYNSTYRVVSVLTVLHQDWLNGKEYKCK  173
SEQ ID NO:1     VVDVSHEDPEVKFNWYVDGVEVHNAKTKPREEQYNSTYRVVSVLTVLHQDWLNGKEYKCK  168
SEQ ID NO:26    VVDVSHEDPEVKFNWYVDGVEVHNAKTKPREEQYNSTYRVVSVLTVLHQDWLNGKEYKCK  168
                ************************************************************

SEQ ID NO:3     VSNKALPAPIEKTISKAKGQPREPQVYTLPPSRDELTKNQVSLTCLVKGFYPSDIAVEWE  240
SEQ ID NO:28    VSNKALPAPIEKTISKAKGQPREPQVYTLPPSRDELTKNQVSLTCLVKGFYPSDIAVEWE  227
SEQ ID NO:24    VSNKALPAPIEKTISKAKGQPREPQVYTLPPSRDELTKNQVSLTCLVKGFYPSDIAVEWE  219
SEQ ID NO:22    VSNKALPAPIEKTISKAKGQPREPQVYTLPPSRDELTKNQVSLTCLVKGFYPSDIAVEWE  223
SEQ ID NO:20    VSNKALPAPIEKTISKAKGQPREPQVYTLPPSRDELTKNQVSLTCLVKGFYPSDIAVEWE  227
SEQ ID NO:18    VSNKALPAPIEKTISKAKGQPREPQVYTLPPSRDELTKNQVSLTCLVKGFYPSDIAVEWE  233
SEQ ID NO:1     VSNKALPAPIEKTISKAKGQPREPQVYTLPPSRDELTKNQVSLTCLVKGFYPSDIAVEWE  228
SEQ ID NO:26    VSNKALPAPIEKTISKAKGQPREPQVYTLPPSRDELTKNQVSLTCLVKGFYPSDIAVEWE  228
                ************************************************************

SEQ ID NO:3     SNGQPENNYKTTPPVLDSDGSFFLYSKLTVDKSRWQQGNVFSCSVMHEALHNHYTQKSLS  300
SEQ ID NO:28    SNGQPENNYKTTPPVLDSDGSFFLYSKLTVDKSRWQQGNVFSCSVMHEALHNHYTQKSLS  287
SEQ ID NO:24    SNGQPENNYKTTPPVLDSDGSFFLYSKLTVDKSRWQQGNVFSCSVMHEALHNHYTQKSLS  279
SEQ ID NO:22    SNGQPENNYKTTPPVLDSDGSFFLYSKLTVDKSRWQQGNVFSCSVMHEALHNHYTQKSLS  283
SEQ ID NO:20    SNGQPENNYKTTPPVLDSDGSFFLYSKLTVDKSRWQQGNVFSCSVMHEALHNHYTQKSLS  287
SEQ ID NO:18    SNGQPENNYKTTPPVLDSDGSFFLYSKLTVDKSRWQQGNVFSCSVMHEALHNHYTQKSLS  293
SEQ ID NO:1     SNGQPENNYKTTPPVLDSDGSFFLYSKLTVDKSRWQQGNVFSCSVMHEALHNHYTQKSLS  288
SEQ ID NO:26    SNGQPENNYKTTPPVLDSDGSFFLYSKLTVDKSRWQQGNVFSCSVMHEALHNHYTQKSLS  288
                ************************************************************

SEQ ID NO:3     LSPG 304
SEQ ID NO:28    LSPG 291
SEQ ID NO:24    LSPG 283
SEQ ID NO:22    LSPG 287
SEQ ID NO:20    LSPG 291
SEQ ID NO:18    LSPG 297
SEQ ID NO:1     LSPG 292
SEQ ID NO:26    LSPG 292
                ****
```

FIG. 4

INSULIN-FC FUSION PROTEINS AND METHODS OF USE TO TREAT CANCER

CROSS-REFERENCE TO RELATED APPLICATIONS

The present application is related to and claims the priority benefit of U.S. Provisional Patent Application Ser. No. 63/224,991, filed Jul. 23, 2021. The contents of the aforementioned patent application are hereby incorporated herein by reference in their entirety.

SEQUENCE LISTING

The following application contains a sequence listing submitted electronically as a Standard ST.26 compliant XML file entitled "ABC-032-1US.xml," created on Jul. 22, 2022, as 46,809 bytes in size, the contents of which are incorporated herein.

TECHNICAL FIELD

The present disclosure relates to compositions of insulin-Fc fusion proteins and their use to treat cancer and cancer tumors.

BACKGROUND

The following description of the background of the present technology is provided simply as an aid in understanding the present technology and is not admitted to describe or constitute prior art to the present technology.

Cancer is the second leading cause of death in the United States, with a projected population of 18 million cancer patients in 2020 and annual costs exceeding $170 billion, and accounting for almost 600,000 deaths annually. Surgery remains the best treatment available, but its applicability is often restricted to localized primary tumors and associated lymph nodes. Broad-based approaches such as radiation and chemotherapy have long been used together with surgery to improve disease control or to treat metastatic disease and are effective against many cancer types, however neither approach can discriminate between rapidly dividing normal cells and cancerous cells, leading to adverse effects that often limit dosing to sub-efficacious levels, and subsets of tumor cells are either intrinsically resistant or can acquire resistance to these treatments through various mechanisms. These limitations motivated a shift in research focus to selectively target genetic and biochemical drivers of the disease.

SUMMARY OF THE PRESENT TECHNOLOGY

In one embodiment, the present technology discloses a fusion protein comprising an insulin polypeptide and an Fc fragment, wherein the insulin polypeptide comprises the sequence of SEQ ID NO: 6:

```
                                           (SEQ ID NO: 6)
FVNQHLCGSDLVEALALVCGERGFFYTDPTGGGPRRGIVEQCCHSICSLY

QLENYCN.
```

In an embodiment, the present technology discloses a fusion protein comprising an insulin polypeptide and an Fc fragment, wherein the insulin polypeptide comprises the sequence of SEQ ID NO: 37:

```
                                          (SEQ ID NO: 37)
FVNQHLCGSDLVEALALVCGERGFFYTDPTGGGPRRGIVEQCCHSICSLY

QLENYC.
```

In embodiments, the insulin polypeptide and the Fc fragment are connected by a linker comprising the sequence GGGGAGGGG (SEQ ID NO: 13). In embodiments, the insulin polypeptide and the Fc fragment are connected by a linker comprising the sequence GGGGAGGGGAGGGG (SEQ ID NO: 34). In embodiments, the insulin polypeptide and the Fc fragment are connected by a linker comprising the sequence GGGG (SEQ ID NO: 35). In embodiments, the insulin polypeptide and the Fc fragment are directly connected without a linker.

In some embodiments, the Fc fragment of the of the fusion protein comprises the sequence:

```
                                          (SEQ ID NO: 15)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPG.
```

In embodiments, the fusion protein comprises the sequence:

```
                                           (SEQ ID NO: 1)
FVNQHLCGSDLVEALALVCGERGFFYTDPTGGGPRRGIVEQCCHSICSLY

QLENYCNGGGGAGGGGDKTHTCPPCPAPELLGGPSVFLFPPKPKDTLMIS

RTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSF

FLYSKLTVDKSRWQQGNVFSCSVMHEALHNHYTQKSLSLSPG.
```

In embodiments, the fusion protein comprises the sequence:

```
                                          (SEQ ID NO: 18)
FVNQHLCGSDLVEALALVCGERGFFYTDPTGGGPRRGIVEQCCHSICSLY

QLENYCNGGGGAGGGGAGGGGDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG.
```

In embodiments, the fusion protein comprises the sequence:

```
                                          (SEQ ID NO: 20)
FVNQHLCGSDLVEALALVCGERGFFYTDPTGGGPRRGIVEQCCHSICSLY

QLENYCGGGGAGGGGDKTHTCPPCPAPELLGGPSVFLFPPKPKDTLMISR

TPEVTCVVVDVSHEDPEVKFNWYVDGVEVHNAKTKPREEQYNSTYRVVSV
```

-continued
LTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFF

LYSKLTVDKSRWQQGNVFSCSVMHEALHNHYTQKSLSLSPG.

In embodiments, the fusion protein comprises the sequence:

```
                                       (SEQ ID NO: 22)
FVNQHLCGSDLVEALALVCGERGFFYTDPTGGGPRRGIVEQCCHSICSLY

QLENYCNGGGGDKTHTCPPCPAPELLGGPSVFLFPPKPKDTLMISRTPEV

TCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSK

LTVDKSRWQQGNVFSCSVMHEALHNHYTQKSLSLSPG.
```

In embodiments, the fusion protein comprises the sequence:

```
                                       (SEQ ID NO: 24)
    FVNQHLCGSDLVEALALVCGERGFFYTDPTGG

GPRRGIVEQCCHSICSLYQLENYCNDKTHTCP

PCPAPELLGGPSVFLFPPKPKDTLMISRTPEV

TCVVVDVSHEDPEVKFNWYVDGVEVHNAKTKP

REEQYNSTYRVVSVLTVLHQDWLNGKEYKCKV

SNKALPAPIEKTISKAKGQPREPQVYTLPPSR

DELTKNQVSLTCLVKGFYPSDIAVEWESNGQP

ENNYKTTPPVLDSDGSFFLYSKLTVDKSRWQQ

GNVFSCSVMHEALHNHYTQKSLSLSPG.
```

In embodiments, the nucleic acid (cDNA) encoding the fusion protein of SEQ ID NO:
1 comprises the following nucleic acid sequence:

```
                                       (SEQ ID NO: 2)
    ATGGAATGGAGCTGGGTCTTTCTCTTCTTCCT

GTCAGTAACGACTGGTGTCCACTCCTTCGTGA

ACCAGCACCTGTGCGGCTCCGACCTGGTGGAA

GCTCTGGCTCTCGTGTGCGGCGAGCGGGGCTT

CTTCTACACCGATCCCACTGGAGGCGGTCCAC

GCAGAGGCATCGTGGAACAGTGCTGCCACTCC

ATCTGCTCCCTGTACCAGCTGGAAAACTACTG

CAATGGCGGAGGTGGTGCAGGAGGCGGTGGAG

ACAAAACTCACACATGCCCACCGTGCCCAGCA

CCTGAACTCCTGGGGGACCGTCAGTCTTCCT

CTTCCCCCCAAAACCCAAGGACACCCTCATGA

TCTCCCGGACCCCTGAGGTCACATGCGTGGTG

GTGGACGTGAGCCACGAAGACCCTGAGGTCAA

GTTCAACTGGTACGTGGACGGCGTGGAGGTGC
```

-continued
```
    ATAATGCCAAGACAAAGCCGCGGGAGGAGCAG

TACAACAGCACGTACCGTGTGGTCAGCGTCCT

CACCGTCCTGCACCAGGACTGGCTGAATGGCA

AGGAGTACAAGTGCAAGGTCTCCAACAAAGCC

CTCCCAGCCCCCATCGAGAAAACCATCTCCAA

AGCCAAAGGGCAGCCCCGAGAACCACAGGTGT

ACACCCTGCCCCCATCCCGGGATGAGCTGACC

AAGAACCAGGTCAGCCTGACCTGCCTGGTCAA

AGGCTTCTATCCCAGCGACATCGCCGTGGAGT

GGGAGAGCAATGGGCAGCCGGAGAACAACTAC

AAGACCACGCCTCCCGTGCTGGACTCCGACGG

CTCCTTCTTCCTCTACAGCAAGCTCACCGTGG

ACAAGAGCAGGTGGCAGCAGGGGAACGTCTTC

TCATGCTCCGTGATGCATGAGGCTCTGCACAA

CCACTACACGCAGAAGAGCCTCTCCCTGTCTC

CGGGTTAG.
```

In embodiments, the nucleic acid (cDNA) encoding the fusion protein of SEQ ID NO:
18 comprises the following nucleic acid sequence:

```
                                       (SEQ ID NO: 19)
    ATGGAATGGAGCTGGGTCTTTCTCTTCTTCCT

GTCAGTAACGACTGGTGTCCACTCCTTCGTGA

ACCAGCACCTGTGCGGCTCCGACCTGGTGGAA

GCTCTGGCTCTCGTGTGCGGCGAGCGGGGCTT

CTTCTACACCGATCCCACTGGAGGCGGTCCAC

GCAGAGGCATCGTGGAACAGTGCTGCCACTCC

ATCTGCTCCCTGTACCAGCTGGAAAACTACTG

CAATGGCGGAGGAGCTGGCGGAGGTGGTG

CAGGAGGCGGTGGAGACAAAACTCACACATGC

CCACCGTGCCCAGCACCTGAACTCCTGGGGGG

ACCGTCAGTCTTCCTCTTCCCCCCAAAACCCA

AGGACACCCTCATGATCTCCCGGACCCCTGAG

GTCACATGCGTGGTGGTGGACGTGAGCCACGA

AGACCCTGAGGTCAAGTTCAACTGGTACGTGG

ACGGCGTGGAGGTGCATAATGCCAAGACAAAG

CCGCGGGAGGAGCAGTACAACAGCACGTACCG

TGTGGTCAGCGTCCTCACCGTCCTGCACCAGG

ACTGGCTGAATGGCAAGGAGTACAAGTGCAAG

GTCTCCAACAAAGCCCTCCCAGCCCCCATCGA

GAAAACCATCTCCAAAGCCAAAGGGCAGCCCC

GAGAACCACAGGTGTACACCCTGCCCCCATCC
```

-continued

```
CGGGATGAGCTGACCAAGAACCAGGTCAGCCT
GACCTGCCTGGTCAAAGGCTTCTATCCCAGCG
ACATCGCCGTGGAGTGGGAGAGCAATGGGCAG
CCGGAGAACAACTACAAGACCACGCCTCCCGT
GCTGGACTCCGACGGCTCCTTCTTCCTCTACA
GCAAGCTCACCGTGGACAAGAGCAGGTGGCAG
CAGGGGAACGTCTTCTCATGCTCCGTGATGCA
TGAGGCTCTGCACAACCACTACACGCAGAAGA
GCCTCTCCCTGTCTCCGGGTTAG.
```

In embodiments, the nucleic acid (cDNA) encoding the fusion protein of SEQ ID NO: 20 comprises the following nucleic acid sequence:

(SEQ ID NO: 21)
```
ATGGAATGGAGCTGGGTCTTTCTCTTCTTCCT
GTCAGTAACGACTGGTGTCCACTCCTTCGTGA
ACCAGCACCTGTGCGGCTCCGACCTGGTGGAA
GCTCTGGCTCTCGTGTGCGGCGAGCGGGCTT
CTTCTACACCGATCCCACTGGAGGCGGTCCAC
GCAGAGGCATCGTGGAACAGTGCTGCCACTCC
ATCTGCTCCCTGTACCAGCTGGAAAACTACTG
CGGCGGAGGTGGTGCAGGAGGCGGTGGAGACA
AAACTCACACATGCCCACCGTGCCCAGCACCT
GAACTCCTGGGGGGACCGTCAGTCTTCCTCTT
CCCCCCAAAACCCAAGGACACCCTCATGATCT
CCCGGACCCCTGAGGTCACATGCGTGGTGGTG
GACGTGAGCCACGAAGACCCTGAGGTCAAGTT
CAACTGGTACGTGGACGGCGTGGAGGTGCATA
ATGCCAAGACAAAGCCGCGGGAGGAGCAGTAC
AACAGCACGTACCGTGTGGTCAGCGTCCTCAC
CGTCCTGCACCAGGACTGGCTGAATGGCAAGG
AGTACAAGTGCAAGGTCTCCAACAAAGCCCTC
CCAGCCCCCATCGAGAAAACCATCTCCAAAGC
CAAAGGGCAGCCCCGAGAACCACAGGTGTACA
CCCTGCCCCCATCCCGGGATGAGCTGACCAAG
AACCAGGTCAGCCTGACCTGCCTGGTCAAAGG
CTTCTATCCCAGCGACATCGCCGTGGAGTGGG
AGAGCAATGGGCAGCCGGAGAACAACTACAAG
ACCACGCCTCCCGTGCTGGACTCCGACGGCTC
CTTCTTCCTCTACAGCAAGCTCACCGTGGACA
AGAGCAGGTGGCAGCAGGGGAACGTCTTCTCA
TGCTCCGTGATGCATGAGGCTCTGCACAACCA
```

```
CTACACGCAGAAGAGCCTCTCCCTGTCTCCGG
GTTAG.
```

In embodiments, the nucleic acid (cDNA) encoding the fusion protein of SEQ ID NO: 22 comprises the following nucleic acid sequence:

(SEQ ID NO: 23)
```
ATGGAATGGAGCTGGGTCTTTCTCTTCTTCCT
GTCAGTAACGACTGGTGTCCACTCCTTCGTGA
ACCAGCACCTGTGCGGCTCCGACCTGGTGGAA
GCTCTGGCTCTCGTGTGCGGCGAGCGGGCTT
CTTCTACACCGATCCCACTGGAGGCGGTCCAC
GCAGAGGCATCGTGGAACAGTGCTGCCACTCC
ATCTGCTCCCTGTACCAGCTGGAAAACTACTG
CAATGGAGGCGGTGGAGACAAAACTCACACAT
GCCCACCGTGCCCAGCACCTGAACTCCTGGGG
GGACCGTCAGTCTTCCTCTTCCCCCCAAAACC
CAAGGACACCCTCATGATCTCCCGGACCCCTG
AGGTCACATGCGTGGTGGTGGACGTGAGCCAC
GAAGACCCTGAGGTCAAGTTCAACTGGTACGT
GGACGGCGTGGAGGTGCATAATGCCAAGACAA
AGCCGCGGGAGGAGCAGTACAACAGCACGTAC
CGTGTGGTCAGCGTCCTCACCGTCCTGCACCA
GGACTGGCTGAATGGCAAGGAGTACAAGTGCA
AGGTCTCCAACAAAGCCCTCCCAGCCCCCATC
GAGAAAACCATCTCCAAAGCCAAAGGGCAGCC
CCGAGAACCACAGGTGTACACCCTGCCCCCAT
CCCGGGATGAGCTGACCAAGAACCAGGTCAGC
CTGACCTGCCTGGTCAAAGGCTTCTATCCCAG
CGACATCGCCGTGGAGTGGGAGAGCAATGGGC
AGCCGGAGAACAACTACAAGACCACGCCTCCC
GTGCTGGACTCCGACGGCTCCTTCTTCCTCTA
CAGCAAGCTCACCGTGGACAAGAGCAGGTGGC
AGCAGGGGAACGTCTTCTCATGCTCCGTGATG
CATGAGGCTCTGCACAACCACTACACGCAGAA
GAGCCTCTCCCTGTCTCCGGGTTAG.
```

In embodiments, the nucleic acid (cDNA) encoding the fusion protein of SEQ ID NO: 24 comprises the following nucleic acid sequence:

(SEQ ID NO: 25)
```
ATGGAATGGAGCTGGGTCTTTCTCTTCTTCCT
GTCAGTAACGACTGGTGTCCACTCCTTCGTGA
```

```
            -continued
ACCAGCACCTGTGCGGCTCCGACCTGGTGGAA

GCTCTGGCTCTCGTGTGCGGCGAGCGGGCTT

CTTCTACACCGATCCCACTGGAGGCGGTCCAC

GCAGAGGCATCGTGGAACAGTGCTGCCACTCC

ATCTGCTCCCTGTACCAGCTGGAAAACTACTG

CAATGACAAAACTCACACATGCCCACCGTGCC

CAGCACCTGAACTCCTGGGGGACCGTCAGTC

TTCCTCTTCCCCCCAAAACCCAAGGACACCCT

CATGATCTCCCGGACCCCTGAGGTCACATGCG

TGGTGGTGGACGTGAGCCACGAAGACCCTGAG

GTCAAGTTCAACTGGTACGTGGACGGCGTGGA

GGTGCATAATGCCAAGACAAAGCCGCGGGAGG

AGCAGTACAACAGCACGTACCGTGTGGTCAGC

GTCCTCACCGTCCTGCACCAGGACTGGCTGAA

TGGCAAGGAGTACAAGTGCAAGGTCTCCAACA

AAGCCCTCCCAGCCCCCATCGAGAAAACCATC

TCCAAAGCCAAAGGGCAGCCCCGAGAACCACA

GGTGTACACCCTGCCCCCATCCCGGGATGAGC

TGACCAAGAACCAGGTCAGCCTGACCTGCCTG

GTCAAAGGCTTCTATCCCAGCGACATCGCCGT

GGAGTGGGAGAGCAATGGGCAGCCGGAGAACA

ACTACAAGACCACGCCTCCCGTGCTGGACTCC

GACGGCTCCTTCTTCCTCTACAGCAAGCTCAC

CGTGGACAAGAGCAGGTGGCAGCAGGGGAACG

TCTTCTCATGCTCCGTGATGCATGAGGCTCTG

CACAACCACTACACGCAGAAGAGCCTCTCCCT

GTCTCCGGGTTAG.
```

According to aspects of the invention described herein, with respect to the ratio of IC50 for the fusion protein to IC50 for recombinant human insulin (RHI) (e.g., the IC50 ratio) the preferred IC50 ratio is less than or equal to 20, or more preferably, the IC50 ratio is less than or equal to 8. Embodiments with lower IC50 ratios demonstrate higher affinities for the insulin receptor than embodiments with higher IC50 ratios. Insulin-Fc fusion proteins that are dimeric with respect to the insulin polypeptide (e.g. two moles of insulin polypeptide chain per mole of insulin-Fc homodimer, e.g. 2 moles of insulin analog B-chain and 2 moles of insulin analog A-chain per mole of insulin-Fc homodimer) with IC50 ratios less than or equal to 20, or more preferably fusion proteins with IC50 ratios less than or equal to 8 demonstrate greater downregulation of the insulin receptor (IR) compared to recombinant human insulin (RHI) (e.g. which has one mole of insulin polypeptide with respect to RHI, e.g. one mole of insulin B-chain and one mole of insulin A-chain per mole of RHI). Without wishing to be bound by any theory, it is hypothesized that insulin-Fc fusion proteins that (i) are dimeric with respect to the insulin polypeptide (e.g., two insulin polypeptide chains per insulin-Fc homodimer) and (ii) demonstrate IC50 ratios preferably less than or equal to 20 or more preferably less than or equal to 8, will demonstrate the ability to downregulate the insulin receptor (as shown in FIG. 5). Downregulation of the insulin receptor is a key aspect to the efficacy of the preferred fusion proteins of the present technology.

In embodiments, a cell may be engineered to express the fusion protein. The cell may be transfected with a nucleic acid encoding the fusion protein. In some examples, the cell is a HEK293 cell or a CHO cell.

In some embodiments, the dimer of the fusion protein comprises two identical monomers bound together via disulfide bonds, e.g., the fusion protein is a homodimer.

In some embodiments, the duration of activity of the fusion protein (that is, the time during which there is a statistically significant decrease in blood glucose level in a subject relative to a pre-dose level) is longer than about 2 hours, 6 hours, 9 hours, 12 hours, 18 hours, 1 day, 1.5 days, 2 days, 2.2 days, 2.5 days, 3 days, 5 days, or longer.

In one embodiment, the present technology discloses a pharmaceutical composition for inhibiting cancer cell metabolism, growth, and/or proliferation, wherein the pharmaceutical composition comprises a fusion protein dispersed in a pharmaceutically acceptable carrier (e.g. a buffer, e.g. a sodium phosphate buffer, e.g. a sodium phosphate and sodium chloride solution, e.g. a buffer solution optionally contains an additive, e.g. wherein the additive is polysorbate-20 or polysorbate-80) wherein the fusion protein comprises an insulin polypeptide and an Fc fragment connected by a linker, and where the ratio of $IC_{50}$ for the fusion protein to $IC_{50}$ for recombinant human insulin (SEQ ID NO: 5) is less than or equal to 20. In embodiments, the pharmaceutical composition comprises a fusion protein comprising the insulin polypeptide of FVNQHLCGSDLVEALALVCGERGFFYTDPTGGGPRRGIVEQCCHSICSLYQLENYCN (SEQ ID NO: 6) or the insulin polypeptide of (SEQ ID NO: 37): FVNQHLCGSDLVEALALVCGERGFFYTDPTGGGPRRGIVEQCCHSICSLYQLENYC.

In embodiments, the pharmaceutical composition comprises a fusion protein wherein the insulin polypeptide and the Fc fragment of the fusion protein are connected by a linker comprising the sequence GGGGAGGGG (SEQ ID NO: 13). In embodiments, the pharmaceutical composition comprises a fusion protein wherein the insulin polypeptide and the Fc fragment are connected by a linker comprising the sequence GGGGAGGGGAGGGG (SEQ ID NO: 34). In embodiments, the pharmaceutical composition comprises a fusion protein wherein the insulin polypeptide and the Fc fragment are connected by a linker comprising the sequence GGGG (SEQ ID NO: 35). In embodiments, the pharmaceutical composition comprises a fusion protein wherein the insulin polypeptide and the Fc fragment are directly connected without a linker.

In embodiments, the pharmaceutical composition comprises a fusion protein dispersed in a pharmaceutically acceptable carrier, wherein the Fc fragment of the fusion protein comprises the sequence:

```
                                (SEQ ID NO: 15)
DKTHTCPPCPAPELLGGPSVFLFPPKPKDTLM
ISRTPEVTCVVVDVSHEDPEVKFNWYVDGVEV
HNAKTKPREEQYNSTYRVVSVLTVLHQDWLNG
```

KEYKCKVSNKALPAPIEKTISKAKGQPREPQV

YTLPPSRDELTKNQVSLTCLVKGFYPSDIAVE

WESNGQPENNYKTTPPVLDSDGSFFLYSKLTV

DKSRWQQGNVFSCSVMHEALHNHYTQKSLSLS

PG.

In one embodiment, the present technology discloses a pharmaceutical composition for inhibiting cancer cell metabolism, growth, and/or proliferation, wherein the pharmaceutical composition comprises a fusion protein dispersed in a pharmaceutically acceptable carrier, the fusion protein comprising an insulin polypeptide and an Fc fragment, wherein the insulin polypeptide and the Fc fragment are connected by a linker, and wherein the fusion protein comprises the sequence:

```
                               (SEQ ID NO: 1)
FVNQHLCGSDLVEALALVCGERGFFYTDPTGG

GPRRGIVEQCCHSICSLYQLENYCNGGGGAGG

GGDKTHTCPPCPAPELLGGPSVFLFPPKPKDT

LMISRTPEVTCVVVDVSHEDPEVKFNWYVDGV

EVHNAKTKPREEQYNSTYRVVSVLTVLHQDWL

NGKEYKCKVSNKALPAPIEKTISKAKGQPREP

QVYTLPPSRDELTKNQVSLTCLVKGFYPSDIA

VEWESNGQPENNYKTTPPVLDSDGSFFLYSKL

TVDKSRWQQGNVFSCSVMHEALHNHYTQKSLS

LSPG.
```

In one embodiment, the present technology discloses a pharmaceutical composition for inhibiting cancer cell metabolism, growth, and/or proliferation, wherein the pharmaceutical composition comprises a fusion protein dispersed in a pharmaceutically acceptable carrier, the fusion protein comprising an insulin polypeptide and an Fc fragment, wherein the insulin polypeptide and the Fc fragment are connected by a linker, and wherein the fusion protein comprises the sequence:

```
                              (SEQ ID NO: 18)
FVNQHLCGSDLVEALALVCGERGFFYTDPTGG

GPRRGIVEQCCHSICSLYQLENYCNGGGGAGG

GGAGGGGDKTHTCPPCPAPELLGGPSVFLFPP

KPKDTLMISRTPEVTCVVVDVSHEDPEVKFNW

YVDGVEVHNAKTKPREEQYNSTYRVVSVLTVL

HQDWLNGKEYKCKVSNKALPAPIEKTISKAKG

QPREPQVYTLPPSRDELTKNQVSLTCLVKGFY

PSDIAVEWESNGQPENNYKTTPPVLDSDGSFF

LYSKLTVDKSRWQQGNVFSCSVMHEALHNHYT

QKSLSLSPG.
```

In one embodiment, the present technology discloses a pharmaceutical composition for inhibiting cancer cell metabolism, growth, and/or proliferation, wherein the pharmaceutical composition comprises a fusion protein dispersed in a pharmaceutically acceptable carrier, the fusion protein comprising an insulin polypeptide and an Fc fragment, wherein the insulin polypeptide and the Fc fragment are connected by a linker, and wherein the fusion protein comprises the sequence:

```
                              (SEQ ID NO: 20)
FVNQHLCGSDLVEALALVCGERGFFYTDPTGG

GPRRGIVEQCCHSICSLYQLENYCGGGGAGGG

GDKTHTCPPCPAPELLGGPSVFLFPPKPKDTL

MISRTPEVTCVVVDVSHEDPEVKFNWYVDGVE

VHNAKTKPREEQYNSTYRVVSVLTVLHQDWLN

GKEYKCKVSNKALPAPIEKTISKAKGQPREPQ

VYTLPPSRDELTKNQVSLTCLVKGFYPSDIAV

EWESNGQPENNYKTTPPVLDSDGSFFLYSKLT

VDKSRWQQGNVFSCSVMHEALHNHYTQKSLSL

SPG.
```

In one embodiment, the present technology discloses a pharmaceutical composition for inhibiting cancer cell metabolism, growth, and/or proliferation, wherein the pharmaceutical composition comprises a fusion protein dispersed in a pharmaceutically acceptable carrier, the fusion protein comprising an insulin polypeptide and an Fc fragment, wherein the insulin polypeptide and the Fc fragment are connected by a linker, and wherein the fusion protein comprises the sequence:

```
                              (SEQ ID NO: 22)
FVNQHLCGSDLVEALALVCGERGFFYTDPTGG

GPRRGIVEQCCHSICSLYQLENYCNGGGGDKT

HTCPPCPAPELLGGPSVFLFPPKPKDTLMISR

TPEVTCVVVDVSHEDPEVKFNWYVDGVEVHNA

KTKPREEQYNSTYRVVSVLTVLHQDWLNGKEY

KCKVSNKALPAPIEKTISKAKGQPREPQVYTL

PPSRDELTKNQVSLTCLVKGFYPSDIAVEWES

NGQPENNYKTTPPVLDSDGSFFLYSKLTVDKS

RWQQGNVFSCSVMHEALHNHYTQKSLSLSPG.
```

In one embodiment, the present technology discloses a pharmaceutical composition for inhibiting cancer cell metabolism, growth, and/or proliferation, wherein the pharmaceutical composition comprises a fusion protein dispersed in a pharmaceutically acceptable carrier, the fusion protein comprising an insulin polypeptide and an Fc fragment, wherein the insulin polypeptide and the Fc fragment are connected by a linker, and wherein the fusion protein comprises the sequence:

```
                              (SEQ ID NO: 24)
FVNQHLCGSDLVEALALVCGERGFFYTDPTGG

GPRRGIVEQCCHSICSLYQLENYCNDKTHTCP
```

-continued

PCPAPELLGGPSVFLFPPKPKDTLMISRTPEV

TCVVVDVSHEDPEVKFNWYVDGVEVHNAKTKP

REEQYNSTYRVVSVLTVLHQDWLNGKEYKCKV

SNKALPAPIEKTISKAKGQPREPQVYTLPPSR

DELTKNQVSLTCLVKGFYPSDIAVEWESNGQP

ENNYKTTPPVLDSDGSFFLYSKLTVDKSRWQQ

GNVFSCSVMHEALHNHYTQKSLSLSPG.

In embodiments, the pharmaceutical composition for use in treating cancer, wherein the pharmaceutical composition comprises a fusion protein dispersed in a pharmaceutically acceptable carrier, and wherein the pharmaceutical composition exhibits an anti-tumor effect on a cancer cell, wherein the anti-tumor effect is selected from the group consisting of downregulation of insulin receptor, downregulation of insulin-like growth factor 1 receptor (IGF1R), decreased phosphorylated Akt, or a combination thereof, as compared to an untreated control cancer cell.

In embodiments, the present technology discloses a method of inhibiting cancer cell metabolism, growth, and/or proliferation or cancer tumor growth, the method comprising administering an effective amount of a fusion protein or administering a pharmaceutical composition comprising an effective amount of a fusion protein dispersed in a pharmaceutically acceptable carrier, to a mammal in need thereof. That is, the fusion protein inhibits cancer cell metabolism, growth, and/or proliferation or cancer tumor growth in the mammal after the administration of the fusion protein. In embodiments, the fusion protein or the pharmaceutical composition comprising an effective amount of a fusion protein dispersed in a pharmaceutically acceptable carrier is administered to said mammal under fasted conditions. In embodiments, the mammal has been diagnosed with a cancer selected from the group consisting of breast cancer, colorectal cancer, and melanoma.

In some embodiments, the mammal may exhibit a reduction in tumor volume of at least 40% after the administration of the insulin-Fc fusion protein, compared to a fasted untreated control. In some embodiments, the mammal may exhibit a reduction in tumor volume of at least 30% after the administration of the insulin-Fc fusion protein, compared to an unfasted untreated control. In embodiments, the primary or secondary cancer therapy are selected from the group consisting of chemotherapy agents, tamoxifen agonists, or antibodies against the IGF1 receptor.

In embodiments, the present technology discloses a method of inhibiting cancer cell metabolism, growth, and/or proliferation or cancer tumor growth, wherein the method comprises administering an effective amount of a fusion protein or of a pharmaceutical composition comprising the fusion protein dispersed in a pharmaceutically acceptable carrier exhibits an anti-tumor effect on a cancer cell, wherein the anti-tumor effect is selected from the group consisting of downregulation of insulin receptor, downregulation of insulin-like growth factor 1 receptor (IGF1R), decreased phosphorylated Akt, or a combination thereof, as compared to an untreated control cancer cell.

In embodiments, the fusion protein or a pharmaceutical composition comprising the fusion protein dispersed in a pharmaceutically acceptable carrier is administered by intravenous injection, by subcutaneous injection, or by intratumorol injection. In embodiments, the fusion protein a pharmaceutical composition comprising the fusion protein dispersed in a pharmaceutically acceptable carrier is administered as a bolus, as an infusion, or as an intravenous push. In embodiments, the fusion protein or a pharmaceutical composition comprising the fusion protein dispersed in a pharmaceutically acceptable carrier is administered through syringe injection, or using a pump, a pen, a needle, or an indwelling catheter.

The present invention is also directed to the use of the fusion protein of the invention for the manufacture of a medicament for the treatment of cancer, preferably inhibiting cancer cell metabolism, growth, and/or proliferation.

Ideally, the cancer is selected from breast cancer, colorectal cancer, or melanoma. Furthermore, said fusion protein may exhibit an anti-tumor effect on a cancer cell in said subject after administration, said anti-tumor effect being selected from the group consisting of downregulation of insulin receptor, downregulation of insulin-like growth factor 1 receptor (IGF1R), decreased phosphorylated Akt, and a combination thereof, as compared to an untreated control cancer cell.

Ideally, the fusion protein is for use via intravenous, subcutaneous, or intratumoral injection and/or may be administered as a bolus, infusion, or an intravenous push. Preferably, the fusion protein may be administered through syringe injection, pump, pen, needle, or indwelling catheter. Additionally, the fusion protein may be co-administered with a primary or secondary cancer therapy selected from the group consisting of chemotherapy agents, tamoxifen agonists, or antibodies against the IGF1 receptor.

According to a preferred embodiment, the fusion may be administered to said subject at a dose of from about 150 to about 1,500 micrograms per kilogram of body weight per day. Additionally, the fusion protein may be administered to a subject under fasted or unfasted conditions.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In the case of conflict, the present specification, including Definitions, will control. In addition, the materials, methods, and examples are illustrative only and are not intended to be limiting. Other features and advantages of the disclosure will be apparent from the following Detailed Description, Examples, and Claims.

BRIEF DESCRIPTION OF THE DRAWINGS

FIG. 2 illustrates the "full aa sequence" of a fusion protein (SEQ ID NO: 1) including the leader sequence of SEQ ID NO: 16, that is the cDNA sequence of SEQ ID NO: 17 and the cDNA sequence of SEQ ID NO: 2 corresponding to the amino acid sequence of SEQ ID NO: 16 and SEQ ID NO: 1, respectively;

FIG. 3 illustrates the "full aa sequence" of a fusion protein (SEQ ID NO: 3) including the leader sequence of SEQ ID NO: 16, that is the cDNA sequence of SEQ ID NO: 17 and the cDNA sequence of SEQ ID NO: 4 corresponding to the amino acid sequence of SEQ ID NO: 16 and SEQ ID NO: 3, respectively;

FIG. 4 illustrates a side-by-side sequence comparison of SEQ ID NO: 1, SEQ ID NO: 3, SEQ ID NO: 18, SEQ ID NO: 20, SEQ ID NO: 22, SEQ ID NO: 24, SEQ ID NO: 26, and SEQ ID NO: 28. "*" represents complete homology across all sequences at a given sequence position, while ":", "." or spaces refer to conservative, moderate, or very different amino acid mutations across the sequences at a given sequence position, respectively;

DETAILED DESCRIPTION

Figure 1:
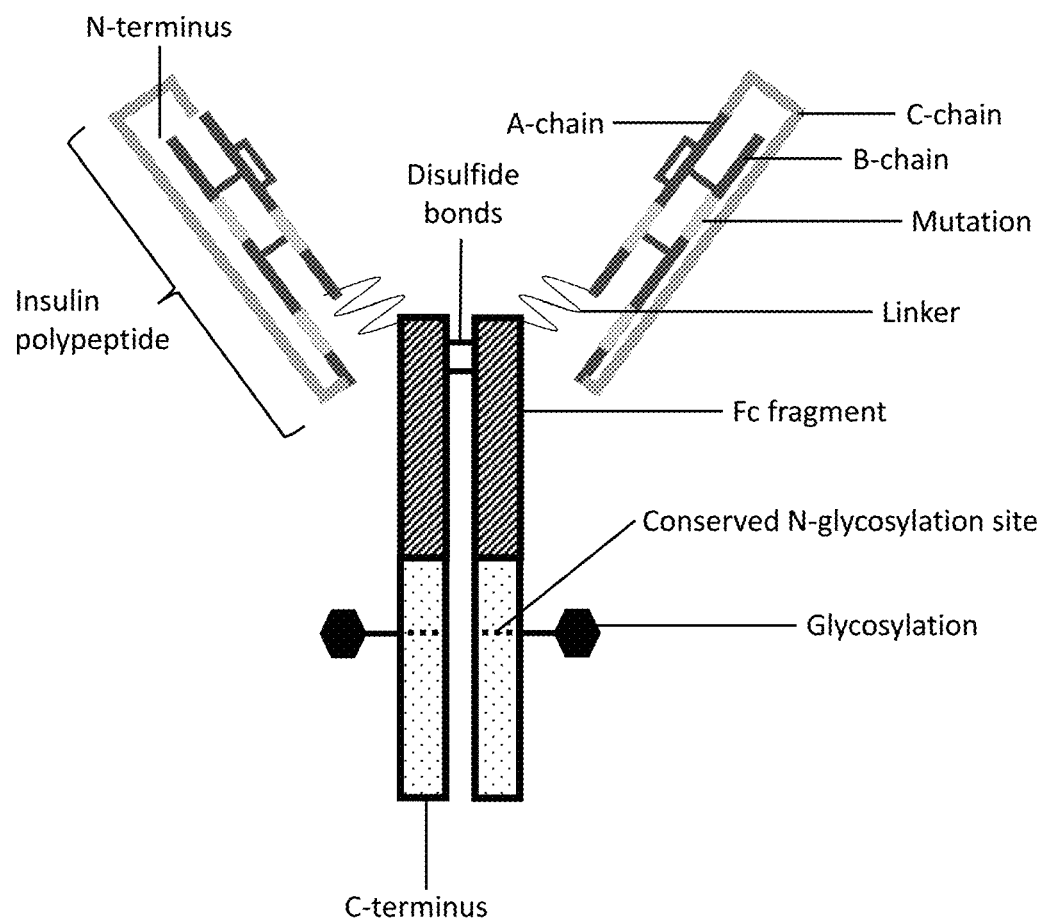
FIG. 1 shows a schematic representation of an exemplary insulin-Fc fusion protein homodimer.

The present disclosure relates to compositions of fusion proteins, e.g., insulin-Fc fusion proteins, and their use to treat cancer tumors.

Definitions

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values.

As used herein, an amount of a molecule, compound, conjugate, or substance effective to treat a disorder (e.g., a disorder described herein), "therapeutically effective amount," or "effective amount" refers to an amount of the molecule, compound, conjugate, or substance which is effective, upon single or multiple dose administration(s) to a subject, in treating a subject, or in curing, alleviating, relieving or improving a subject with a disorder (e.g., a disorder described herein) beyond that expected in the absence of such treatment.

As used herein, the term "analog" refers to a compound or conjugate (e.g., a compound or conjugate as described herein, e.g., insulin) having a chemical structure similar to that of another compound or conjugate but differing from it in at least one aspect.

As used herein, the term "antibody" or "antibody molecule" refers to an immunoglobulin molecule (Ig), immunologically active portions of an immunoglobulin (Ig) molecule, i.e., a molecule that contains an antigen binding site that specifically binds, e.g., immunoreacts with, an antigen. As used herein, the term "antibody domain" refers to a variable or constant region of an immunoglobulin. As used herein, the term "antibody domain" refers to a variable or constant region of an immunoglobulin. It is documented in the art that antibodies comprise several classes, for example IgA, IgM, or IgG in the case of mammals (e.g., humans). Classes of immunoglobulins can be further classified into different isotypes such as IgGA, IgGB, IgGC, and IgGD for canines, and IgG1, IgG2, IgG3, and IgG4 for humans. Those skilled in the art will recognize that immunoglobulin isotypes of a given immunoglobulin class will comprise different amino acid sequences, structures, and functional properties from one another (e.g., different binding affinities to Fc(gamma) receptors). "Specifically binds" or "immunoreacts with" means that the antibody reacts with one or more antigenic determinants of the desired antigen and has a lower affinity for other polypeptides, e.g., does not react with other polypeptides.

As used herein the terms "insulin-Fc fusion protein" or "insulin-Fc protein" or "fusion protein" or "insulin-Fc fusion homodimer" refer to a protein comprising an insulin protein and an Fc fragment.

As used herein, the term "bioactivity," "activity," "biological activity," "potency," "bioactive potency," or "biological potency" refers to the extent to which an insulin-Fc fusion protein activates the IR and/or exerts a reduction in blood glucose levels in a target subject. As used herein, "in vitro activity" or "IR activity" refers to the affinity with which an insulin-Fc fusion protein binds to the IR and is typically measured by the concentration at which an insulin-Fc fusion protein displaces half of an insulin reference standard from the IR in a competitive binding assay (i.e., IC50). As used herein, "in vivo activity" refers to the extent and duration of reduction in a target subject's fasting blood glucose level after administration of an insulin-Fc fusion protein.

As used herein, the term "biosynthesis," "recombinant synthesis," or "recombinantly made" refers to the process by which an insulin-Fc fusion protein is expressed within a host cell by transfecting the cell with a nucleic acid molecule (e.g., vector) encoding the insulin-Fc fusion protein (e.g., where the entire insulin-Fc fusion protein is encoded by a single nucleic acid molecule). Exemplary host cells include mammalian cells, e.g., HEK293 cells or CHO cells. The cells can be cultured using standard methods in the art and the expressed insulin-Fc fusion protein may be harvested and purified from the cell culture using standard methods in the art.

As used herein, the term "cell surface receptor" refers to a molecule such as a protein, generally found on the external surface of the membrane of a cell and which interacts with soluble molecules, e.g., molecules that circulate in the blood supply. In some embodiments, a cell surface receptor may include a hormone receptor (e.g., an insulin hormone receptor or insulin receptor (IR)) or an Fc receptor which binds to an Fc fragment or the Fc region of an antibody (e.g., an Fc(gamma) receptor, for example Fc(gamma)RI, or an Fc neonatal receptor, for example FcRn). As used herein, "in vitro activity" or "Fc(gamma) receptor activity" or "Fc (gamma) receptor binding" or "FcRn receptor activity" or "FcRn binding" refers to the affinity with which an insulin-Fc fusion protein binds to the Fc receptor (e.g. Fc(gamma) receptor or FcRn receptor) and is typically measured by the concentration of an insulin-Fc fusion protein that causes the insulin-Fc fusion protein to reach half of its maximum binding (i.e., EC50 value) as measured on an assay (e.g., an enzyme-linked immunosorbent assay (ELISA) assay) using OD 450 nm values as measured on a microplate reader. Alternatively, the affinity with which an insulin-Fc fusion protein binds to the Fc receptor (e.g., Fc(gamma) receptor or FcRn receptor) is measured by the OD 450 nm value obtained on a microplate reader in an enzyme-linked immunosorbent assay (ELISA) assay at a given concentration of the insulin-Fc fusion protein.

As used herein, the term "C1q" or "complement component 1q" means a protein complex involved in the complement system, which is part of the innate immune system. C1q together with C1r and C1s form the C1 complex. C1q plays a role in involved in specific antigen presentation by dendritic cells to T cells and B cells.

As used herein, the term "fasting blood glucose level" or "FBGL" refers to the average blood glucose level in a target subject at the end of a period during which no food is administered and just prior to the time at which an insulin-Fc fusion protein is administered. As used herein, the term "percent fasting blood glucose level," "% fasting blood glucose level," or "% FBGL" refers to the ratio of a given blood glucose level to the fasting blood glucose level multiplied by 100.

As used herein, the term "immunogenic" or "immunogenicity" refers to the capacity for a given molecule (e.g., an insulin-Fc fusion protein of the present invention) to provoke the immune system of a target subject such that after repeated administrations of the molecule, the subject develops antibodies capable of specifically binding the molecule (i.e., anti-drug antibodies). As used herein, the terms "neutralizing," "neutralizing antibodies", or "neutralizing anti-drug antibodies" refer to the capacity for antibodies to interfere with the compound's biological activity in the target subject. As used herein, the term "immunogenic epitopes," 'immunogenic hot spots," or "hot spots" refers to the mutations or epitopes of a given molecule (e.g., an insulin-Fc fusion protein of the present invention) that are responsible for moderate or strong binding of the anti-drug antibodies.

As used herein, the term "insulin reference standard" is any one of: (i) a naturally occurring insulin from a mammal (e.g., a human); (ii) an insulin polypeptide that does not comprise an Fc fragment; or (iii) a standard of care insulin (e.g., a commercially available insulin).

As used herein, the term "monomer" refers to a protein or a fusion protein comprising a single polypeptide. In embodiments, the "monomer" is a protein or a fusion protein, e.g., a single polypeptide, comprising an insulin polypeptide and an Fc fragment polypeptide, wherein the insulin and Fc fragment polypeptides are joined by peptide bonds to form the single polypeptide. In embodiments, the monomer is encoded by a single nucleic acid molecule.

As used herein, "N-terminus" refers to the start of a protein or polypeptide that is initiated by an amino acid containing a free amine group that is the alpha-amino group of the amino acid (e.g., the free amino that is covalently linked to one carbon atom that is located adjacent to a second carbon atom, wherein the second carbon atom is part of the carbonyl group of the amino acid). As used herein, "C-terminus" refers to the end of a protein or polypeptide that is terminated by an amino acid containing a carboxylic acid group, wherein the carbon atom of the carboxylic acid group is located adjacent to the alpha-amino group of the amino acid.

As used herein, "pharmacodynamics" or "PD" generally refers to the biological effects of an insulin-Fc fusion protein in a subject. Specifically, herein the PD refers to the measure of the reduction in fasting blood glucose level over time in a subject after the administration of an insulin-Fc fusion protein.

As used herein, "pharmacokinetics" or "PK" generally refers to the characteristic interactions of an insulin-Fc fusion protein and the body of the subject in terms of its absorption, distribution, metabolism, and excretion. Specifically, herein the PK refers to the concentration of an insulin-Fc fusion protein in the blood or serum of a subject at a given time after the administration of the insulin-Fc fusion protein. As used herein, "half-life" refers to the time taken for the concentration of insulin-Fc fusion protein in the blood or serum of a subject to reach half of its original value as calculated from a first order exponential decay model for drug elimination. Insulin-Fc fusion proteins with greater "half-life" values demonstrate greater duration of action in the target subject.

The terms "sequence identity" "sequence homology" "homology" or "identical" in amino acid or nucleotide sequences as used herein describes that the same nucleotides or amino acid residues are found within the variant and reference sequences when a specified, contiguous segment of the nucleotide sequence or amino acid sequence of the variant is aligned and compared to the nucleotide sequence or amino acid sequence of the reference sequence. Methods for sequence alignment and for determining identity between sequences are known in the art, including the use of Clustal Omega, which organizes, aligns, and compares sequences for similarity, wherein the software highlights each sequence position and compares across all sequences at that position and assigns one of the following scores: an "*" (asterisk) for sequence positions which have a single, fully conserved residue, a ":" (colon) indicates conservation between groups of strongly similar properties with scoring greater than 0.5 in the Gonnet PAM 250 matrix, and a "." (period) indicates conservation between groups of weakly similar properties with scoring less than or equal to 0.5 in the Gonnet PAM 250 matrix, a "-" (dash) indicates a sequence gap, meaning that no local homology exists within a particular set of comparisons within a certain range of the sequences, and an empty space " " indicates little or no sequence homology for that particular position across the compared sequences. See, for example Ausubel et al., eds. (1995) *Current Protocols in Molecular Biology*, Chapter 19 (Greene Publishing and Wiley-Interscience, New York); and the ALIGN program (Dayhoff (1978) in *Atlas of Polypeptide Sequence and Structure* 5: Suppl. 3 (National Biomedical Research Foundation, Washington, D.C.)). With respect to optimal alignment of two nucleotide sequences, the contiguous segment of the variant nucleotide sequence may have additional nucleotides or deleted nucleotides with respect to the reference nucleotide sequence. Likewise, for purposes of optimal alignment of two amino acid sequences, the contiguous segment of the variant amino acid sequence may have additional amino acid residues or deleted amino acid residues with respect to the reference amino acid sequence. In some embodiments, the contiguous segment used for comparison to the reference nucleotide sequence or reference amino acid sequence will comprise at least 6, 10, 15, or 20 contiguous nucleotides, or amino acid residues, and may be 30, 40, 50, 100, or more nucleotides or amino acid residues. Corrections for increased sequence identity associated with inclusion of gaps in the variant's nucleotide sequence or amino acid sequence can be made by assigning gap penalties. Methods of sequence alignment are known in the art.

In embodiments, the determination of percent identity or "homology" between two sequences is accomplished using a mathematical algorithm. For example, the percent identity of an amino acid sequence is determined using the Smith-Waterman homology search algorithm using an affine 6 gap search with a gap open penalty of 12 and a gap extension penalty of 2, BLOSUM matrix 62. The Smith-Waterman homology search algorithm is described in Smith and Waterman (1981) *Adv. Appl. Math* 2:482-489, herein incorporated by reference. In embodiments, the percent identity of a nucleotide sequence is determined using the Smith-Waterman homology search algorithm using a gap open penalty of 25 and a gap extension penalty of 5. Such a determination of sequence identity can be performed using, for example, the DeCypher Hardware Accelerator from TimeLogic.

As used herein, the term "homology" is used to compare two or more proteins by locating common structural characteristics and common spatial distribution of, for instance, beta strands, helices, and folds. Accordingly, homologous protein structures are defined by spatial analyses. Measuring structural homology involves computing the geometric—topological features of a space. One approach used to generate and analyze three-dimensional (3D) protein structures is homology modeling (also called comparative modeling or knowledge-based modeling) which works by finding similar sequences on the basis of the fact that 3D similarity reflects 2D similarity. Homologous structures do not imply sequence similarity as a necessary condition.

As used herein, the terms "subject" and "patient" are intended to include humans having a disease or a disorder, e.g., a cancerous tumor, diabetes or another disease or disorder described herein, or normal subjects.

As used herein, the term "titer" or "yield" refers to the amount of a fusion protein product (e.g., an insulin-Fc fusion protein described herein) resulting from the biosynthesis (e.g., in a mammalian cell, e.g., in a HEK293 cell or CHO cell) per volume of the cell culture. The amount of product may be determined at any step of the production process (e.g., before or after purification), but the yield or titer is always stated per volume of the original cell culture. As used herein, the term "product yield" or "total protein yield" refers to the total amount of insulin-Fc fusion protein expressed by cells and purified via at least one affinity chromatography step (e.g., Protein A or Protein G) and includes monomers of insulin-Fc fusion protein, homodimers of insulin-Fc fusion protein, and higher-order molecular aggregates of homodimers of insulin-Fc fusion protein. As used herein, the term "percent homodimer" or "% homodimer" refers to the proportion of a fusion protein product (e.g., an insulin-Fc fusion protein described herein) that is the desired homodimer. As used herein, the term "homodimer titer" refers to the product of the % homodimer and the total protein yield after Protein A purification step reported per volume of the cell culture.

As used herein, the terms "treat" or "treating" a subject having a disease or a disorder refer to subjecting the subject to a regimen, for example the administration of a fusion protein, such as a fusion protein described herein, such that at least one symptom of the disease or disorder is cured, healed, alleviated, relieved, altered, remedied, ameliorated, or improved. Treating includes administering an amount effective to alleviate, relieve, alter, remedy, ameliorate, improve, or affect the disease or disorder, or the symptoms of the disease or disorder. The treatment may inhibit deterioration or worsening of a symptom of a disease or disorder.

Fusion Protein Components and Structure

The present disclosure relates to a composition of a fusion protein (i.e., an insulin-Fc fusion protein) comprising an insulin polypeptide linked either directly or via a peptide linker to a species-specific Fc fragment, and its use to treat cancer in mammals. As used herein, the terms "fusion protein" and "insulin-Fc fusion protein" refer to a protein comprising more than one part, for example from different sources (different proteins, polypeptides, cells, etc.), that are covalently linked through peptide bonds. Insulin-Fc fusion proteins may be covalently linked by (i) connecting the genes that encode for each part into a single nucleic acid molecule and (ii) expressing in a host cell (e.g., HEK or CHO) the protein for which the nucleic acid molecule encodes as follows: (N-terminus)—insulin polypeptide—linker—Fc fragment—(C-terminus). The fully recombinant synthesis approach is preferred over methods in which the insulin polypeptide and Fc fragments are synthesized separately and then chemically conjugated. The chemical conjugation step and subsequent purification process increase the manufacturing complexity, reduce product yield, and increase cost.

As used herein, the term "dimer" refers to a protein or a fusion protein comprising two polypeptides linked covalently. In embodiments, two identical polypeptides are linked covalently (e.g., via disulfide bonds) forming a "homodimer" (diagrammatically represented in FIG. 1). Disulfide bonds are shown in FIG. 1; the total number of disulfide bonds in actuality may be greater or less than the number shown in FIG. 1. In embodiments, the homodimer is encoded by a single nucleic acid molecule, wherein the homodimer is made recombinantly inside a cell by first forming insulin-Fc fusion protein monomers and by then assembling two identical insulin-Fc fusion protein monomers into the homodimer upon further processing inside the cell.

As used herein, the terms "multimer," "multimeric," or "multimeric state" refer to non-covalent, associated forms of Fc fusion protein dimers that may be in equilibrium with Fc fusion protein dimers or may act as permanently aggregated versions of Fc fusion protein dimers (e.g., dimers of Fc fusion protein homodimers, trimers of Fc fusion protein homodimers, tetramers of Fc fusion protein homodimers, or higher order aggregates containing five or more Fc fusion protein homodimers). It may be expected that multimeric forms of Fc fusion proteins may have different physical, stability, or pharmacologic activities from that of the insulin-Fc fusion protein homodimers.

Insulin Polypeptide

In embodiments, the insulin-Fc fusion proteins described herein comprise an insulin polypeptide, e.g., an insulin or insulin analog. Insulin is a peptide hormone produced by β-cells in islets of Langerhans within the pancreas. Insulin functions by regulating the absorption of glucose from the blood. Upon a stimulus, such as increased protein and glucose levels, insulin is released from β-cells and binds to the insulin receptor, initiating a signal cascade that affects many aspects of mammalian metabolism. Disruption of this process is directly related to several diseases, notably diabetes, insulinoma, insulin resistance, metabolic syndromes, and polycystic ovary syndrome.

Insulin analogs of the present disclosure may be related to the structure of insulin yet contain one or more modifications. In some embodiments, the insulin analog comprises at least one amino acid substitution, deletion, addition, or chemical modification relative to insulin, which may impact a particular feature or characteristic of the insulin-Fc fusion protein configuration. For example, the modifications or alterations described herein may impact the structure, stability, pH sensitivity, bioactivity, or binding affinity of the insulin-Fc fusion protein configuration to a cell surface receptor (e.g., an insulin hormone receptor) relative to a reference standard.

The amino acid sequence of insulin is strongly conserved throughout evolution, particularly in vertebrates. For example, native canine and porcine insulins differ by only one amino acid from human insulin, native bovine insulin differs by only three amino acids from human insulin, and native feline insulin differs by just four amino acids from human insulin. As used herein, the terms "B-chain or B-chain analog", "C-peptide" or "C-chain", and "A-chain or A-chain analog" refer to the peptide segments of an insulin polypeptide as illustrated in FIG. 1. Insulin is a 51 amino acid hormone containing two peptide chains (i.e., a B-chain and an A-chain) connected via disulfide bonds (e.g., disulfide bonds formed by one or more B-chain cysteine side chain thiols and one or more A-chain cysteine side chain thiols). The A-chain of insulin is 21 amino acids in length and the B-chain of insulin is 30 amino acids in length. In the native form of insulin, the A-chain contains one intrachain disulfide bond formed by two A-chain cysteine side chain thiols.

As used herein, the term "insulin" or "insulin polypeptide" encompasses mature insulin, preproinsulin, proinsulin, and naturally occurring insulin, or analogs thereof. In embodiments, an insulin polypeptide can be a full-length insulin polypeptide or a fragment thereof. In embodiments, an insulin polypeptide can comprise one or more fragments from mature insulin, preproinsulin, proinsulin, or naturally occurring insulin.

Insulin is normally constructed as a N-terminus—B-chain:C-chain:A-chain—C-terminus polypeptide, wherein the C-chain is cleaved in order to make it bioactive. For reference purposes, the sequence of the entire human insulin molecule including the C-chain (i.e., human proinsulin) is shown below with the C-chain shown in bold-faced type:

(SEQ ID NO: 40)
FVNQHLCGSHLVEALYLVCGERGFFYTP

KTRREAEDLQVGQVELGGGPGAGSLQPL

ALEGSLQKRGIVEQCCTSICSLYQLENY

CN.

The transformation of the single-chain insulin polypeptide into a bioactive two-chain polypeptide is normally accomplished within the β-cells of the islets of Langerhans prior to glucose-stimulated insulin secretion by two endoproteases, Type I endoproteases, PC1 and PC3, that disrupt the C peptide-B chain connection and PC2, and a Type II endoprotease, that cleaves the C peptide-A chain bond at exactly the right sites. However, cell systems used for the biosynthesis of therapeutic molecules such as insulin (e.g., bacteria, yeast, and mammalian (e.g., HEK and CHO) cell systems) do not possess this pathway, and therefore the transformation must take place after expression and harvesting of the single chain polypeptide using chemical or enzymatic methods. Known techniques for cleaving the C-chain after expression and harvesting rely on first modifying the C-chain such that it terminates in a lysine just before the N-terminus of the A-chain. Then, using an enzyme selected from the trypsin or Lys-C families, which clips peptide bonds specifically at the C-termini of lysine residues, the single chain-insulin polypeptide is cleaved at the C-terminal lysine of the C-chain and at the C-terminal lysine at the 29th position from the N-terminus of the B-chain. In some cases, the resulting bioactive two-chain insulin is used without reattaching the clipped amino acid at the 30th position from the N-terminus of the B-chain, and in some cases the clipped amino acid at the 30th position from the N-terminus of the B-chain is added back to the molecule using an additional enzymatic method. Such a process works well with insulin because it contains only one lysine in its entire two chain polypeptide form.

Recombinant human insulin (which in the present application is herein referred to as "RHI") is a bioactive two-chain polypeptide comprising the B-chain of SEQ ID NO: 41: FVNQHLCGSHLVEALYLVCGERGFFYTPKT, and the A-chain of SEQ ID NO: 33: GIVEQCCTSICSLYQLENYCN connected by two disulfide bonds derived from cysteine residues (A7-B7 and A20-B19). A third disulfide is an intrachain disulfide bond derived from cysteine residues on the A-chain (A6-A11). This structure of RHI is well known in the art (see for example Brange, Jens, *Gelanics of Insulin: The Physico-Chemical and Pharmaceutical Aspects of Insulin and Insulin Preparations* (1987) Springer-Verlag Berlin Heidelberg, https://doi.org/10.1007/978-3-662-02526-0).

However, this process cannot be used on the insulin-Fc fusion proteins contained herein, because all known Fc fragments contain multiple lysine residues. The enzymatic cleavage process would, therefore, digest the Fc fragment into non-functional parts, thereby eliminating the ability of the Fc fragment to prolong the action of the insulin polypeptide in vivo. Therefore, an insulin-Fc fusion protein of the present invention must comprise an insulin polypeptide that does not require C-chain cleavage and is therefore bioactive in its single chain form.

A number of bioactive single chain insulin polypeptides have been described in the art. In all cases, the single chain insulin polypeptides contain C-chains of specific length and composition as well as A-chains and B-chains mutated at specific amino acid sites in order to achieve electrostatic balance, prevent aggregation, and enhance IR binding and/or downstream signaling to achieve bioactivity at levels comparable to that of the native two-chain insulin. Herein, the location of mutations on peptide segments are notated using the name of the segment (e.g., B-chain, C-chain, A-chain) and the number of the amino acid counting from the N-terminus of the segment. For example, the notation "B10" refers to the 10th amino acid from the N-terminus of the amino acid sequence of the B-chain. The notation "A8" refers to the 8th amino acid from the N-terminus of the A-chain. Furthermore, if an amino acid is mutated from its native form to a new amino acid at a particular location, the location is appended with the one letter amino acid code for the new amino acid. For example, B10D refers to an aspartic acid mutation at the 10th amino acid from the N-terminus of the amino acid sequence of the B-chain and A8H refers to a histidine mutation at the 8th amino acid from the N-terminus of the amino acid sequence of the A-chain.

In some embodiments, the insulin polypeptides of the present disclosure comprise insulin analogs. The insulin analogs may be closely related to the structure of insulin yet contain a modification (e.g., a structural modification) to enhance a certain functional aspect. In some embodiments, the insulin analog comprises a variant or mutant of insulin. In some embodiments, the insulin analog comprises at least one amino acid substitution, deletion, or addition relative to insulin.

In some embodiments, modifications to the sequence or structure of insulin or an insulin analog (e.g., an amino acid substitution, deletion, or addition, or a chemical modification) may impact a particular feature or characteristic of the insulin-Fc fusion protein (e.g., insulin-Fc fusion protein described herein). For example, the modifications or alterations described herein may impact the structure, stability, pH sensitivity, bioactivity, or binding affinity of the insulin-Fc fusion protein to a cell surface receptor (e.g., an insulin hormone receptor). In some embodiments, an amino acid substitution, addition, deletion, or a chemical modification relative to insulin may affect the activity of the insulin analog relative to a reference standard.

In embodiments, the insulin or insulin analog is a three-segment peptide comprising elements of a B-chain, a C-peptide, and an A-chain. In other embodiments, an insulin-Fc fusion protein described herein comprises an insulin polypeptide comprising a mutant insulin B-chain, C-peptide, and/or A-chain.

In embodiments, modifications to the sequence of the insulin or insulin analog (e.g., amino acid substitutions, deletions, or additions or chemical modifications) may be to either the B-chain of insulin, the C-peptide of insulin, the A-chain of insulin, or any combination thereof.

Insulin-Fc fusion proteins combine an insulin polypeptide with a human Fc region as illustrated in FIG. 1. These insulin-Fc fusion proteins are made biologically in mammalian cells as a single chain, in which the insulin molecule is connected between the A- and B-chains with a short peptide sequence, and the use of a human Fc region acts to prolong their action in vivo.

Fc Fragment

In embodiments, a fusion protein described herein comprises an Fc fragment, e.g., connected to an insulin polypeptide described herein.

The terms "Fc region," "Fc domain," "Fc polypeptide," or "Fc fragment" as used herein are used to define a C-terminal region of an immunoglobulin heavy chain. The Fc fragment, region, or domain may be a native sequence Fc region or a variant/mutant Fc region. Although the boundaries of the Fc region of an immunoglobulin heavy chain may vary, they generally comprise some or all of the hinge region of the heavy chain, the CH2 region of the heavy chain, and the CH3 region of the heavy chain. The hinge region of a human Fc fragment comprises amino acid sequences that connect the CH1 domain of the heavy chain to the CH2 region of the heavy chain and which contain one or more cysteines that form one or more interheavy chain disulfide bridges to form a homodimer of the Fc fusion protein from two identical but separate monomers of the Fc fusion protein. The hinge region may comprise all or part of a naturally occurring amino acid sequence or a non-naturally occurring amino acid sequence.

An Fc receptor (FcR) refers to a receptor that binds to an Fc fragment or the Fc region of an antibody. In embodiments, the FcR is a native sequence human FcR. In embodiments, the FcR is one which binds an Fc fragment or the Fc region of an IgG antibody (a gamma receptor) and includes without limitation, receptors of the FcγRI, FcγRIIa, FcγRIIb, and FcγRIII subclasses, including allelic variants and alternatively spliced forms of these receptors. "FcR" also includes the neonatal receptor, FcRn, which is responsible for the transfer of maternal IgGs to the fetus (Guyer et al., 1976 *J. Immunol.*, 117:587; and Kim et al., 1994, *J. Immunol.*, 24:249) and is also responsible for the prolonged in vivo elimination half-lives of antibodies and Fc-fusion proteins in vivo. In embodiments, an Fc fragment described herein is capable of binding to mammalian Fc(gamma) or Fc(Rn) receptors, e.g., human Fc(gamma) or human Fc(Rn) receptors.

In embodiments, the C-terminal lysine that is often found in native human IgG isotype Fc fragment amino acid sequences (i.e., the lysine that represents the last amino acid of the Fc fragment sequence) is omitted to prevent the accidental production of unwanted amino acid sequence variants during manufacturing (e.g., Fc fragments containing the C-terminal lysine becoming mixed with Fc fragments where the C-terminal lysine is omitted, which can occur during production of the desired protein within cells (Dick, L W., (2008) *Biotechnol Bioeng*. August 15; 100(6) pp 1132-43).

In embodiments, the Fc fragment comprises the Fc region, e.g., hinge region, CH2 domain, and CH3 domain (or a fragment thereof) of a human immunoglobulin (e.g., IgG1). In embodiments, the Fc fragment comprises the hinge region (or a fragment thereof) of a human IgG1. In embodiments, the Fc fragment comprises the Fc region, e.g., CH2 domain and CH3 domain (or a fragment thereof) of human IgG1.

In embodiments, the fragment of the Fc region of a human IgG1 comprises the following amino acid sequence:

```
                                      (SEQ ID NO: 15)
    DKTHTCPPCPAPELLGGPSVFLFPPKPKDTLM

ISRTPEVTCVVVDVSHEDPEVKFNWYVDGVEV

HNAKTKPREEQYNSTYRVVSVLTVLHQDWLNG

KEYKCKVSNKALPAPIEKTISKAKGQPREPQV

YTLPPSRDELTKNQVSLTCLVKGFYPSDIAVE

WESNGQPENNYKTTPPVLDSDGSFFLYSKLTV

DKSRWQQGNVFSCSVMHEALHNHYTQKSLSLS

PG.
```

Linker

In embodiments, a fusion protein described herein comprises a linker, e.g., between one or more domains of the polypeptide. For example, a fusion protein comprises a linker between the insulin polypeptide and the Fc fragment.

In some examples, the C-terminus of the insulin polypeptide is connected directly to the N-terminus of the Fc fragment (e.g., no linker or linker absent). In other examples, the successful construction of a recombinantly made insulin-Fc fusion protein requires a linker connecting the insulin polypeptide to the Fc fragment. In embodiments, insulin-Fc fusion protein configurations described herein comprise a peptide linker between the insulin polypeptide and the Fc fragment comprising amino acids (e.g., natural, or unnatural amino acids). In embodiments, the peptide linker can be encoded by a nucleic acid molecule, for example such that a single nucleic acid molecule can encode the various peptides within an insulin polypeptide as well as the peptide linker and the Fc fragment. The choice of peptide linker (for example, the length, composition, hydrophobicity, and secondary structure) could impact the manufacturability of the insulin-Fc fusion protein configuration (i.e., the homodimer titer), the chemical and enzymatic stability, the bioactivity, parameters that correlate with bioactivity (i.e., the FcRn assay EC50 value), and the immunogenicity of the insulin-Fc fusion protein (Chen, X., Zaro, J., Shen, W. C., *Adv Drug Deliv Rev.* 2013 Oct. 15; 65(10): 1357-1369).

In embodiments, the linker is a peptide. In embodiments, the peptide linker comprises amino acids (e.g., natural, or unnatural amino acids). In embodiments, the peptide linker can be encoded by a nucleic acid molecule, (e.g., such that a single nucleic acid molecule can encode the various peptides within an insulin polypeptide as well as the peptide linker as well as the Fc fragment).

In embodiments, the peptide linker comprises the amino acid sequence GGGGAGGGG (SEQ ID NO: 13) as listed in Table A. In embodiments, the peptide linker comprises the amino acid sequence GGGGGQGGGGQGGGGQGGGGG (SEQ ID NO: 14) as listed in Table A. In embodiments, the peptide linker comprises the amino acid sequence GGG-GAGGGGAGGGG (SEQ ID NO: 34) as listed in Table A. In embodiments, the peptide linker comprises the amino acid sequence GGGG (SEQ ID NO: 35) as listed in Table A. In other embodiments, there is no peptide linker as listed in Table A.

Fusion Proteins

Provided herein are fusion proteins, e.g., insulin-Fc fusion proteins. In embodiments, the fusion protein comprises an insulin polypeptide described herein, e.g., in the Insulin polypeptide section herein. In embodiments, the fusion protein comprises an Fc fragment, e.g., an Fc fragment described herein, e.g., in the Fc fragment section herein.

In embodiments, the fusion protein comprises a linker between the insulin polypeptide described, e.g., in the Insulin polypeptide section herein and the Fc fragment described, e.g., in the Fc fragment section herein. Exemplary linkers (e.g., peptide linkers) are described in greater detail in the Linker section herein.

In embodiments, the insulin polypeptide comprises domains in the following orientation from N- to C-termini: (N-terminus)—B-chain—C-peptide—A-chain—(C-terminus). The insulin polypeptide may be located at the N-terminus of the Fc domain.

In embodiments, the fusion protein comprises domains in the following orientation from N- to C-termini: (N-terminus)—insulin polypeptide—linker—Fc fragment—(C-terminus) (e.g., (N-terminus)—B-chain—C-peptide—A-chain—linker—Fc fragment—(C-terminus); or (N-terminus)—B-chain—C-peptide—A-chain—linker—Fc fragment—(C-terminus)) as illustrated in FIG. 1. In embodiments, the fusion protein, also referred to as the insulin-Fc fusion protein, is comprised of two identical insulin-Fc fusion proteins covalently bound together via one or more disulfide bonds (shown as dotted lines in FIG. 1; the total number of disulfide bonds in actuality may be greater or less than the number shown in FIG. 1). Each insulin-Fc fusion protein comprises a proinsulin-like insulin molecule containing an insulin B-chain and an insulin A-chain that are connected between the B-chain-C-terminal region and the A-chain-NH2 terminal region with a C-chain (gray line in FIG. 1), and the A-chain-C-terminal region and Fc-chain amino terminus with a linker, where the insulin-Fc fusion protein sequence terminates in the Fc-CH3 region-C-terminal region. Note that the B-chain and A-chain are also linked together via two disulfide bonds (dotted lines in FIG. 1). The A-chain also has an intramolecular disulfide bond (not shown in FIG. 1).

The Treatment of Cancer Tumors Through Prolonged Hypoglycemia

Cancer cells consume increased amounts of glucose compared to normal cells, metabolizing the glucose-derived pyruvate to lactate even in the presence of oxygen (the Warburg effect). While aerobic glycolysis is less efficient (in terms of adenosine triphosphate production) than mitochondrial oxidative phosphorylation that normal cells use to produce energy, it does lead to the increased generation of additional metabolites that benefit proliferating cells such as cancer cells. As the Warburg effect is associated with glucose uptake and utilization, it was envisioned that an ultra-long acting basal insulin for diabetes treatment that would effectively lower blood sugar for a prolonged period of time would be useful in treating cancer. Insulin-analog mutants that can bind and activate the insulin hormone receptor and take advantage of FcRn receptor recycling to prolong their action could accomplish this goal through prolonged interaction with insulin receptors present on cell surfaces to help arrest cancer cell growth and mitogenesis.

Insulin-Fc fusion proteins comprising mutations in the A- and B-chains as well as in the connecting peptide between the A- and B-chains, covalently linked through a peptide linker to an IgG Fc region (as illustrated in FIG. 1) were required to accomplish this goal. One variation of insulin-Fc fusion proteins was designed such that the compound could bind and activate the insulin hormone receptor and do so with an acceptably low insulin receptor affinity EC50 ratio as compared to the affinity of endogenous insulin, in addition to taking advantage of the FcRn receptor recycling to substantially increase the half-life of the compound in serum. Achieving these outcomes required modifications to the peptide sequence between the A- and B-chains, in addition to mutations in the A- and B-chains themselves. SEQ ID NO: 1, shown in FIG. 2, demonstrated acceptable potency and protracted blood glucose lowering activity in mice as shown in FIG. 6.

Figure 6:
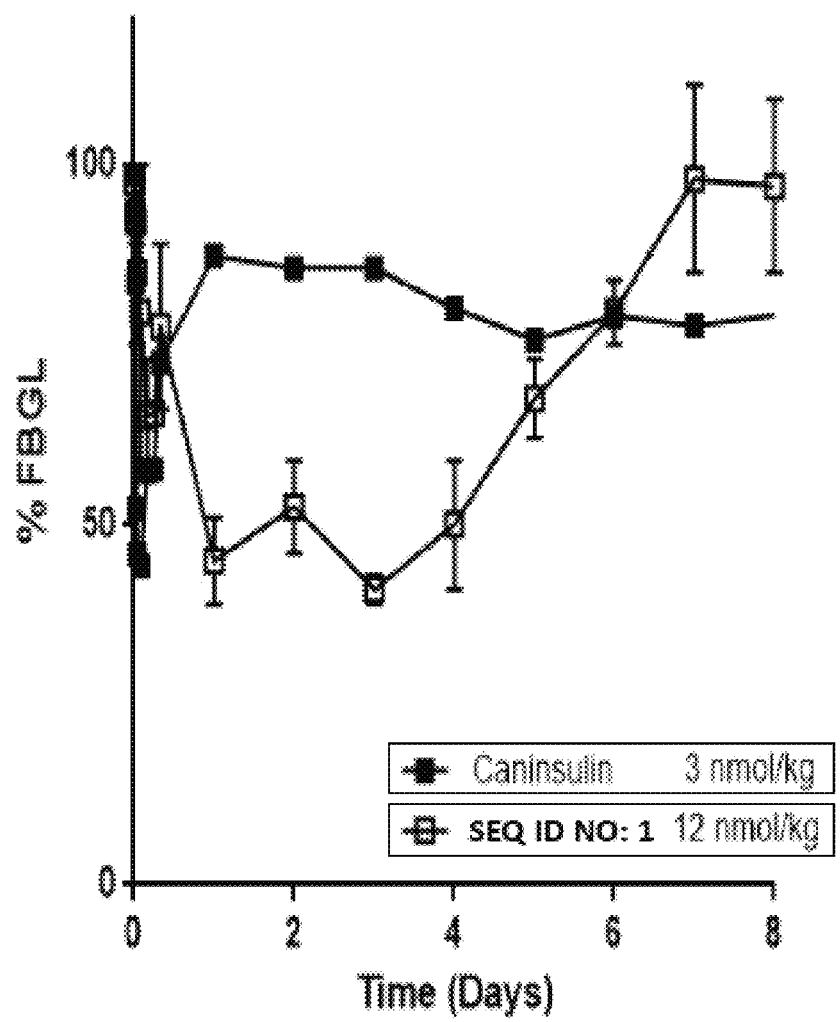
FIG. 6 shows the percent fasting blood glucose level for SEQ ID NO: 1 and porcine insulin NPH vehicle.

Unexpectedly, it was observed that even though the mice had blood glucose (BG) levels significantly lower than normal (as shown in FIG. 6 with a comparison to a porcine insulin NPH vehicle), they did not exhibit clinical signs of hypoglycemia such as lethargy, loss of balance, convulsions, or loss of consciousness even when fasted for prolonged periods of time. Given these unexpected results, it was hypothesized that the compound of SEQ ID NO: 1 may be able to slow cancerous tumor growth by inducing "managed hypoglycemia" thereby limiting the glucose available to cancer cells for aerobic glycolysis, while sparing the rest of the body.

Results shown in Example 9a, Example 9b, Example 10a and Example 10b, performed in HCT-116 xenograft models (HCT116 cells are used in a variety of biomedical studies involving colon cancer proliferation and corresponding inhibitors) in nude mice (as described in Example 9a and Example 9b) and with an in vivo model of a metastatic human melanoma cell line (WM266.4, as described in Example 10a and Example 10b) in nude mice demonstrated that SEQ ID NO: 1 was capable of slowing tumor growth compared to controls under both fasted and unfasted conditions. Animals treated with conventional NPH insulin showed no benefit with treatment under fasted conditions, even though similar fasting levels of hypoglycemia were observed in both NPH and SEQ ID NO: 1 after dosing, and higher doses of NPH were not feasible due to frequent incidences of life-threatening hypoglycemia in the mice. Unexpectedly, animals treated with SEQ ID NO: 1 without fasting still exhibited significant reduction in tumor growth rate. The data indicated that prolonged hypoglycemia was not the mechanism by which SEQ ID NO: 1 was inhibiting cancer cell growth.

Treatment of Cancer Tumors Through Decreasing Insulin-Like Growth Factor 1 Receptor (IGF1R)

The IGF1 receptor or IFG1R is a transmembrane receptor found on the surface of cells. Because the IGF1R is overexpressed in several tumor types and as a result of its impact on tumor survival and proliferation in preclinical studies, several anti-IGF1R therapies have been developed for clinical trials. While promising, these therapies have had limited success in the clinic, most likely due to the development of resistance through alternate signaling pathways.

Still further, it is known that treatment of some cancers with particular drugs (e.g., treatment of breast cancers with a drug such as Tamoxifen) can result in breast cancer cells with reduced or downregulated IFG1R. This downregulation of the IFG1R eventually allows the cancer cells to become resistant to the drug (e.g., drug induced resistance, or "Tamoxifen-resistant" cancers or tumors) through alternate signaling pathways similar to what has occurred in anti-IGF1R therapy approaches. This drug-induced resistance has been demonstrated in the laboratory with cancerous cell lines (e.g., breast cancer cell line MCF-7 and Tamoxifen resistant breast cancer cell line MCF-7 (also known as MCF-7 TamR).

The IGF1R is activated by a hormone called insulin-like growth factor 1 (IGF-1) and by a related hormone called insulin-like growth factor 2 (IGF-2). Ligand binding of IGF-1 and IGF-2 to the IGF1R on the surface of cells leads to autophosphorylation and activation of two distinct but overlapping pathways: PI3K-Akt and the MAPK. The PI3K pathway is a cascade which leads to phosphorylation and activation of Akt, a serine/threonine kinase, which regulates cellular metabolism through the translocation of the GLUT4 glucose transporter to the cell surface. The fully activated Akt mediates downstream responses including cell survival, growth, proliferation, cell migration and angiogenesis, by phosphorylating a range of intracellular proteins, regulating cell survival through inhibition of apoptosis, and making it important for tumor survival. Activation of the MAPK pathway causes the activation of ERK1/2, leading to increased cell proliferation, metastasis, and tumor growth.

Clinicians would like to treat certain cancers by decreasing the IGF1R present on tumors, based on the hypothesis that less IGF-1 and IGF-2 would be capable of binding the IFG1R and triggering the downstream cell proliferation and growth of the tumors. Approaches using anti-IGF1R antibody therapies have been tried in the clinic, many of which have advanced as far as Phase 3 clinical trials, but all programs have been discontinued due to the tumors building resistance over time. When IGF1R is downregulated in response to binding the therapeutically administered anti-IGF1R antibodies and internalization of the receptor-antibody complex, IGF-1 and IGF-2 serum concentrations increase as they are not being eliminated through the IGF1R as quickly. IGF-1 and IGF-2 are capable of activating the insulin receptor (IR) at high concentrations due to their structural similarity to insulin, resulting in binding and signaling through the IR. This undesirable activation of the IR/phosphorylated-Akt signals the tumor to continue proliferating. Thus IGF-2 signaling through the IR is a potential mechanism of resistance for IFG1R therapies.

One way to prevent IGF-2 signaling through the IR is to use anti-IR antibodies in combination with anti-IGF1R antibodies. However there have only been a limited number of clinical candidates targeting the IR due to anti-IR antibodies resulting in downregulation of the IR, which leads to decreased insulin binding leading to unwanted hyperglycemia and insulin resistance.

Another approach focuses on short interfering RNA (siRNA) or RNA interference (RNAi). A promoter system may be used to deliver and express siRNA targeting IGF1R to reduce its expression in cells. This downregulation of IGF1R results in significant inhibition of cancer cell growth in vitro and in vivo in rodents. However, this approach is also likely to suffer from upregulated IGF-1 and IGF-2 binding and activation of IR leading to tumor growth and unwanted hyperglycemia. A further approach is to use small molecule, tyrosine kinase inhibitors (TKIs) that simultaneously target both the IGF1R and IR systems without having to blockade the receptors themselves or reduce the receptor expression levels. However, because TKIs are small molecules, they lack specificity for IGF1R/IR and can therefore potentially disrupt other receptor systems, including those not involved in cancer cell metabolism, causing unwanted side effects and toxicity as a result. Furthermore, TKIs also lead to unwanted hyperglycemia due to disruption of the IR pathway for glucose homeostasis. These various approaches support the assertion that preparations that downregulate both the IGF1R and the IR without unwanted side effects or hypo/hyperglycemia risks would significantly inhibit cancer cell growth resulting in desirable anti-tumor efficacy.

Treatment of Cancer Tumors Through Downregulation of the Insulin Receptor (IR)

To examine the relationship between IR binding and activation in vitro and tumor volume reduction in vivo, the IR activity of the fusion proteins of SEQ ID NO: 1, SEQ ID NO: 18, SEQ ID NO: 20, SEQ ID NO: 22, SEQ ID NO: 24, SEQ ID NO: 26, and SEQ ID NO: 28, (all of which were constructed to maximize IR binding and activation) was compared to the IR activity of regular insulin (RHI) and SEQ ID NO: 3, which is another bivalent, long duration bioactive insulin-Fc fusion protein comprising different insulin sequence mutations as compared to SEQ ID NO: 1 (see FIG. 4 for a sequence comparison). Testing according to the protocol in Example 6, as illustrated in Table 5 demonstrated that SEQ ID NO: 3, SEQ ID NO: 26 and SEQ ID NO: 28 all had significantly lower IR affinity compared to SEQ ID NO: 1, SEQ ID NO: 18, SEQ ID NO: 20, SEQ ID NO: 22, SEQ ID NO: 24 and RHI.

When tested according to the protocol of Example 7a and Example 7b, SEQ ID NO: 1 and RHI caused substantial IR downregulation in HCT-116 cells compared to SEQ ID NO: 3, and unexpectedly, SEQ ID NO: 1 caused observably more downregulation that RHI at every concentration tested, suggesting that its bivalent homodimer structure, unique insulin mutations, and/or Fc component differentiate its behavior at the receptor level. Furthermore, SEQ ID NO: 1 induced lower levels of Akt phosphorylation than RHI at every concentration tested. Correlation of this data with the IR binding in vitro suggests that strong IR binding was necessary for receptor downregulation. The effects of both SEQ ID NO: 1 and RHI on the MAPK pathway were much more muted, with almost no change in phosphor-ERK1/2 expression after 72 hours of treatment.

Figure 5:
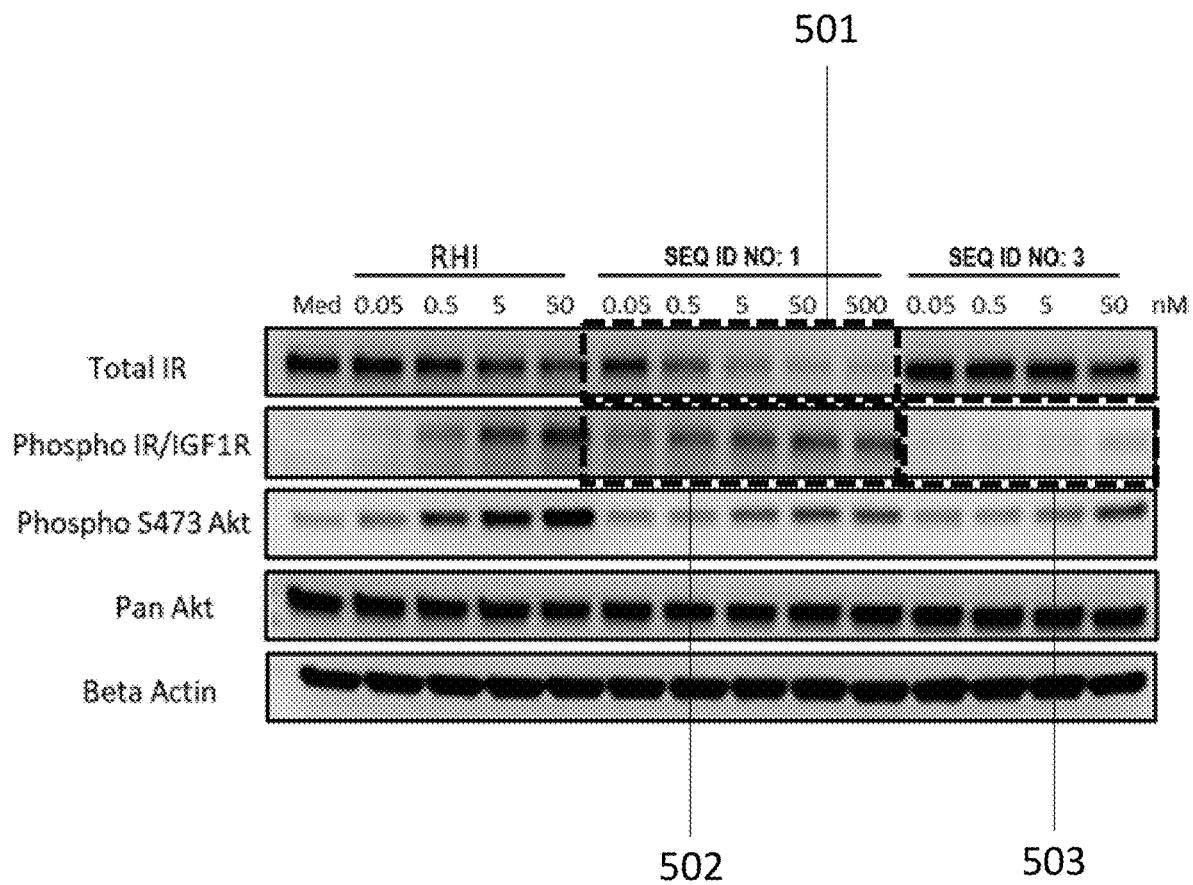
FIG. 5 shows Western Blot images of HCT-116 bearing nude mice treated in vitro with medium only, RHI, SEQ ID NO: 1 or SEQ ID NO: 3 at concentrations between 0.05 and 500 nM.

The preliminary data indicate that compared to insulin, SEQ ID NO: 1 slightly decreases activation of the PI3K pathway, which plays an important role in cancer cell metabolism and survival. However, unlike TKIs and anti-IR antibodies, SEQ ID NO: 1 is not an antagonist. It allows enough signaling through this pathway to regulate blood glucose levels, which is shown in FIG. 5 for Phospho 5473 Akt, which shows retained activation of the insulin receptor pathway even when the IR is being downregulated. Thus, SEQ ID NO: 1 is unique among IR targeting molecules in that it can inhibit tumor growth without causing hyperglycemia or insulin resistance. Thus, we hypothesize that the in vivo anti-tumor efficacy observed thus far with SEQ ID NO: 1 (and, conversely, not with insulin NPH or SEQ ID NO: 3) are likely related to one or more of the following effects on tumor cells: (i) downregulation of IR, (ii) downregulation of IGF1R, (iii) lower activation of the Akt pathway (e.g. less phosphorylated Akt in the presence of SEQ ID NO: 1), (iv) downregulation of IR in combination with additional therapies that separately target downregulation of IGF1R, or (v) downregulation of IR in tumors that have low levels of IGF1R expression.

In embodiments, the insulin polypeptide of the fusion protein comprises the amino acid sequence of SEQ ID NO: 6 or the amino acid sequence of SEQ ID NO: 37. The insulin polypeptide of SEQ ID NO: 6 and the insulin polypeptide of SEQ ID NO: 37 include mutations in the B-chain (specifically, B10 is mutated to aspartic acid (D)) and in the A-chain (specifically, A8 is mutated to histidine (H)):

```
                                          (SEQ ID NO: 6)
FVNQHLCGSDLVEALALVCGERGFFYTDPTG

GGPRRGIVEQCCHSICSLYQLENYCN;

(SEQ ID NO: 37)
FVNQHLCGSDLVEALALVCGERGFFYTDPTG

GGPRRGIVEQCCHSICSLYQLENYC.
```

In embodiments, the insulin polypeptide of the fusion protein comprises the amino acid sequence of SEQ ID NO: 36 or the amino acid sequence of SEQ ID NO: 38 or the amino acid sequence of SEQ ID NO: 39. The insulin polypeptides of SEQ ID NO: 36 and SEQ ID NO: 39 do not include a mutation in the B-chain at B10 (specifically, B10 is native as histidine(H)) or in the A-chain at A8 (specifically, A8 is native threonine (T)):

```
                                         (SEQ ID NO: 36)
FVNQHLCGSHLVEALELVCGERGFHYGGGGGG

SGGGGGIVEQCCTSTCSLDQLENYC;
and (SEQ ID NO: 39)
FVNQHLCGSHLVEALALVCGERGFFYTPKGGGPR

RGIVEQCCTSICSLYQLENYCN.
```

The insulin polypeptide of SEQ ID NO: 38 does include a mutation in the B-chain at B10 (specifically, B10 is mutated to aspartic acid (D)) however it does not include a mutation in in the A-chain at A8 (specifically, A8 is native threonine (T)):

```
                                         (SEQ ID NO: 38)
FVNQHLCGSHLVEALALVCGERGFFYTDPTGGGPR

RGIVEQCCHSICSLYQLENYCN.
```

In embodiments, the B-chain of the fusion protein comprises the amino acid sequence FVNQHLCGSDLVEALA-LVCGERGFFYTDPT (SEQ ID NO: 7) as listed in Table A, which includes the B10 mutation to aspartic acid (D).

In embodiments, the B-chain of the fusion protein comprises the amino acid sequence FVNQHLCGSHLVEALA-LVCGERGFFYTDPT (SEQ ID NO: 30) as listed in Table A, which does not include the B10 mutation to aspartic acid (D).

In embodiments, the B-chain of the fusion protein comprises the amino acid sequence FVNQHLCGSHLVEALA-LVCGERGFFYTPK (SEQ ID NO: 31) as listed in Table A, which does not include the B10 mutation to aspartic acid (D).

In embodiments, the C-chain peptide of the fusion protein comprises the amino acid sequence GGGPRR (SEQ ID NO: 9) as listed in Table A.

In embodiments, the A-chain of the fusion protein comprises the amino acid sequence of SEQ ID NO: 11 or the amino acid sequence of SEQ ID NO: 32, as listed in Table A, which include the A8 mutation to histidine (H):

```
                                         (SEQ ID NO: 11)
GIVEQCCHSICSLYQLENYCN;

(SEQ ID NO: 32)
GIVEQCCHSICSLYQLENYC.
```

In embodiments, the A-chain of the fusion protein comprises the amino acid sequence of SEQ ID NO: 33, as listed in Table A, which does not include the A8 mutation (specifically, A8 is native threonine (T)):

```
                                         (SEQ ID NO: 33)
GIVEQCCTSICSLYQLENYCN.
```

The insulin polypeptide of the fusion protein of SEQ ID NO: 3 (the insulin polypeptide is given in SEQ ID NO: 36), in contrast, does not include mutations in the B-chain (specifically, the B10 is not mutated to aspartic acid (D)) and in the A-chain (specifically, A8 is not mutated to histidine (H)), with these amino acids maintaining their native state (B10H, A8T):

```
                                         (SEQ ID NO: 36)
FVNQHLCGSHLVEALELVCGERGFHYGGGGGGS

GGGGGIVEQCCTSTCSLDQLENYC.
```

Unexpectedly, the B10D and A8H mutations on the B-chain and A-chain respectively of the insulin polypeptide are necessary mutations to achieve an insulin receptor binding affinity that is high enough to achieve insulin receptor downregulation and the proper glycemic control without hyperglycemia or hypoglycemia in vivo. In embodiments, the required necessary insulin receptor binding affinity is achieved when the fusion protein achieves an IR binding IC50 ratio relative to RHI of less than 20, as described in detail in Example 6.

Exemplary fusion proteins and their domains and sequences are shown in Table A.

The full-length sequences of fusion proteins of the present technology and their corresponding cDNA sequences are provided below:

```
SEQ ID NO: 1:
FVNQHLCGSDLVEALALVCGERGFFYTDPTGGGPR

RGIVEQCCHSICSLYQLENYCNGGGGAGGGGDKTH
```

-continued
TCPPCPAPELLGGPSVFLFPPKPKDTLMISRTPEV

TCVVVDVSHEDPEVKFNWYVDGVEVHNAKTKPREE

QYNSTYRVVSVLTVLHQDWLNGKEYKCKVSNKALP

APIEKTISKAKGQPREPQVYTLPPSRDELTKNQVS

LTCLVKGFYPSDIAVEWESNGQPENNYKTTPPVLD

SDGSFFLYSKLTVDKSRWQQGNVFSCSVMHEALHN

HYTQKSLSLSPG

SEQ ID NO: 2 (cDNA sequence of SEQ ID NO: 1):
ATGGAATGGAGCTGGGTCTTTCTCTTCTTCCTGTC

AGTAACGACTGGTGTCCACTCCTTCGTGAACCAGC

ACCTGTGCGGCTCCGACCTGGTGGAAGCTCTGGCT

CTCGTGTGCGGCGAGCGGGGCTTCTTCTACACCGA

TCCCACTGGAGGCGGTCCACGCAGAGGCATCGTGG

AACAGTGCTGCCACTCCATCTGCTCCCTGTACCAG

CTGGAAAACTACTGCAATGGCGGAGGTGGTGCAGG

AGGCGGTGGAGACAAAACTCACACATGCCCACCGT

GCCCAGCACCTGAACTCCTGGGGGACCGTCAGTC

TTCCTCTTCCCCCCAAAACCCAAGGACACCCTCAT

GATCTCCCGGACCCCTGAGGTCACATGCGTGGTGG

TGGACGTGAGCCACGAAGACCCTGAGGTCAAGTTC

AACTGGTACGTGGACGGCGTGGAGGTGCATAATGC

CAAGACAAAGCCGCGGGAGGAGCAGTACAACAGCA

CGTACCGTGTGGTCAGCGTCCTCACCGTCCTGCAC

CAGGACTGGCTGAATGGCAAGGAGTACAAGTGCAA

GGTCTCCAACAAAGCCCTCCCAGCCCCATCGAGA

AAACCATCTCCAAAGCCAAAGGGCAGCCCCGAGAA

CCACAGGTGTACACCCTGCCCCCATCCCGGGATGA

GCTGACCAAGAACCAGGTCAGCCTGACCTGCCTGG

TCAAAGGCTTCTATCCCAGCGACATCGCCGTGGAG

TGGGAGAGCAATGGGCAGCCGGAGAACAACTACAA

GACCACGCCTCCCGTGCTGGACTCCGACGGCTCCT

TCTTCCTCTACAGCAAGCTCACCGTGGACAAGAGC

AGGTGGCAGCAGGGGAACGTCTTCTCATGCTCCGT

GATGCATGAGGCTCTGCACAACCACTACACGCAGA

AGAGCCTCTCCCTGTCTCCGGGTTAG

SEQ ID NO: 3:
FVNQHLCGSHLVEALELVCGERGFHYGGGGGSGG

GGIVEQCCTSTCSLDQLENYCGGGGGQGGGGQGG

GGQGGGGDKTHTCPPCPAPELLGGPSVFLFPPKP

KDTLMISRTPEVTCVVVDVSHEDPEVKFNWYVDGV

-continued
EVHNAKTKPREEQYNSTYRVVSVLTVLHQDWLNGK

EYKCKVSNKALPAPIEKTISKAKGQPREPQVYTLP

PSRDELTKNQVSLTCLVKGFYPSDIAVEWESNGQP

ENNYKTTPPVLDSDGSFFLYSKLTVDKSRWQQGNV

FSCSVMHEALHNHYTQKSLSLSPG

SEQ ID NO: 4 (cDNA sequence of SEQ ID NO: 3):
ATGGAATGGAGCTGGGTCTTTCTCTTCTTCCTGTC

AGTAACGACTGGTGTCCACTCCTTCGTGAACCAGC

ACCTGTGCGGCTCCCACCTGGTGGAAGCTCTGGAA

CTCGTGTGCGGCGAGCGGGGCTTCCACTACGGGGG

TGGCGGAGGAGGTTCTGGTGGCGGCGGAGGCATCG

TGGAACAGTGCTGCACCTCCACCTGCTCCCTGGAC

CAGCTGGAAAACTACTGCGGTGGCGGAGGTGGTCA

AGGAGGCGGTGGACAGGGTGGAGGTGGGCAGGGAG

GAGGCGGGGGAGACAAAACTCACACATGCCCACCG

TGCCCAGCACCTGAACTCCTGGGGGGACCGTCAGT

CTTCCTCTTCCCCCCAAAACCCAAGGACACCCTCA

TGATCTCCCGGACCCCTGAGGTCACATGCGTGGTG

GTGGACGTGAGCCACGAAGACCCTGAGGTCAAGTT

CAACTGGTACGTGGACGGCGTGGAGGTGCATAATG

CCAAGACAAAGCCGCGGGAGGAGCAGTACAACAGC

ACGTACCGTGTGGTCAGCGTCCTCACCGTCCTGCA

CCAGGACTGGCTGAATGGCAAGGAGTACAAGTGCA

AGGTCTCCAACAAAGCCCTCCCAGCCCCCATCGAG

AAAACCATCTCCAAAGCCAAAGGGCAGCCCCGAGA

ACCACAGGTGTACACCCTGCCCCCATCCCGGGATG

AGCTGACCAAGAACCAGGTCAGCCTGACCTGCCTG

GTCAAAGGCTTCTATCCCAGCGACATCGCCGTGGA

GTGGGAGAGCAATGGGCAGCCGGAGAACAACTACA

AGACCACGCCTCCCGTGCTGGACTCCGACGGCTCC

TTCTTCCTCTACAGCAAGCTCACCGTGGACAAGAG

CAGGTGGCAGCAGGGGAACGTCTTCTCATGCTCCG

TGATGCATGAGGCTCTGCACAACCACTACACGCAG

AAGAGCCTCTCCCTGTCTCCGGGTTAG

SEQ ID NO: 18:
FVNQHLCGSDLVEALALVCGERGFFYTDPTGGGPR

RGIVEQCCHSICSLYQLENYCNGGGGAGGGGAGGG

GDKTHTCPPCPAPELLGGPSVFLFPPKPKDTLMIS

RTPEVTCVVVDVSHEDPEVKFNWYVDGVEVHNAKT

KPREEQYNSTYRVVSVLTVLHQDWLNGKEYKCKVS

NKALPAPIEKTISKAKGQPREPQVYTLPPSRDE

LTKNQVSLTCLVKGFYPSDIAVEWESNGQPENNYK

TTPPVLDSDGSFFLYSKLTVDKSRWQQGNVFSCSV

MHEALHNHYTQKSLSLSPG

SEQ ID NO: 19 (cDNA sequence of SEQ ID NO: 18):
ATGGAATGGAGCTGGGTCTTTCTCTTCTTCCTGTC

AGTAACGACTGGTGTCCACTCCTTCGTGAACCAGC

ACCTGTGCGGCTCCGACCTGGTGGAAGCTCTGGCT

CTCGTGTGCGGCGAGCGGGGCTTCTTCTACACCGA

TCCCACTGGAGGCGGTCCACGCAGAGGCATCGTGG

AACAGTGCTGCCACTCCATCTGCTCCCTGTACCAG

CTGGAAAACTACTGCAATGGTGGCGGAGGAGCTGG

CGGAGGTGGTGCAGGAGGCGGTGGAGACAAAACTC

ACACATGCCCACCGTGCCCAGCACCTGAACTCCTG

GGGGGACCGTCAGTCTTCCTCTTCCCCCCAAAACC

CAAGGACACCCTCATGATCTCCCGGACCCCTGAGG

TCACATGCGTGGTGGTGGACGTGAGCCACGAAGAC

CCTGAGGTCAAGTTCAACTGGTACGTGGACGGCGT

GGAGGTGCATAATGCCAAGACAAAGCCGCGGGAGG

AGCAGTACAACAGCACGTACCGTGTGGTCAGCGTC

CTCACCGTCCTGCACCAGGACTGGCTGAATGGCAA

GGAGTACAAGTGCAAGGTCTCCAACAAAGCCCTCC

CAGCCCCCATCGAGAAAACCATCTCCAAAGCCAAA

GGGCAGCCCCGAGAACCACAGGTGTACACCCTGCC

CCCATCCCGGGATGAGCTGACCAAGAACCAGGTCA

GCCTGACCTGCCTGGTCAAAGGCTTCTATCCCAGC

GACATCGCCGTGGAGTGGGAGAGCAATGGGCAGCC

GGAGAACAACTACAAGACCACGCCTCCCGTGCTGG

ACTCCGACGGCTCCTTCTTCCTCTACAGCAAGCTC

ACCGTGGACAAGAGCAGGTGGCAGCAGGGGAACGT

CTTCTCATGCTCCGTGATGCATGAGGCTCTGCACA

ACCACTACACGCAGAAGAGCCTCTCCCTGTCTCCG

GGTTAG

SEQ ID NO: 20:
FVNQHLCGSDLVEALALVCGERGFFYTDPTGGGPR

RGIVEQCCHSICSLYQLENYCGGGAGGGGDKTHT

CPPCPAPELLGGPSVFLFPPKPKDTLMISRTPEVT

CVVVDVSHEDPEVKFNWYVDGVEVHNAKTKPREEQ

YNSTYRVVSVLTVLHQDWLNGKEYKCKVSNKALPA

PIEKTISKAKGQPREPQVYTLPPSRDELTKNQVSL

TCLVKGFYPSDIAVEWESNGQPENNYKTTPPVLD

SDGSFFLYSKLTVDKSRWQQGNVFSCSVMHEALH

NHYTQKSLSLSPG

SEQ ID NO: 21 (cDNA sequence of SEQ ID NO: 20):
ATGGAATGGAGCTGGGTCTTTCTCTTCTTCCTGTC

AGTAACGACTGGTGTCCACTCCTTCGTGAACCAGC

ACCTGTGCGGCTCCGACCTGGTGGAAGCTCTGGCT

CTCGTGTGCGGCGAGCGGGGCTTCTTCTACACCGA

TCCCACTGGAGGCGGTCCACGCAGAGGCATCGTGG

AACAGTGCTGCCACTCCATCTGCTCCCTGTACCAG

CTGGAAAACTACTGCGGCGGAGGTGGTGCAGGAGG

CGGTGGAGACAAAACTCACACATGCCCACCGTGCC

CAGCACCTGAACTCCTGGGGGGACCGTCAGTCTTC

CTCTTCCCCCCAAAACCCAAGGACACCCTCATGAT

CTCCCGGACCCCTGAGGTCACATGCGTGGTGGTGG

ACGTGAGCCACGAAGACCCTGAGGTCAAGTTCAAC

TGGTACGTGGACGGCGTGGAGGTGCATAATGCCAA

GACAAAGCCGCGGGAGGAGCAGTACAACAGCACGT

ACCGTGTGGTCAGCGTCCTCACCGTCCTGCACCAG

GACTGGCTGAATGGCAAGGAGTACAAGTGCAAGGT

CTCCAACAAAGCCCTCCCAGCCCCCATCGAGAAAA

CCATCTCCAAAGCCAAAGGGCAGCCCCGAGAACCA

CAGGTGTACACCCTGCCCCCATCCCGGGATGAGCT

GACCAAGAACCAGGTCAGCCTGACCTGCCTGGTCA

AAGGCTTCTATCCCAGCGACATCGCCGTGGAGTGG

GAGAGCAATGGGCAGCCGGAGAACAACTACAAGAC

CACGCCTCCCGTGCTGGACTCCGACGGCTCCTTCT

TCCTCTACAGCAAGCTCACCGTGGACAAGAGCAGG

TGGCAGCAGGGGAACGTCTTCTCATGCTCCGTGAT

GCATGAGGCTCTGCACAACCACTACACGCAGAAGA

GCCTCTCCCTGTCTCCGGGTTAG

SEQ ID NO: 22
FVNQHLCGSDLVEALALVCGERGFFYTDPTGGGPR

RGIVEQCCHSICSLYQLENYCNGGGGDKTHTCPPC

PAPELLGGPSVFLFPPKPKDTLMISRTPEVTCVVV

DVSHEDPEVKFNWYVDGVEVHNAKTKPREEQYNST

YRVVSVLTVLHQDWLNGKEYKCKVSNKALPAPIEK

TISKAKGQPREPQVYTLPPSRDELTKNQVSLTCLV

KGFYPSDIAVEWESNGQPENNYKTTPPVLDSDGSF

FLYSKLTVDKSRWQQGNVFSCSVMHEALHNHYTQK

SLSLSPG

SEQ ID NO: 23 (cDNA sequence of SEQ ID NO: 22):
ATGGAATGGAGCTGGGTCTTTCTCTTCTTCCTGTC

AGTAACGACTGGTGTCCACTCCTTCGTGAACCAGC

ACCTGTGCGGCTCCGACCTGGTGGAAGCTCTGGCT

CTCGTGTGCGGCGAGCGGGGCTTCTTCTACACCGA

TCCCACTGGAGGCGGTCCACGCAGAGGCATCGTGG

AACAGTGCTGCCACTCCATCTGCTCCCTGTACCAG

CTGGAAAACTACTGCAATGGAGGCGGTGGAGACAA

AACTCACACATGCCCACCGTGCCCAGCACCTGAAC

TCCTGGGGGACCGTCAGTCTTCCTCTTCCCCCCA

AAACCCAAGGACACCCTCATGATCTCCCGGACCCC

TGAGGTCACATGCGTGGTGGTGGACGTGAGCCACG

AAGACCCTGAGGTCAAGTTCAACTGGTACGTGGAC

GGCGTGGAGGTGCATAATGCCAAGACAAAGCCGCG

GGAGGAGCAGTACAACAGCACGTACCGTGTGGTCA

GCGTCCTCACCGTCCTGCACCAGGACTGGCTGAAT

GGCAAGGAGTACAAGTGCAAGGTCTCCAACAAAGC

CCTCCCAGCCCCCATCGAGAAAACCATCTCCAAAG

CCAAAGGGCAGCCCCGAGAACCACAGGTGTACACC

CTGCCCCCATCCCGGGATGAGCTGACCAAGAACCA

GGTCAGCCTGACCTGCCTGGTCAAAGGCTTCTATC

CCAGCGACATCGCCGTGGAGTGGGAGAGCAATGGG

CAGCCGGAGAACAACTACAAGACCACGCCTCCCGT

GCTGGACTCCGACGGCTCCTTCTTCCTCTACAGCA

AGCTCACCGTGGACAAGAGCAGGTGGCAGCAGGGG

AACGTCTTCTCATGCTCCGTGATGCATGAGGCTCT

GCACAACCACTACACGCAGAAGAGCCTCTCCCTGT

CTCCGGGTTAG

SEQ ID NO: 24:
FVNQHLCGSDLVEALALVCGERGFFYTDPTGGGPR

RGIVEQCCHSICSLYQLENYCNDKTHTCPPCPAPE

LLGGPSVFLFPPKPKDTLMISRTPEVTCVVVDVSH

EDPEVKFNWYVDGVEVHNAKTKPREEQYNSTYRVV

SVLTVLHQDWLNGKEYKCKVSNKALPAPIEKTISK

AKGQPREPQVYTLPPSRDELTKNQVSLTCLVKGFY

PSDIAVEWESNGQPENNYKTTPPVLDSDGSFFLYS

KLTVDKSRWQQGNVFSCSVMHEALHNHYTQKSLSL

SPG

SEQ ID NO: 25 (cDNA sequence of SEQ ID NO: 24):
ATGGAATGGAGCTGGGTCTTTCTCTTCTTCCTGTC

AGTAACGACTGGTGTCCACTCCTTCGTGAACCAGC

ACCTGTGCGGCTCCGACCTGGTGGAAGCTCTGGCT

CTCGTGTGCGGCGAGCGGGGCTTCTTCTACACCGA

TCCCACTGGAGGCGGTCCACGCAGAGGCATCGTGG

AACAGTGCTGCCACTCCATCTGCTCCCTGTACCAG

CTGGAAAACTACTGCAATGACAAAACTCACACATG

CCCACCGTGCCCAGCACCTGAACTCCTGGGGGGAC

CGTCAGTCTTCCTCTTCCCCCCAAAACCCAAGGAC

ACCCTCATGATCTCCCGGACCCCTGAGGTCACATG

CGTGGTGGTGGACGTGAGCCACGAAGACCCTGAGG

TCAAGTTCAACTGGTACGTGGACGGCGTGGAGGTG

CATAATGCCAAGACAAAGCCGCGGGAGGAGCAGTA

CAACAGCACGTACCGTGTGGTCAGCGTCCTCACCG

TCCTGCACCAGGACTGGCTGAATGGCAAGGAGTAC

AAGTGCAAGGTCTCCAACAAAGCCCTCCCAGCCCC

CATCGAGAAAACCATCTCCAAAGCCAAAGGGCAGC

CCCGAGAACCACAGGTGTACACCCTGCCCCCATCC

CGGGATGAGCTGACCAAGAACCAGGTCAGCCTGAC

CTGCCTGGTCAAAGGCTTCTATCCCAGCGACATCG

CCGTGGAGTGGGAGAGCAATGGGCAGCCGGAGAAC

AACTACAAGACCACGCCTCCCGTGCTGGACTCCGA

CGGCTCCTTCTTCCTCTACAGCAAGCTCACCGTGG

ACAAGAGCAGGTGGCAGCAGGGGAACGTCTTCTCA

TGCTCCGTGATGCATGAGGCTCTGCACAACCACTA

CACGCAGAAGAGCCTCTCCCTGTCTCCGGGTTAG

SEQ ID NO: 26:
FVNQHLCGSHLVEALALVCGERGFFYTDPTGGGPR

RGIVEQCCHSICSLYQLENYCNGGGGAGGGGDKTH

TCPPCPAPELLGGPSVFLFPPKPKDTLMISRTPEV

TCVVVDVSHEDPEVKFNWYVDGVEVHNAKTKPREE

QYNSTYRVVSVLTVLHQDWLNGKEYKCKVSNKALP

APIEKTISKAKGQPREPQVYTLPPSRDELTKNQVS

LTCLVKGFYPSDIAVEWESNGQPENNYKTTPPVLD

SDGSFFLYSKLTVDKSRWQQGNVFSCSVMHEALHN

HYTQKSLSLSPG

SEQ ID NO: 27 (cDNA sequence of SEQ ID NO: 26):
ATGGAATGGAGCTGGGTCTTTCTCTTCTTCCTGTC

AGTAACGACTGGTGTCCACTCCTTCGTGAACCAGC

ACCTGTGCGGCTCCCACCTGGTGGAAGCTCTGGCT

CTCGTGTGCGGCGAGCGGGGCTTCTTCTACACCGA

TCCCACTGGAGGCGGTCCACGCAGAGGCATCGTGG

AACAGTGCTGCCACTCCATCTGCTCCCTGTACCAG

CTGGAAAACTACTGCAATGGCGGAGGTGGTGCAGG

AGGCGGTGGAGACAAAACTCACACATGCCCACCGT

GCCCAGCACCTGAACTCCTGGGGGGACCGTCAGTC

TTCCTCTTCCCCCCAAAACCCAAGGACACCCTCAT

GATCTCCCGGACCCCTGAGGTCACATGCGTGGTGG

TGGACGTGAGCCACGAAGACCCTGAGGTCAAGTTC

AACTGGTACGTGGACGGCGTGGAGGTGCATAATGC

CAAGACAAAGCCGCGGGAGGAGCAGTACAACAGCA

CGTACCGTGTGGTCAGCGTCCTCACCGTCCTGCAC

CAGGACTGGCTGAATGGCAAGGAGTACAAGTGCAA

GGTCTCCAACAAAGCCCTCCCAGCCCCCATCGAGA

AAACCATCTCCAAAGCCAAAGGGCAGCCCCGAGAA

CCACAGGTGTACACCCTGCCCCCATCCCGGGATGA

GCTGACCAAGAACCAGGTCAGCCTGACCTGCCTGG

TCAAAGGCTTCTATCCCAGCGACATCGCCGTGGAG

TGGGAGAGCAATGGGCAGCCGGAGAACAACTACAA

GACCACGCCTCCCGTGCTGGACTCCGACGGCTCCT

TCTTCCTCTACAGCAAGCTCACCGTGGACAAGAGC

AGGTGGCAGCAGGGGAACGTCTTCTCATGCTCCGT

GATGCATGAGGCTCTGCACAACCACTACACGCAGA

AGAGCCTCTCCCTGTCTCCGGGTTAG

SEQ ID NO: 28:
FVNQHLCGSHLVEALALVCGERGFFYTPKGGGPRR

GIVEQCCTSICSLYQLENYCNGGGGAGGGGDKTHT

CPPCPAPELLGGPSVFLFPPKPKDTLMISRTPEVT

CVVVDVSHEDPEVKFNWYVDGVEVHNAKTKPREEQ

YNSTYRVVSVLTVLHQDWLNGKEYKCKVSNKALPA

PIEKTISKAKGQPREPQVYTLPPSRDELTKN

QVSLTCLVKGFYPSDIAVEWESNGQPENNYKTTPP

VLDSDGSFFLYSKLTVDKSRWQQGNVFSCSVMHEA

LHNHYTQKSLSLSPG

SEQ ID NO: 29 (cDNA sequence of SEQ ID NO: 28):
ATGGAATGGAGCTGGGTCTTTCTCTTCTTCCTGTC

AGTAACGACTGGTGTCCACTCCTTCGTGAACCAGC

ACCTGTGCGGCTCCCACCTGGTGGAAGCTCTGGCT

CTCGTGTGCGGCGAGCGGGGCTTCTTCTACACCCC

CAAGGGAGGCGGTCCACGCAGAGGCATCGTGGAAC

AGTGCTGCACCTCCATCTGCTCCCTGTACCAGCTG

GAAAACTACTGCAATGGCGGAGGTGGTGCAGGAGG

CGGTGGAGACAAAACTCACACATGCCCACCGTGCC

CAGCACCTGAACTCCTGGGGGACCGTCAGTCTTC

CTCTTCCCCCCAAAACCCAAGGACACCCTCATGAT

CTCCCGGACCCCTGAGGTCACATGCGTGGTGGTGG

ACGTGAGCCACGAAGACCCTGAGGTCAAGTTCAAC

TGGTACGTGGACGGCGTGGAGGTGCATAATGCCAA

GACAAAGCCGCGGGAGGAGCAGTACAACAGCACGT

ACCGTGTGGTCAGCGTCCTCACCGTCCTGCACCAG

GACTGGCTGAATGGCAAGGAGTACAAGTGCAAGGT

CTCCAACAAAGCCCTCCCAGCCCCCATCGAGAAAA

CCATCTCCAAAGCCAAAGGGCAGCCCCGAGAACCA

CAGGTGTACACCCTGCCCCCATCCCGGGATGAGCT

GACCAAGAACCAGGTCAGCCTGACCTGCCTGGTCA

AAGGCTTCTATCCCAGCGACATCGCCGTGGAGTGG

GAGAGCAATGGGCAGCCGGAGAACAACTACAAGAC

CACGCCTCCCGTGCTGGACTCCGACGGCTCCTTCT

TCCTCTACAGCAAGCTCACCGTGGACAAGAGCAGG

TGGCAGCAGGGGAACGTCTTCTCATGCTCCGTGAT

GCATGAGGCTCTGCACAACCACTACACGCAGAAGA

GCCTCTCCCTGTCTCCGGGTTAG.

TABLE A

Insulin-Fc fusion protein sequences and their constituent parts

| Fusion protein SEQ ID NO: | B-chain aa seq | C-peptide aa seq | A-chain aa seq | Linker aa seq | Fc fragment aa seq |
|---|---|---|---|---|---|
| 1 | FVNQHLCGSDLVEALALVCGERGFFYTDPT (SEQ ID NO: 7) | GGGPR (SEQ ID NO: 9) | GIVEQCCHSICSLYQLENYCN (SEQ ID NO: 11) | GGGGAGGG (SEQ ID NO: 13) | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 15) |

TABLE A-continued

Insulin-Fc fusion protein sequences and their constituent parts

| Fusion protein SEQ ID NO: | B-chain aa seq | C-peptide aa seq | A-chain aa seq | Linker aa seq | Fc fragment aa seq |
|---|---|---|---|---|---|
| 3 | FVNQHLCGSHLVEALELVCGERGFHY (SEQ ID NO: 8) | GGGGGGSGGGG (SEQ ID NO: 10) | GIVEQCCTSTCSLDQLENYC (SEQ ID NO: 12) | GGGGGQGGGQGGGQGGGGG (SEQ ID NO: 14) | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 15) |
| 18 | FVNQHLCGSDLVEALALVCGERGFFYTDPT (SEQ ID NO: 7) | GGGPR (SEQ ID NO: 9) | GIVEQCCHSICSLYQLENYCN (SEQ ID NO: 11) | GGGGAGGGGAGGGG SEQ ID NO: 34 | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 15) |
| 20 | FVNQHLCGSDLVEALALVCGERGFFYTDPT (SEQ ID NO: 7) | GGGPR (SEQ ID NO: 9) | GIVEQCCHSICSLYQLENYC (SEQ ID NO: 32) | GGGGAGGGG (SEQ ID NO: 13) | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 15) |
| 22 | FVNQHLCGSDLVEALALVCGERGFFYTDPT (SEQ ID NO: 7) | GGGPR (SEQ ID NO: 9) | GIVEQCCHSICSLYQLENYCN (SEQ ID NO: 11) | GGGG SEQ ID NO: 35 | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 15) |
| 24 | FVNQHLCGSDLVEALALVCGERGFFYTDPT (SEQ ID NO: 7) | GGGPR (SEQ ID NO: 9) | GIVEQCCHSICSLYQLENYCN (SEQ ID NO: 11) | No Linker | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 15) |
| 26 | FVNQHLCGSHLVEALALVCGERGFFYTDPT (SEQ ID NO: 30) | GGGPR (SEQ ID NO: 9) | GIVEQCCHSICSLYQLENYCN (SEQ ID NO: 11) | GGGGAGGGG (SEQ ID NO: 13) | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 15) |
| 28 | FVNQHLCGSHLVEALALVCGERGFFYTPK (SEQ ID NO: 31) | GGGPR (SEQ ID NO: 9) | GIVEQCCTSICSLYQLENYCN SEQ ID NO: 33 | GGGGAGGGG (SEQ ID NO: 13) | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPEN |

TABLE A-continued

Insulin-Fc fusion protein sequences and their constituent parts

| Fusion protein SEQ ID NO: | B-chain aa seq | C-peptide aa seq | A-chain aa seq | Linker aa seq | Fc fragment aa seq |
|---|---|---|---|---|---|
| | | | | | NYKTTPPVLDSDGSFFLYSKLTVDKSRW QQGNVFSCSVMHEALHNHYTQKSLSLSP G (SEQ ID NO: 15) |

The "full aa sequences" of fusion proteins listed in FIG. 2 and FIG. 3 include a leader sequence. In embodiments, a fusion protein described herein does not include a leader sequence at the N-terminus. In embodiments, a fusion protein described herein includes a leader sequence, e.g., at the N-terminus. An exemplary leader sequence includes the amino acid sequence MEWSWVFLFFLSVTTGVHS (SEQ ID NO: 16). In embodiments, a fusion protein described herein is encoded by a nucleic acid molecule comprising a leader sequence, e.g., for expression (e.g., recombinant expression) in cells (e.g., eukaryotic, e.g., mammalian cells). In embodiments, the leader sequence is part of the fusion protein inside a cell and then the leader sequence is cleaved off, e.g., within the cell or in the cell culture, during expression of the fusion protein into the cell culture media via a process (e.g., an enzymatic process).

An exemplary nucleic acid sequence encoding a leader sequence includes the nucleic acid sequence: ATGGAATGGAGCTGGGTCTTTCTCTTCTTCCTGTCAGTAACGACTGGTGTCCACTCC (SEQ ID NO: 17). In embodiments, a fusion protein described herein is encoded by a nucleic acid molecule not comprising a leader sequence.

In some embodiments, the fusion protein is in a preparation. In embodiments, the preparation has a percent dimer, e.g., homodimer, of the fusion protein that is greater than about 50%, e.g., greater than about 55%, about 60%, about 65%, about 70%, about 75%, about 80%, about 85%, about 90%, 95% or about 100%. In embodiments, the percent dimer, e.g., homodimer, of the fusion protein preparation is 91%, 92%, 93%, 94%, 95%, 96%, 97%, 98%, 99% or 100%. In embodiments, the percent homodimer is about 70% or higher (e.g., 80%, 85%, or 88% or more) and can be made 90% or higher (e.g., 95%, 97%, 98%, 99% or nearly 100%) using one or more processing steps (e.g., ion exchange chromatography, gel filtration, hydrophobic interaction chromatography, etc.). In some embodiments, the % dimer, e.g., homodimer, in the preparation is determined by size-exclusion chromatography (see Example 5a and Example 5b) which is an analytical separation method that can discriminate between dimers, e.g., homodimers, and higher-order non-covalent Fc fusion protein aggregates (e.g., multimers). In some embodiments, the % dimer, e.g., homodimer, is determined to be greater than 95%, e.g., as determined by size-exclusion chromatography. In some embodiments, the % dimer, e.g., homodimer, is determined to be greater than 99%, e.g., as determined by size-exclusion chromatography. In some embodiments, insulin-Fc fusion proteins with substantially greater homodimer content than other insulin-Fc fusion proteins demonstrate more bioactivity in a subject (e.g., a human).

Fusion Protein Production

In embodiments, a fusion protein can be expressed by a vector as described in the Examples section.

Expression and Purification

In embodiments, a fusion protein can be expressed recombinantly, e.g., in a eukaryotic cell, e.g., mammalian cell or non-mammalian cell. Exemplary mammalian cells used for expression include HEK cells, e.g., HEK293 cells, or CHO cells. In embodiments, cells are transfected with a nucleic acid molecule, e.g., vector, encoding the fusion protein (e.g., where the entire fusion protein is encoded by a single nucleic acid molecule). In other embodiments, cells are transfected with more than one nucleic acid molecule, where each nucleic acid molecule encodes a different domain of the fusion protein. For example, one nucleic acid molecule can encode the insulin polypeptide, and a different nucleic acid molecule can encode the Fc fragment. Cells can be cultured using standard methods in the art.

In some embodiments, the fusion protein is purified or isolated from the cells (e.g., by lysis of the cells). In other embodiments, the fusion protein is secreted by the cells and, e.g., the fusion protein is purified or isolated from the cell culture media in which the cells were grown. Purification of the fusion protein can include using column chromatography, e.g., affinity chromatography, or using other separation methods that involve size, charge, and/or affinity for certain molecules. In embodiments, purification of the fusion protein involves selecting or enriching for proteins with an Fc fragment, e.g., by using Protein A beads or a Protein A column that cause proteins containing an Fc fragment to become bound with high affinity at neutral solution pH to the Protein A covalently conjugated to the Protein A beads. The bound Fc fusion protein may then be eluted from the Protein A beads by a change in a solution variable (e.g., a decrease in the solution pH). Other separation methods such as ion exchange chromatography and/or gel filtration chromatography can also be employed alternatively or in addition. In embodiments, purification of the fusion protein further comprises filtering or centrifuging the protein preparation. In embodiments, further purification of the fusion protein comprises diafiltration, ultrafiltration, and filtration through porous membranes of various sizes, as well as final formulation with excipients.

The purified fusion protein can be characterized, e.g., for purity, yield, structure, and/or activity, using a variety of methods, e.g., absorbance at 280 nm (e.g., to determine yield), size exclusion or capillary electrophoresis (e.g., to determine the molecular weight, percent aggregation, and/or purity), mass spectrometry (MS) and/or liquid chromatography (LC-MS) (e.g., to determine purity), and/or ELISA (e.g., to determine extent of binding, e.g., affinity, to an anti-insulin antibody). Exemplary methods of characterization are also described in the Examples section.

Functional Features of Fusion Proteins

Described herein are methods for interacting with the human insulin receptor to reduce cancer tumor growth rates in mammals. The methods comprise the administration of a fusion protein (e.g., fusion protein described herein) to a subject. In embodiments, a fusion protein described herein is capable of lowering glucose levels (e.g., blood glucose levels) after administration in a subject. In embodiments, the glucose lowering activity of the fusion protein is higher than that of an insulin reference standard. In some embodiments, the duration of activity of the fusion protein can be measured by a decrease, e.g., a statistically significant decrease, in blood glucose relative to a pre-dose level.

In embodiments, the duration of activity of the fusion protein (e.g., the time during which there is a statistically significant decrease in blood glucose level in a subject relative to a pre-dose level) is longer than about 2 hours. In embodiments, the duration of activity of the fusion protein (e.g. the time during which there is a statistically significant decrease in blood glucose level in a subject relative to a pre-dose level) is longer than about 2 hours, 6 hours, 9 hours, 12 hours, 18 hours, 1 day, 1.5 days, 2 days, 2.2 days, 2.5 days, 3 days, 5 days, 7 days, 8 days, 9 days, 10 days or longer. In embodiments, the duration of activity of the fusion protein (e.g., the time during which there is a statistically significant decrease in blood glucose level in a subject relative to a pre-dose level) is longer than that of an insulin reference standard or control formulation.

Pharmaceutical Compositions and Routes of Administration

Provided herein are pharmaceutical compositions containing a fusion protein described herein that can be used to lower blood glucose in humans. The amount and concentration of the fusion protein in the pharmaceutical compositions, as well as the quantity of the pharmaceutical composition administered to a subject, can be selected based on clinically relevant factors, such as medically relevant characteristics of the subject (e.g. age, weight, gender, other medical conditions, and the like), the solubility of compounds in the pharmaceutical compositions, the potency and activity of the compounds, and the manner of administration of the pharmaceutical compositions. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

Formulations of the present disclosure include those suitable for parenteral administration. The phrases "parenteral administration" and "administered parenterally" as used herein means modes of administration other than enteral and topical administration, usually by intravenous or subcutaneous injection.

Examples of suitable aqueous and non-aqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants, e.g., Tween-like surfactants. In some embodiments, the pharmaceutical composition (e.g., as described herein) comprises a Tween-like surfactant, e.g., Tween-20 or Tween-80. In some embodiments, the pharmaceutical composition (e.g., as described herein) comprises a Tween-like surfactant, e.g., Tween-80, at a concentration between about 0.001% and about 2%, or between about 0.005% and about 0.1%, or between about 0.01% and about 0.5%.

In some embodiments, the fusion protein is administered as a bolus, infusion, or an intravenous push. In some embodiments, the fusion protein is administered through syringe injection, pump, pen, needle, or indwelling catheter. Methods of introduction may also be provided by rechargeable or biodegradable devices. Various slow-release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Dosages

Actual dosage levels of the fusion protein can be varied so as to obtain an amount of the active ingredient that is effective to achieve the desired therapeutic response for a particular mammal. The selected dosage level will depend upon a variety of factors including the activity of the particular fusion protein employed, or the ester, salt or amide thereof, the route of administration, the time of administration, the rate of excretion of the particular compound being employed, the duration of the treatment, other drugs, compounds and/or materials used in combination with the particular fusion protein employed, the age, sex, weight, condition, general health and prior medical history of the human being treated, and like factors well known in the medical arts.

In general, a suitable dose of a fusion protein will be that amount of the fusion protein that is the lowest dose effective to produce a therapeutic effect. Such an effective dose will generally depend upon the factors described above. Generally, intravenous, and subcutaneous doses of the fusion protein for a mammal will range from about 150 to about 1500 micrograms per kilogram of body weight per day.

The present disclosure contemplates formulation of the fusion protein in any of the aforementioned pharmaceutical compositions and preparations. Furthermore, the present disclosure contemplates administration via any of the foregoing routes of administration. One of skill in the art can select the appropriate formulation and route of administration based on the condition being treated and the overall health, age, and size of the patient being treated.

EXAMPLES

The present technology is further illustrated by the following Examples, which should not be construed as limiting in any way.

Example 1a: Synthesis and Methods of Making an Insulin-Fc Fusion Protein in HEK Cells Insulin-Fc fusion proteins were synthesized as follows. A gene sequence of interest was constructed using proprietary software (LakePharma, Belmont, Calif.) and was cloned into a high expression mammalian vector. HEK293 cells were seeded in a shake flask 24 hours before transfection and were grown using serum-free chemically defined media. A DNA expression construct that encodes the insulin-Fc fusion protein of interest was transiently transfected into a 2 L suspension of HEK293 cells using the Syd Labs (Natick, Mass.) standard operating procedure for transient transfection. After 20 hours, cells were counted to determine the viability and viable cell count, and titer was measured by ForteBio® Octet® (Pall ForteBio LLC, Fremont, Calif.). Additional readings were taken throughout the transient transfection production run. The culture was harvested on or after day 5.

Example 1b: Synthesis and Methods of Making an Insulin-Fc Fusion Protein in CHO Cells A CHO cell line was originally derived from CHO-K1 (LakePharma, Belmont, Calif.), and the endogenous glutamine synthetase (GS) genes were knocked out by recombinant technology using methods known in the art. Stable expression DNA vectors were designed and optimized for CHO expression and GS selection and incorporated into a high expression mammalian vector (LakePharma, Belmont, Calif.). The sequence of each completed construct was confirmed prior to initiating scale up experiments. The suspension-adapted CHO cells were cultured in a humidified 5% $CO_2$ incubator at 37° C. in a chemically defined media (CD OptiCHO; Invitrogen, Carlsbad, Calif.). No serum or other animal-derived products were used in culturing the CHO cells.

Approximately 80 million suspension-adapted CHO cells, growing in CD OptiCHO media during the exponential growth phase, were transfected by electroporation using MaxCyte® STX® system (MaxCyte, Inc., Gaithersburg, Md.) with 80 μg DNA to a create a stable CHO cell line for each insulin-Fc fusion protein (DNA construct contains the full-length sequence of the insulin-Fc fusion protein). After twenty-four hours, the transfected cells were counted and placed under selection for stable integration of the insulin-Fc fusion genes. The transfected cells were seeded into CD OptiCHO selection media containing between 0-100 μM methionine sulfoximine (MSX) at a cell density of 0.5×10⁶ cells/mL in a shaker flask and were incubated at 37° C. with 5% $CO_2$. During a selection process, the cells were spun down and resuspended in fresh selection media every 2-3 days until the CHO stable pool recovered its growth rate and viability. The cell culture was monitored for growth and titer.

The cells were grown to 2.5×10⁶ cells per mL. At the time of harvest for cell banking, the viability was above 95%. The cells were then centrifuged, and the cell pellet was resuspended in the CD OptiCHO media with 7.5% dimethyl sulfoxide (DMSO) to a cell count of 15×10⁶ cells per mL per vial. Vials were cryopreserved for storage in liquid nitrogen.

A small-scale-up production was performed using the CHO cells as follows. The cells were scaled up for production in CD OptiCHO growth medium containing 100 μM MSX at 37° C. and fed every 2-4 days as needed, with CD OptiCHO growth medium supplemented with glucose and additional amino acids as necessary for approximately 14-21 days. The conditioned media supernatant harvested from the stable pool production run was clarified by centrifuge spinning. The protein was run over a Protein A (Mab Select, GE Healthcare, Little Chalfont, United Kingdom) column pre-equilibrated with binding buffer. Washing buffer was then passed through the column until the OD280 value (Nano-Drop, Thermo Scientific) was measured to be at or near background levels. The insulin-Fc fusion protein was eluted using a low pH buffer, elution fractions were collected, and the OD280 value of each fraction was recorded. Fractions containing the target insulin-Fc fusion protein were pooled and optionally further filtered using a 0.2 μM membrane filter.

The cell line was optionally further subcloned to monoclonality and optionally further selected for high titer insulin-Fc-fusion protein-expressing clones using the method of limiting dilution, a method known to those skilled in the art. After obtaining a high titer, monoclonal insulin-Fc fusion protein-expressing cell line, production of the insulin-Fc fusion protein was accomplished as described above in growth medium without MSX, or optionally in growth medium containing MSX, to obtain a cell culture supernatant containing the recombinant, CHO-made, insulin-Fc fusion protein. The MSX concentration was optionally increased over time to exert additional selectivity for clones capable of yielding higher product titers.

Example 1c: Synthesis and Methods of Making an Insulin-Fc Fusion Protein in CHO Cells A CHO cell line is originally derived from CHO-K1 (LakePharma, Belmont, Calif.), and the endogenous glutamine synthetase (GS) genes are knocked out by recombinant technology using methods known in the art. Stable expression DNA vectors are designed and optimized for CHO expression and GS selection and incorporated into a high expression mammalian vector (LakePharma, Belmont, Calif.). The sequence of each completed construct is confirmed prior to initiating scale up experiments. The suspension-adapted CHO cells are cultured in a humidified 5% $CO_2$ incubator at 37° C. in a chemically defined media (CD OptiCHO; Invitrogen, Carlsbad, Calif.). No serum or other animal-derived products are used in culturing the CHO cells.

Approximately 80 million suspension-adapted CHO cells, growing in CD OptiCHO media during the exponential growth phase, are transfected by electroporation using MaxCyte® STX® system (MaxCyte, Inc., Gaithersburg, Md.) with 80 μg DNA to a create a stable CHO cell line for each insulin-Fc fusion protein (DNA construct contains the full-length sequence of the insulin-Fc fusion protein). After twenty-four hours, the transfected cells are counted and placed under selection for stable integration of the insulin-Fc fusion genes. The transfected cells are seeded into CD OptiCHO selection media containing between 0-100 μM methionine sulfoximine (MSX) at a cell density of 0.5×10⁶ cells/mL in a shaker flask and are incubated at 37° C. with 5% $CO_2$. During a selection process, the cells are spun down and resuspended in fresh selection media every 2-3 days until the CHO stable pool recovered its growth rate and viability. The cell culture is monitored for growth and titer.

The cells are grown to 2.5×10⁶ cells per mL. At the time of harvest for cell banking, the viability is to remain above 95%. The cells are then centrifuged, and the cell pellet resuspended in the CD OptiCHO media with 7.5% dimethyl sulfoxide (DMSO) to a cell count of 15×10⁶ cells per mL per vial. Vials are cryopreserved for storage in liquid nitrogen.

A small-scale-up production is performed using the CHO cells as follows. The cells are scaled up for production in CD OptiCHO growth medium containing 100 μM MSX at 37° C. and fed every 2-4 days as needed, with CD OptiCHO growth medium supplemented with glucose and additional amino acids as necessary for approximately 14-21 days. The conditioned media supernatant harvested from the stable pool production run is clarified by centrifuge spinning. The protein is run over a Protein A (MabSelect, GE Healthcare, Little Chalfont, United Kingdom) column pre-equilibrated with binding buffer. Washing buffer is then passed through the column until the OD280 value (NanoDrop, Thermo Scientific) is measured to be at or near background levels. The insulin-Fc fusion protein is eluted using a low pH buffer, elution fractions are collected, and the OD280 value of each fraction is recorded. Fractions containing the target insulin-Fc fusion protein are pooled and optionally further filtered using a 0.2 µM membrane filter.

The cell line is optionally further subcloned to monoclonality and optionally further selected for high titer insulin-Fc-fusion protein-expressing clones using the method of limiting dilution, a method known to those skilled in the art. After obtaining a high titer, monoclonal insulin-Fc fusion protein-expressing cell line, production of the insulin-Fc fusion protein is accomplished as described above in growth medium without MSX, or optionally in growth medium containing MSX, to obtain a cell culture supernatant containing the recombinant, CHO-made, insulin-Fc fusion protein. The MSX concentration is optionally increased over time to exert additional selectivity for clones capable of yielding higher product titers.

Example 2: Purification of an Insulin-Fc Fusion Protein

Purification of an insulin-Fc fusion protein was performed as follows. Conditioned media supernatants containing the secreted Fc fusion protein were harvested from the transiently transfected HEK, stably transfected HEK, or stably transfected CHO production runs and were clarified by centrifugation. The supernatant containing the desired insulin-Fc fusion protein was run over a Protein A column, washed with various wash buffers including 0.15-0.50M sodium chloride, and then eluted using a low pH solution. Afterwards, the eluted desired protein fractions were pooled, and buffer exchanged into 200 mM HEPES, 100 mM NaCl, 50 mM NaOAc, pH 7.0 buffer. A final filtration step was performed using a 0.2 µm membrane filter. The final protein concentration was calculated from the solution optical density at 280 nm. Further optional purification by ion-exchange chromatography (e.g., using an anion exchange bead resin or a cation exchange bead resin), gel filtration chromatography, or other methods was performed as necessary. In some embodiments, the insulin-Fc fusion was buffer exchanged via Zeba gel filtration columns (Thermo) into 50 mM sodium phosphate, pH 7.0 buffer and purified via Q-HP (Cytiva) ion exchange columns operating in flow through mode to remove molecular aggregates, host cell protein, and host cell DNA. After the Q-HP step, buffer exchange was performed as needed via Zeba gel filtration columns (Thermo) into PBS buffer (25 mM sodium phosphate, 150 mM sodium chloride, pH 7.4).

As shown in Table 1, an exemplary insulin-Fc fusion protein of the present technology (SEQ ID NO: 1) synthesized in HEK293 cells exhibited an adequate titer. It has been determined that insulin-Fc fusion proteins of structures and compositions similar to the insulin-Fc fusion proteins of the current disclosure exhibiting protein-A purified titers in excess of 50 mg/L for transiently transfected HEK293 cells demonstrate higher, commercially viable CHO cell titers when the compounds are expressed using stably transfected CHO cells.

TABLE 1

Titer (mg/L) for Insulin-Fc Fusion Proteins Manufactured in HEK293 Cells

| Sequence | Titer (mg/L) |
| --- | --- |
| SEQ ID NO: 18 | 105 |
| SEQ ID NO: 20 | 108 |
| SEQ ID NO: 22 | 93 |
| SEQ ID NO: 1 | 80 |
| SEQ ID NO: 24 | 85 |
| SEQ ID NO: 26 | 41 |
| SEQ ID NO: 28 | 27 |
| SEQ ID NO: 3 | 196 |

Subsequent work performed in stably transfected CHO-K1 GSN cells (LakePharma, Belmont, Calif.) demonstrated stable pool titers of 384 mg/mL for SEQ ID NO: 1, and stable clone titers of 750 mg/mL for SEQ ID NO: 1.

It is expected that the insulin-Fc fusion proteins of SEQ ID NO: 3, SEQ ID NO: 18, SEQ ID NO: 20, SEQ ID NO: 22, SEQ ID NO: 24, SEQ ID NO: 26 and SEQ ID NO: 28, when stably transfected in CHO-K1 GSN cells (LakePharma, Belmont, Calif.) will demonstrate stable pool titers of greater than 200 mg/mL and stable clone titers of greater than 500 mg/mL.

Example 3: Structure Confirmation by Non-Reducing and Reducing CE-SDS

Capillary electrophoresis sodium dodecyl sulfate (CE-SDS) analysis was performed in a LabChip® GXII (Perkin Elmer, Waltham, Mass.) on a solution of a purified insulin-Fc fusion protein dissolved in 200 mM HEPES, 100 mM NaCl, 50 mM NaOAc, pH 7.0 buffer, and the electropherogram was plotted. Under non-reducing conditions, the sample was run against known molecular weight (MW) protein standards, and the eluting peak represented the 'apparent' MW of the insulin-Fc fusion protein homodimer.

Under reducing conditions (e.g., using beta-mercaptoethanol to break disulfide bonds of the fusion protein), the apparent MW of the resulting insulin-Fc fusion protein monomer is compared against half the molecular weight of the insulin-Fc fusion protein homodimer as a way of determining that the structural purity of the insulin-Fc fusion protein is likely to be correct.

The non-reducing and reducing main peaks found via CE-SDS analysis for insulin-Fc fusion proteins synthesized in HEK293 cells are shown in Table 2, and 2× the apparent MW of the resulting insulin-Fc fusion protein monomer was compared to the molecular weight of the insulin-Fc fusion protein homodimer. The results in Table 2 illustrate that the structural purities of the insulin-Fc fusion proteins are likely to be correct.

TABLE 2

CE-SDS Non-Reducing and Reducing Main Peak for insulin-Fc fusion proteins synthesized in HEK293 cells

| Sequence | Non-reducing (kDa) Peak | Reducing (kDa) Peak | $\frac{MW_{homdimer}}{2 \times MW_{monomer}}$ |
| --- | --- | --- | --- |
| SEQ ID NO: 18 | 89.3 | 43.0 | 2.08 |
| SEQ ID NO: 20 | 88.0 | 42.1 | 2.09 |
| SEQ ID NO: 22 | 91.5 | 42.8 | 2.14 |
| SEQ ID NO: 1 | 85.3 | 44.1 | 1.93 |
| SEQ ID NO: 24 | 90.9 | 42.5 | 2.14 |
| SEQ ID NO: 26 | 87.9 | 46.5 | 1.89 |

TABLE 2-continued

CE-SDS Non-Reducing and Reducing Main Peak for insulin-Fc fusion proteins synthesized in HEK293 cells

| Sequence | Non-reducing (kDa) Peak | Reducing (kDa) Peak | $\frac{MW_{homdimer}}{2 \times MW_{monomer}}$ |
|---|---|---|---|
| SEQ ID NO: 28 | 88.6 | 46.6 | 1.90 |
| SEQ ID NO: 3 | 77.7 | 36.9 | 2.11 |

Example 4: Sequence Identification by LC-MS with Glycan Removal

To obtain an accurate estimate of the insulin-Fc mass via mass spectroscopy (MS), the sample is first treated to remove naturally occurring glycan that might interfere with the MS analysis. 100 µL of a 2.5 mg/mL insulin-Fc fusion protein dissolved in 200 mM HEPES, 100 mM NaCl, 50 mM NaOAc, pH 7.0 buffer solution is first buffer exchanged into 0.1 M Tris, pH 8.0 buffer containing 5 mM EDTA using a Zeba desalting column (ThermoFisher Scientific, Waltham, Mass.). 1.67 µL of PNGase F enzyme (Prozyme N-glycanase) is added to this solution in order to remove N-linked glycan present in the fusion protein, and the mixture is incubated at 37° C. overnight in an incubator. The sample is then analyzed via LC-MS (Novatia, Newtown, Pa.) resulting in a molecular mass of the molecule which corresponded to the desired homodimer without the glycan. This mass is then further corrected since the enzymatic process used to cleave glycan from asparagine also deaminates the asparagine side chain to form an aspartic acid, and in doing so the enzymatically treated homodimer gains 2 Da overall, corresponding to a mass of 1 Da for each chain present in the homodimer. Therefore, the actual molecular mass is the measured mass minus 2 Da to correct for the enzymatic modification of the insulin-Fc fusion protein structure in the analytical sample. The LC-MS expected molecular mass data, expected corrected mass data, and theoretical molecular masses (obtained via Expasy MW/pI tool) for exemplary insulin-Fc fusion proteins are shown in Table 3.

TABLE 3

Expected Molecular Mass by MS Compared to Theoretical

| | After PNGase treatment | | |
|---|---|---|---|
| Sequence | Measured Molecular Mass (Da) | Measured Mass, Corrected for N to D transformation (subtract 2 Da) | Desired Homodimer Molecular Mass (theoretical, from aa sequence, Da) |
| SEQ ID NO: 18 | 65005.3 ± 5 | 65003.3 ± 5 | 65003.3 |
| SEQ ID NO: 20 | 64178.5 ± 5 | 64176.5 ± 5 | 64176.5 |
| SEQ ID NO: 22 | 63808.2 ± 5 | 63806.2 ± 5 | 63806.2 |
| SEQ ID NO: 1 | 64406.7 ± 5 | 64404.7 ± 5 | 64404.7 |
| SEQ ID NO: 24 | 63351.7 ± 5 | 63349.7 ± 5 | 63349.7 |
| SEQ ID NO: 26 | 64450.8 ± 5 | 64448.8 ± 5 | 64448.8 |
| SEQ ID NO: 28 | 64202.7 ± 5 | 64200.7 ± 5 | 64200.7 |
| SEQ ID NO: 3 | 65219.0 ± 5 | 65217.0 ± 5 | 65217.0 |

Example 5a: % Homodimer by Size-Exclusion Chromatography

Size-exclusion chromatography (SEC-HPLC) of insulin-Fc fusion proteins was carried out using a Waters 2795HT HPLC (Waters Corporation, Milford, Mass.) connected to a 2998 Photodiode array at a wavelength of 280 nm. 100 µL or less of a sample containing an insulin-Fc fusion protein of interest was injected into a MAbPac SEC-1, 5 µm, 4×300 mm column (ThermoFisher Scientific, Waltham, Mass.) operating at a flow rate of 0.2 mL/min and with a mobile phase comprising 50 mM sodium phosphate, 300 mM NaCl, and 0.05% w/v sodium azide, pH 6.2. The MAbPac SEC-1 column operates on the principle of molecular size separation. Therefore, larger soluble insulin-Fc aggregates (e.g., multimers of insulin-Fc fusion protein homodimers) eluted at earlier retention times, and the non-aggregated homodimers eluted at later retention times. In separating the mixture of homodimers from aggregated multimeric homodimers via analytical SEC-HPLC, the purity of the insulin-Fc fusion protein solution in terms of the percentage of non-aggregated homodimer was ascertained. Table 4 shows the homodimer percentage of insulin-Fc fusion proteins manufactured in HEK293 cells.

TABLE 4

SE-HPLC determined percentage of compound in homodimer form

| Sequence | % Homodimer after Protein A step of Example 2 | % Homodimer after Protein A step and Additional Q-HP ion exchange column step via the process of Example 2 |
|---|---|---|
| SEQ ID NO: 1 | 87.0 | >98 |
| SEQ ID NO: 3 | 97.6 | N/A |

Example 5b: % Homodimer by Size-Exclusion Chromatography

Size-exclusion chromatography (SEC-HPLC) of insulin-Fc fusion proteins is carried out using a Waters 2795HT HPLC (Waters Corporation, Milford, Mass.) connected to a 2998 Photodiode array at a wavelength of 280 nm. 100 µL or less of a sample containing an insulin-Fc fusion protein of interest is injected into a MAbPac SEC-1, 5 µm, 4×300 mm column (ThermoFisher Scientific, Waltham, Mass.) operating at a flow rate of 0.2 mL/min and with a mobile phase comprising 50 mM sodium phosphate, 300 mM NaCl, and 0.05% w/v sodium azide, pH 6.2. The MAbPac SEC-1 column operates on the principle of molecular size separation. Therefore, larger soluble insulin-Fc aggregates (e.g., multimers of insulin-Fc fusion protein homodimers) elute at earlier retention times, and the non-aggregated homodimers elute at later retention times. In separating the mixture of homodimers from aggregated multimeric homodimers via analytical SEC-HPLC, the purity of the insulin-Fc fusion protein solution in terms of the percentage of non-aggregated homodimer is ascertained.

It is expected that the insulin-Fc fusion proteins of SEQ ID NO: 18, SEQ ID NO: 20, SEQ ID NO: 22, SEQ ID NO: 24, SEQ ID NO: 26, and SEQ ID NO: 28 will exhibit a homodimer percentage after Protein A step of Example 2 in excess of 80%.

It is expected that the insulin-Fc fusion proteins of SEQ ID NO: 3, SEQ ID NO: 18, SEQ ID NO: 20, SEQ ID NO: 22, SEQ ID NO: 24, SEQ ID NO: 26, and SEQ ID NO: 28 will exhibit a homodimer percentage after Protein A step and addition Q-HP ion exchange column step via the process of Example 2 in excess of 90%.

Example 6: In Vitro IM-9 Insulin Receptor (IR) Binding of Insulin-Fc Fusion Proteins at 4° C.

Human IM-9 cells (ATTC #CCL-159) that express human insulin receptor were cultured and maintained in complete RPMI 10% FBS medium at 70-80% confluency. Cultures of IM-9 cells were centrifuged at 250×g (~1000 rpm) for 10 min to pellet the cells. Cells were washed once with HBSS or PBS buffer, resuspended in cold FACS medium (HBSS/2 mM EDTA/0.1% Na-azide+2% horse serum) to a concentration of 1×107 cells/mL and kept on ice (4° C.) for 20-30 min in FACS buffer. Insulin-Fc proteins, insulins, or insulin analogs (e.g., test compounds) were diluted in FACS buffer in 1:4 serial dilutions as 2× concentrations (800 nM, 400 nM, 100 nM, 25 nM, 6.25 nM, 1.57 nM, 0.39 nM) in 1.2 mL tubes (approx. 60 μL volume of each dilution), and the solutions were kept on ice to reach 4° C. tubes until ready for pipetting.

Biotinylated-RHI was diluted in FACS staining medium as a 20× concentration at 10 μg/mL (final 0.5 μg/mL). 50 μL of each serially diluted test compound and 5 μL of 20× Biotin-RHI were added into each well of a V bottom microtiter plate, mixed, and placed on ice. 45 μL of IM-9 cell suspension was then added to each well by multichannel pipette, mixed again gently and incubated on ice for 30 min to allow competitive binding on the insulin receptor (IR) on IM-9 cells. Cells were then washed twice with 250 μL of ice-cold FACS wash buffer (HBSS/2 mM EDTA/0.1% Na-azide+0.5% horse serum) by centrifuging the V-bottom plate at 3000 rpm for 3 min and aspirating the supernatant. Cells were then resuspended in 504, of FACS medium containing 1:200 diluted Streptavidin-PE(Life Technologies) for 20 min on ice. Cells were then washed once with 250 μL of ice-cold FACS buffer and finally fixed with 4% paraformaldehyde for 10 min.

Cells were then transferred to FACS tubes and analyzed on a Guava 8-HT flow cytometer (Millipore). Biotinylated-RHI binding to insulin receptor was quantitated by the median fluorescence intensity (MFI) of the cells on the FACS FL-2 channel and was measured for each concentration of the test compound. Control wells were labeled only with biotinylated-RHI and were used to calculate the % inhibition resulting from each test compound concentration. The percent (%) inhibition by test compounds of biotinylated-RHI binding on IM-9 cells was plotted against log concentrations of each test compound and IC50 values were calculated using GraphPad Prism (GraphPad Software, La Jolla, Calif.) for each test compound. Lower IC50 values of test compounds were reflective of stronger binding to insulin receptors. A control compound, such as unlabeled recombinant human insulin (RHI) was also used as an internal standard to generate an RHI IC50 against which a given compound IC50 could be ratioed (IC50(compound)/IC50 (RHI)). Lower IC50 ratios have more similar binding to RHI (stronger binding to insulin receptor), while higher IC50 ratios have weaker binding to the insulin receptor relative to RHI. Inhibition of biotin labelled-insulin binding to IM-9 insulin receptor (IC50; nM) of the test compound and inhibition of biotin labelled-insulin binding to IM-9 insulin receptor (IC50; nM) of RHI were measured, and the IC50 ratio of the test compound to RHI was determined for the insulin-Fc fusion proteins of SEQ ID NO: 1, SEQ ID NO: 3, SEQ ID NO: 18, SEQ ID NO: 20, SEQ ID NO: 22, SEQ ID NO: 24, SEQ ID NO: 26, and SEQ ID NO: 28) are shown in Table 5. An RHI control was run in each batch of experiments and the IC50 for each insulin-Fc fusion protein is reported and ratioed to the RHI control run within that particular experiment batch.

TABLE 5

Inhibition of biotin labelled-insulin binding to IM-9 Insulin Receptor and associated compound sequence properties.

| SEQ ID NO: | Compound IC$_{50}$ (nM) | RHI IC$_{50}$ (nM) | IC$_{50}$ Ratio (Compound/ RHI) | AA at position 10 of insulin polypeptide B chain | AA at position 8 of insulin polypeptide A chain | Linker AA Sequence |
|---|---|---|---|---|---|---|
| Experiment Batch #1 | | | | | | |
| SEQ ID NO: 1 | 26 | 5 | 5 | D | H | GGGGAG GGG (SEQ ID NO: 13) |
| SEQ ID NO: 3 | 708 | 5 | 142 | H | T | GGGGGQG GGGQGGG GQGGGGG (SEQ ID NO: 14) |
| Experiment Batch #2 | | | | | | |
| SEQ ID NO: 1 | 55 | 15 | 4 | D | H | GGGGAG GGG (SEQ ID NO: 13) |
| Experiment Batch #3 | | | | | | |
| SEQ ID NO: 18 | 31 | 14 | 2 | D | H | GGGGAGG GGAGGGG (SEQ ID NO: 34) |
| SEQ ID NO: 20 | 35 | 14 | 3 | D | H | GGGGAG GGG (SEQ ID NO: 13) |
| SEQ ID NO: 22 | 45 | 14 | 3 | D | H | GGGG (SEQ ID NO: 35) |
| SEQ ID NO: 24 | 110 | 14 | 8 | D | H | <none> |
| SEQ ID NO: 26 | 805 | 14 | 60 | H | H | GGGGA GGGG (SEQ ID NO: 13) |
| SEQ ID NO: 28 | 1497 | 14 | 111 | H | T | GGGGAG GGG (SEQ ID NO: 13) |

Example 7a: IR Downregulation in HCT-116 Cells

HCT-116 cells were treated in vitro with either RHI, SEQ ID NO: 1 or SEQ ID NO: 3 at multiple concentrations (0.05-500 nM). Levels of tumor IR, phospho-IR+phospho-IGF1R (e.g., "phospho IR/IGF1R"), phospho-Akt (S473), pan Akt, and Beta (β) Actin expression were measured by Western blot. Tumors were lysed in RIPA buffer, electrophoresed on SDS-PAGE gels, transferred to PVDF membranes using a dry blotting system, and probed with the aforementioned proteins using antibodies from Cell Signaling at 1:1000 along with appropriate secondary antibodies known to those skilled in the art. Blots were imaged (cDigit blot scanner, Licor) and assessed using Image Studio software (Licor).

FIG. 5 provides Western blots that showed that after 72 hours of treatment, RHI caused observable downregulation of total IR in HCT-116 cells compared to SEQ ID NO: 3 at the higher concentrations tested. Unexpectedly, SEQ ID NO: 1 caused substantial total IR downregulation in HCT-116 cells compared to SEQ ID NO: 3 at all concentrations tested. This is highlighted as 501 in FIG. 5. Treatments with SEQ ID NO: 1 caused downregulation of total IR even at very low concentrations while treatments with SEQ ID NO: 3 caused very little total IR downregulation even at high concentrations, which may be taken to mean that in a therapeutic setting in a patient, a patient's freely circulating endogenous insulin would be able to freely bind IR to activate the Phospho IR and Akt pathways, allowing tumor proliferation and growth, which would be undesirable. Furthermore, SEQ ID NO: 1 induced lower levels of Akt phosphorylation than RHI at every concentration tested. This is an important finding, as blocking Akt signaling through the use of current cancer therapies has been correlated with slower tumor growth, as Akt signaling is involved in cell proliferation and growth.

The Western blots in FIG. 5 additionally show that SEQ ID NO: 1 demonstrated measurable Phospho IR/IGF1R despite downregulating the IR. This is highlighted as 502 in FIG. 5. This illustrates that treatment with the insulin-Fc fusion protein of SEQ ID NO: 1 unexpectedly caused substantial total IR downregulation while at the same time activating the signal pathway to the insulin receptor (IR), enabling uptake of insulin, and lowering the risk of hyperglycemia that has been associated with IR downregulation in other therapeutic approaches (e.g., without limitation, anti-IR antibodies), or preventing hyperglycemia altogether.

Example 7b: IR Downregulation in HCT-116 Cells

HCT-116 cells are treated in vitro with either RHI, SEQ ID NO: 18, SEQ ID NO: 20, SEQ ID NO: 22, SEQ ID NO: 24, SEQ ID NO: 26 or SEQ ID NO: 28 at multiple concentrations (0.05-500 nM). Levels of tumor IR, phospho-IR, phospho-IGF1R, phospho-Akt (S473), pan Akt, and Beta (β) Actin expression are measured by Western blot. Tumors are lysed in RIPA buffer, electrophoresed on SDS-PAGE gels, transferred to PVDF membranes using a dry blotting system, and probed for the aforementioned proteins using antibodies from Cell Signaling at 1:1000 along with appropriate secondary antibodies known to those skilled in the art. Blots are imaged (cDigit blot scanner, Licor) and assessed using Image Studio software (Licor).

It is expected that Western blots created after 72 hours of treatment will demonstrate that SEQ ID NO: 18, SEQ ID NO: 20, SEQ ID NO: 22 and SEQ ID NO: 24 cause substantial total IR downregulation in HCT-116 cells compared to SEQ ID NO: 26 and SEQ ID NO: 28 at all concentrations tested, consistent with SEQ ID NO: 18, SEQ ID NO: 20, SEQ ID NO: 22 and SEQ ID NO: 24 comprising the B10D mutation on the B-chain of the insulin polypeptide and comprising the A8H mutation on the A-chain of the insulin polypeptide. Treatments with SEQ ID NO: 18, SEQ ID NO: 20, SEQ ID NO: 22 and SEQ ID NO: 24 is expected to cause downregulation of total IR even at very low concentrations while treatments with SEQ ID NO: 26 and SEQ ID NO: 28 are expected to cause very little total IR downregulation even at high concentrations. Furthermore, SEQ ID NO: 1 induced lower levels of Akt phosphorylation than RHI at every concentration tested.

It is further expected that Western blots created after 72 hours of treatment will show that SEQ ID NO: 18, SEQ ID NO: 20, SEQ ID NO: 22 and SEQ ID NO: 24 demonstrate substantial total IR downregulation while at the same time activating the signal pathway to the insulin receptor (IR), as measured by Phospho IR/IGF1R, indicating that these sequences are able to directly lower the risk of hyperglycemia that has been observed for other IR downregulation therapy approaches (e.g. without limitation anti-IR antibodies), or prevent the risk of hyperglycemia altogether. In contrast, SEQ ID NO: 26 and SEQ ID NO: 28 are not expected to demonstrate measurable downregulation of the insulin receptor, and in a therapeutic setting would be predicted to allow a patient's own endogenous insulin to bind abundant insulin receptor (IR) resulting in tumor proliferation and growth, which would be undesirable.

Example 8a: In Vivo Pharmacodynamics (PD) after Single Administration of Fusion Protein in Mice A bioactive fusion protein construct of SEQ ID NO: 1 was synthesized according to Example 1a or Example 1b or Example 1c and assessed for its effects on fasting blood glucose levels as follows. Naïve, non-fasted nude mice were used. On Day 0, the mice received a single injection of a pharmaceutical composition containing a fusion protein homodimer of SEQ ID NO: 1 in a solution of 50 mM sodium hydrogen phosphate, 150 mM sodium chloride, and 0.02% v/v Tween-80 at pH 7.5, at a dose of 6 nmol/kg (equivalent to 0.39 mg Fc fusion protein/kg or 1.9 U/kg insulin equivalent on molar basis). Blood was collected immediately prior to injection and at 15, 30, 45, 60, 120, 240, 360, and 480 minutes and at 1, 2, 3, 4, 5, 6, 7, and 8 days post injection. On Day 0, blood was collected from a suitable vein immediately prior to injection as well as for the rest of the post-treatment timepoints.

For each time point, a minimum of 0.1 mL of whole blood was collected. A glucose level reading was immediately determined using a glucose meter (ACCU-CHEK® Aviva Plus), which requires approximately one drop of blood. Average % fasting blood glucose levels (% FBGL) from Day 0 to Day 8 were plotted in FIG. 6, which allows the bioactivity of a fusion protein to be determined. FIG. 6 demonstrates that the fusion protein of SEQ ID NO: 1 can lower blood glucose for a significant period of time on a single dose.

Example 8b: In Vivo Pharmacodynamics (PD) after Single Administration of Fusion Protein in Mice Insulin-Fc fusion protein constructs of SEQ ID NO: 18, SEQ ID NO: 20, SEQ ID NO: 22 and SEQ ID NO: 24 were synthesized according to Example 1a or Example 1b or Example 1c and assessed for their effects on fasting blood glucose levels as follows. Naïve, non-fasted nude mice are used. On Day 0, the mice receive a single injection of a pharmaceutical composition containing a fusion protein homodimer of SEQ ID NO: 1 in a solution of 50 mM sodium hydrogen phosphate, 150 mM sodium chloride, and 0.02% v/v Tween-80 at pH 7.5, at a dose of 6 nmol/kg (equivalent to 0.39 mg Fc fusion protein/kg or 1.9 U/kg insulin equivalent on molar basis). Blood is collected immediately prior to injection and at 15, 30, 45, 60, 120, 240, 360, and 480 minutes and at 1, 2, 3, 4, 5, 6, 7, and 8 days post injection.

On Day 0, blood is collected from a suitable vein immediately prior to injection as well as for the rest of the post-treatment timepoints.

For each time point, a minimum of 0.1 mL of whole blood is collected. A glucose level reading is immediately determined using a glucose meter (ACCU-CHEK® Aviva Plus), which requires approximately one drop of blood. Average % fasting blood glucose levels (% FBGL) from Day 0 to Day 8 are plotted, which allows the bioactivity of a fusion protein to be determined. It is expected that the fusion proteins of SEQ ID NO: 18, SEQ ID NO: 20, SEQ ID NO: 22 and SEQ ID NO: 24 will lower blood glucose for a significant period of time on a single dose.

Example 9a: Tumor Volume in HCT-116 Xenograft Models in Nude Mice

HCT-116 cells were cultured under aseptic conditions at 37° C. with 5% CO2 in logarithmic growth phase. On the day of the inoculations, the cells were harvested, washed in PBS, and resuspended at the appropriate concentration in a serum-free medium:matrigel (1:1 vol:vol) mixture. Inoculations were carried out in conscious naïve, nude mice (n=60 females) while being manually restrained. Mice were injected subcutaneously (SC) on their dorsal right flank with 2×106 cells using a 28 G needle in 200 μL volume. The injection areas were monitored until the tumors were visible/palpable. Once palpable, calipers were used for tumor measurements twice a week. The greatest longitudinal diameter (length) and the greatest transverse diameter (width) was used to determine tumor volume according to the equation:

$$\text{Tumor volume} = \frac{(\text{length} \times \text{width}^2)}{2}.$$

Once the tumors reached a volume between 100 and 300 mm$^3$, mice bearing HCT-116 tumors were randomized into four groups according to Table 6.

TABLE 6

Test groups for HCT-116 bearing nude mice

|  | Fasted 8-10 hours per day | Unfasted |
|---|---|---|
| Vehicle | fasted controls | unfasted controls |
| Insulin-Fc fusion protein | fasted treated | unfasted treated |

Figure 7:
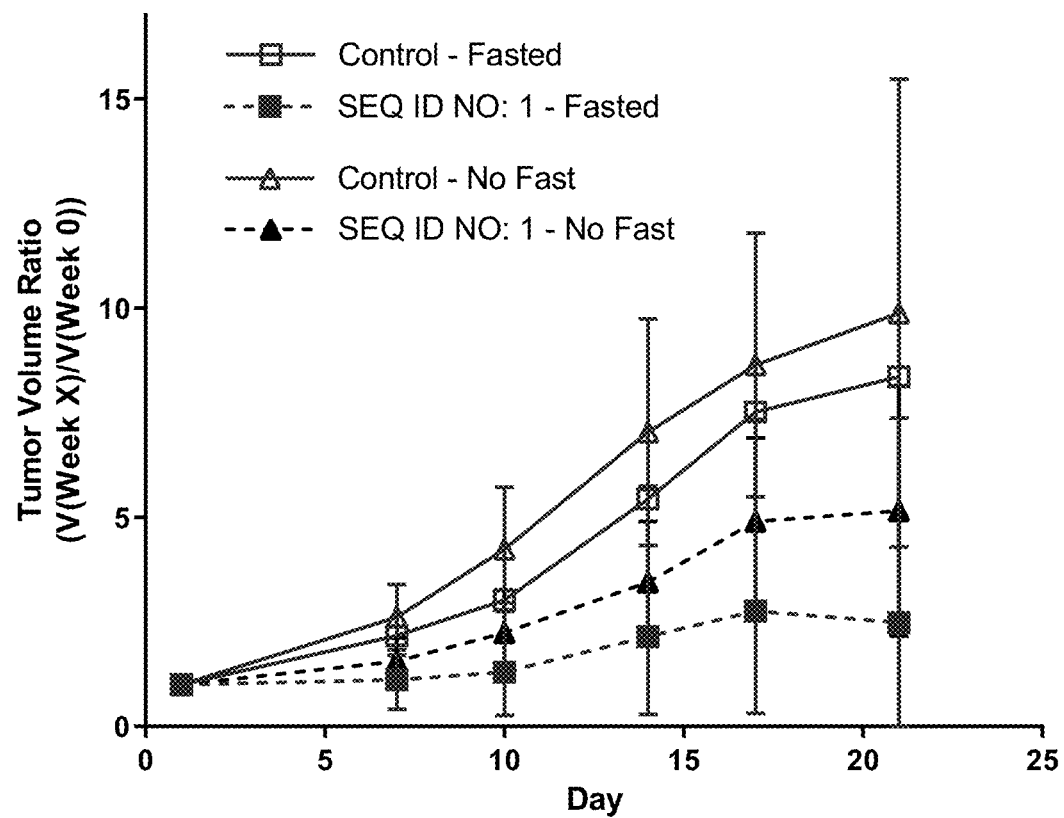
FIG. 7 shows tumor volume ratios in HCT-116 bearing nude mice.

Tumor dimensions were measured before the testing using calipers and the tumor volume approximated using the formula given above. Tumor volume ratio (TVR) is defined as the ratio of the volume of the tumor at day X over the volume of the tumor at day 0. The mice were injected subcutaneously with either vehicle, 150 μg/kg of SEQ ID NO: 1, or 2.5 U/kg of conventional NPH insulin every day for 6 consecutive days followed by 1 day with no injection for a total of 3 weeks and subject to between 8 and 10 hours a day of fasting. As controls, parallel groups of treated and untreated mice were left unfasted. Tumor volume was measured before and after the testing and the measurements are shown in Table 7. Tumor volume ratio (TVR) is shown in FIG. 7.

TABLE 7

HCT-116 tumor volume ratio (TVR), SEQ ID NO: 1 treated and controls, fasted and unfasted and fasted NPH

|  | Volume Before | Volume After | Comparison Result (treated vs. controls) |
|---|---|---|---|
| Fasted treated (SEQ ID NO: 1) | 158.3 | 505.6 | 62 ± 19% lower TVR for SEQ ID NO: 1 treated group vs. fasted controls, p < 0.02 |
| Fasted controls | 157.6 | 1279.6 | |
| Fasted NPH | 157.2 | 1073.9 | Change not significant against fasted controls |
| Unfasted treated (SEQ ID NO: 1) | 163.8 | 887.4 | 48% ± 14% lower TVR for SEQ ID NO: 1 treated vs. unfasted controls, p < 0.02 |
| Unfasted controls | 154.9 | 1542.7 | |

Example 9b: Tumor Volume in HCT-116 Xenograft Models in Nude Mice

HCT-116 cells are cultured under aseptic conditions at 37° C. with 5% CO2 in logarithmic growth phase. On the day of the inoculations, the cells are harvested, washed in PBS, and resuspended at the appropriate concentration in a serum-free medium:matrigel (1:1 vol:vol) mixture. Inoculations are carried out in conscious naïve, nude mice (n=60 females) while being manually restrained. Mice are injected subcutaneously (SC) on their dorsal right flank with 2×106 cells using a 28 G needle in 200 μL volume. The injection areas are monitored until the tumors are visible/palpable. Once palpable, calipers are used for tumor measurements twice a week. The greatest longitudinal diameter (length) and the greatest transverse diameter (width) is used to determine tumor volume according to the equation:

$$\text{Tumor volume} = \frac{(\text{length} \times \text{width}^2)}{2}.$$

Once the tumors reach a volume between 100 and 300 mm$^3$, mice bearing HCT-116 tumors are randomized into four groups according to Table 8.

TABLE 8

Test groups for HCT-116 bearing nude mice

|  | Fasted 8-10 hours per day | Unfasted |
|---|---|---|
| Vehicle | fasted controls | unfasted controls |
| Insulin-Fc fusion protein | fasted treated | unfasted treated |

Tumor dimensions are measured before the testing using calipers and the tumor volume approximated using the formula given above. Tumor volume ratio (TVR) is defined as the ratio of the volume of the tumor at day X over the volume of the tumor at day 0. The mice are injected subcutaneously with either vehicle, 150 μg/kg of the insulin-Fc fusion proteins of SEQ ID NO: 3, SEQ ID NO: 18, SEQ ID NO: 20, SEQ ID NO: 22, SEQ ID NO: 24, SEQ ID NO: 26, or SEQ ID NO: 28, or 2.5 U/kg of conventional NPH insulin every day for 6 consecutive days followed by 1 day with no injection for a total of 3 weeks and subject to between 8 and 10 hours a day of fasting. As controls, parallel groups of treated and untreated mice are left unfasted. Tumor volume is measured before and after the testing. It is expected that the tumor volume ratio (TVR) for mice injected with the insulin-Fc fusion proteins of SEQ ID NO: 18, SEQ ID NO: 20, SEQ ID NO: 22, or SEQ ID NO: 24 compared to the fasted control group will be at least 40% lower. It is expected that the tumor volume ratio (TVR) for mice injected with the insulin-Fc fusion proteins of SEQ ID NO: 18, SEQ ID NO: 20, SEQ ID NO: 22, or SEQ ID NO: 24 compared to the no fasting control group will be at least 30% lower. It is expected that the tumor volume ratio (TVR) for mice injected with the insulin-Fc fusion proteins of SEQ ID NO: 18, SEQ ID NO: 20, SEQ ID NO: 22, or SEQ ID NO: 24 compared to the no fasting control group will be at least 30% lower. It is expected that the tumor volume ratio (TVR) for mice injected with the insulin-Fc fusion proteins of SEQ ID NO: 3, SEQ ID NO: 26, or SEQ ID NO: 28 will remain similar to the fasting control group and the no fasting control group.

Example 10a: Tumor Volume in Metastatic Human Melanoma Cell Line (WM266.4)

WM266.4 cells were cultured under aseptic conditions at 37° C. with 5% $CO_2$ in logarithmic growth phase. On the day of the inoculations, the cells were harvested, washed in PBS, and resuspended at the appropriate concentration in a serum-free medium:matrigel (1:1 vol:vol) mixture. Inoculations were carried out in conscious Naïve, nude mice (n=60 females) while being manually restrained. Mice were injected subcutaneously (SC) on their dorsal right flank with $2 \times 10^6$ cells using a 28 G needle in 200 µl volume. The injection areas were monitored until the tumors were visible/palpable. Once palpable, calipers were used for tumor measurements twice a week. The greatest longitudinal diameter (length) and the greatest transverse diameter (width) was used to determine tumor volume according to the equation:

$$\text{Tumor volume} = \frac{(\text{length} \times \text{width}^2)}{2}.$$

Once the tumors reach a volume between 100 and 300 mm³, mice bearing WM266.4 tumors were randomized into four groups according to Table 9.

TABLE 9

Test groups for WM266.4 bearing nude mice

|  | Fasted 8-10 hours per day | Unfasted |
|---|---|---|
| Vehicle | fasted controls | unfasted controls |
| Insulin-Fc fusion protein | fasted treated | unfasted treated |

Figure 8:
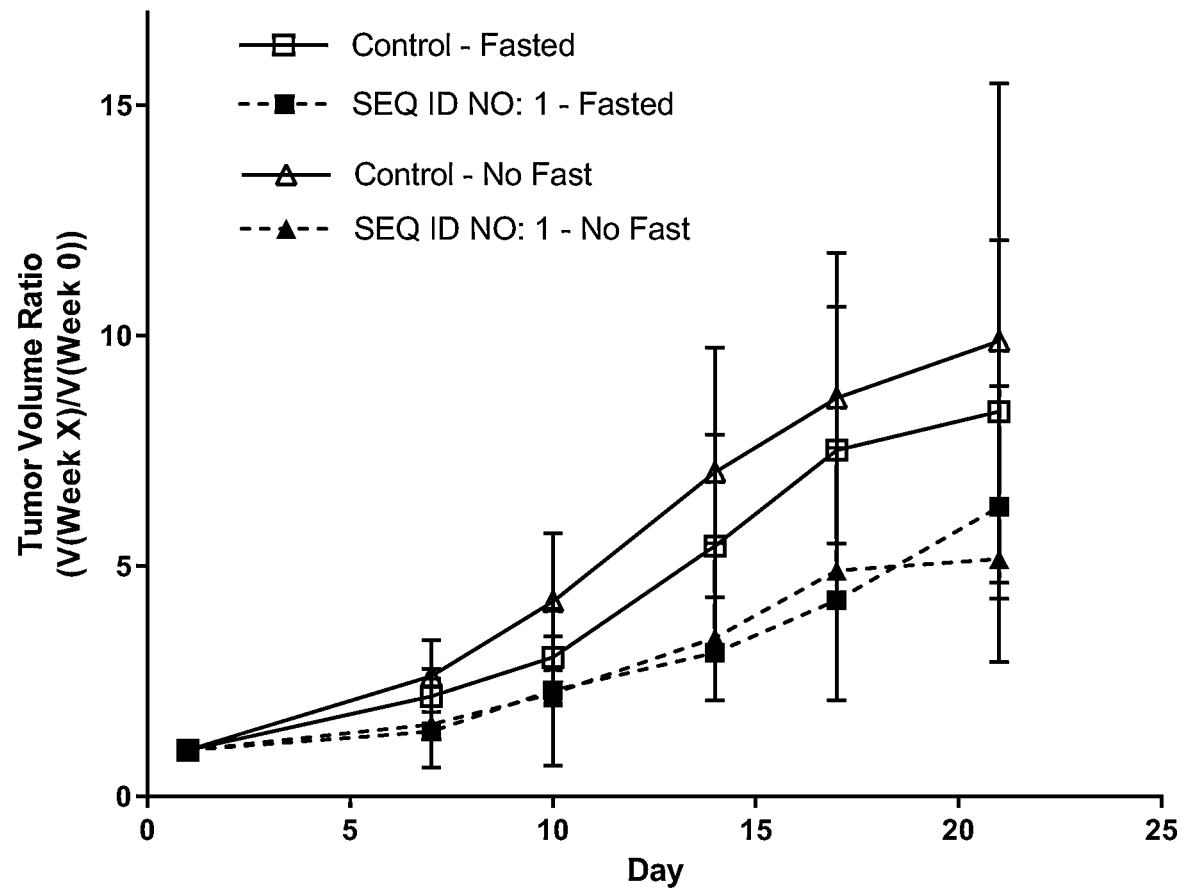
FIG. 8 shows tumor volume ratios in WM266.4 bearing nude mice.

Tumor dimensions were measured before the testing using calipers and the tumor volume approximated using the formula given above. Tumor volume ratio (TVR) is defined as the ratio of the volume of the tumor at day X over the volume of the tumor at day 0. The mice were injected subcutaneously with either vehicle or 150 µg/kg of SEQ ID NO: 1, every day for 6 consecutive days followed by 1 day with no injection for a total of 3 weeks and were subject to between 8 and 10 hours a day of fasting. As controls, parallel groups of treated and untreated mice were left unfasted. Tumor volume was measured before and after the testing and the measurements are shown in Table 10. Tumor volume ratio (TVR) is shown in FIG. 8.

TABLE 10

WM266.4 tumor volume ratio, SEQ ID NO: 1 treated and controls, fasted and unfasted

|  | Volume Before | Volume After | Comparison Result (treated vs. controls) |
|---|---|---|---|
| Fasted treated (SEQ ID NO: 1) | 148.1 | 1156.6 | 62 ± 19% lower TVR for SEQ ID NO: 1 treated vs. fasted controls, p < 0.02 |
| Fasted controls | 146.3 | 1685.9 |  |
| Unfasted treated (SEQ ID NO: 1) | 149.2 | 981.9 | 48% ± 14% lower TVR for SEQ ID NO: 1 treated vs. unfasted controls, p < 0.02 |
| Unfasted controls | 146.3 | 1685.9 |  |

Example 10b: Tumor Volume in Metastatic Human Melanoma Cell Line (WM266.4)

WM266.4 cells are cultured under aseptic conditions at 37° C. with 5% CO2 in logarithmic growth phase. On the day of the inoculations, the cells are harvested, washed in PBS, and resuspended at the appropriate concentration in a serum-free medium:matrigel (1:1 vol:vol) mixture. Inoculations are carried out in conscious Naïve, nude mice (n=60 females) while being manually restrained. Mice are injected subcutaneously (SC) on their dorsal right flank with $2 \times 10^6$ cells using a 28 G needle in 200 µl volume. The injection areas are monitored until the tumors were visible/palpable. Once palpable, calipers are used for tumor measurements twice a week. The greatest longitudinal diameter (length) and the greatest transverse diameter (width) is used to determine tumor volume according to the equation:

$$\text{Tumor volume} = \frac{(\text{length} \times \text{width}^2)}{2}.$$

Once the tumors reach a volume between 100 and 300 mm³, mice bearing WM266.4 tumors are randomized into four groups according to Table 11.

TABLE 11

Test groups for WM266.4 bearing nude mice

|  | Fasted 8-10 hours per day | Unfasted |
|---|---|---|
| Vehicle | fasted controls | unfasted controls |
| Insulin-Fc fusion protein | fasted treated | unfasted treated |

Tumor dimensions are measured before the testing using calipers and the tumor volume approximated using the formula given above. Tumor volume ratio (TVR) is defined as the ratio of the volume of the tumor at day X over the volume of the tumor at day 0. The mice are injected subcutaneously with either vehicle, 150 µg/kg of the insulin-Fc fusion proteins of SEQ ID NO: 3, SEQ ID NO: 18, SEQ ID NO: 20, SEQ ID NO: 22, SEQ ID NO: 24, SEQ ID NO: 26 or SEQ ID NO: 28, every day for 6 consecutive days followed by 1 day with no injection for a total of 3 weeks and are subject to between 8 and 10 hours a day of fasting. As controls, parallel groups of treated and untreated mice are left unfasted. Tumor volume is measured before and after the testing. It is expected that the tumor volume ratio (TVR) for mice injected with the insulin-Fc fusion proteins of SEQ ID NO: 18, SEQ ID NO: 20, SEQ ID NO: 22, or SEQ ID NO: 24 compared to the fasted control group will be at least 40% lower. It is expected that the tumor volume ratio (TVR) for mice injected with the insulin-Fc fusion proteins of SEQ ID NO: 18, SEQ ID NO: 20, SEQ ID NO: 22, or SEQ ID NO: 24 compared to the no fasting control group will be at least 30% lower. It is expected that the tumor volume ratio (TVR) for mice injected with the insulin-Fc fusion proteins of SEQ ID NO: 3, SEQ ID NO: 26, or SEQ ID NO: 28 will remain similar to the fasting control group and the no fasting control group.

Example 11: Tumor Volume in Human Breast Cancer Cell Line (MCF-7L) and Tamoxifen-Resistant Breast Cancer Cell Line (MCF-7L TamR) In Vivo without Fasting MCF-7L or MCF-7L TamR (TamR=tamoxifen resistant) cells differ from each other in that MCF-7L cells express significant IR and IGF1R on their cell surfaces, whereas MCF-7L TamR cells express very low levels of IGF1R and significant levels of IR on their cell surfaces as measured by Western Blot techniques. These cells are cultured under aseptic conditions at 37° C. with 5% CO2 in logarithmic growth phase. On the day of the inoculations, the cells are harvested, washed in PBS, and resuspended at the appropriate concentration in a serum-free medium. Mice are implanted bilaterally into the second mammary fat pads of female nude mice, using $1 \times 10^6$ cells per implantation. Mice are implanted on both the left and right sides. The injection areas are monitored until the tumors were visible/palpable. Once palpable, calipers are used for tumor measurements twice a week. The greatest longitudinal diameter (length) and the greatest transverse diameter (width) are used to determine tumor volume according to the equation:

$$\text{Tumor volume} = \frac{(\text{length} \times \text{width}^2)}{2}.$$

Once the tumors reach a volume between 100 and 300 mm$^3$, mice bearing MCF-7L tumors are randomized into groups according to Table 12.

TABLE 12

Test groups for MCF-7L bearing nude mice

|  | Fasted 8-10 hours per day | Unfasted |
|---|---|---|
| Vehicle | fasted controls | unfasted controls |
| Insulin-Fc fusion protein | fasted treated | unfasted treated |

Tumor dimensions are measured before the testing using calipers and the tumor volume approximated using the formula given above. Tumor volume ratio (TVR) is defined as the ratio of the volume of the tumor at week X over the volume of the tumor at week 0. The mice are injected subcutaneously with either vehicle or 100-200 µg/kg of SEQ ID NO: 1, SEQ ID NO: 3, SEQ ID NO: 18, SEQ ID NO: 20, SEQ ID NO: 22, SEQ ID NO: 24, SEQ ID NO: 26 or SEQ ID NO: 28 3× per week for up to 8 weeks. Vehicle and treated group tumor volume is measured before and after the testing and the expected measurements are shown in Table 13, with treatments using SEQ ID NO: 1, SEQ ID NO: 18, SEQ ID NO: 20, SEQ ID NO: 22, and SEQ ID NO: 24 are expected to show significant effects both alone and in combination with tamoxifen treatment.

SEQ ID NO: 1, SEQ ID NO: 18, SEQ ID NO: 20, SEQ ID NO: 22, and SEQ ID NO: 24 are referred to as Group A in Table 13, and SEQ ID NO: 3, SEQ ID NO: 26, and SEQ ID NO: 28 are referred to as Group B in Table 13.

TABLE 13

Test groups and expected outcomes for MCF-7L bearing nude mice using SEQ ID Nos. 1 and 3, tamoxifen, or vehicle; no fasting. Vehicle is PBS or peanut oil. Tam = tamoxifen

| Treatment ID | Treatment Combination | SEQ ID NO/ Dose (ug/kg) | Expected Result for TVR (Week8/ Week0)# as compared to Vehicle/Vehicle | Expected Result for TVR (Week8/ Week0)# as compared to Vehicle/Tam |
|---|---|---|---|---|
| A | Vehicle (PBS)/ Vehicle (peanut oil) | N/A | 1 | 0 |
| B | Vehicle (PBS)/ Tam | N/A | 3 | 4 |
| C | Group A/Vehicle | 100 | 2 | 0 |
| D | Group A/Tam | 100 | 3 | 5 |
| E | Group A/Vehicle | 200 | 2 | 0 |
| F | Group A/Tam | 200 | 3 | 6 |
| G | Group B/Vehicle | 200 | * | * |
| H | Group B/Tam | 200 | * | * |

0 = increased TVR versus vehicle control, 1 = no change versus Vehicle/Vehicle; 2 = small TVR reduction versus Vehicle/Vehicle; 3 = significant TVR reduction versus Vehicle/Vehicle; 4 = no change versus Vehicle/Tam, 5 = small TVR reduction versus Vehicle/Tam, 6 = significant TVR reduction versus Vehicle/Tam.

* = mice expected to be culled from study due to significant hypoglycemia; not able to complete study.

MCF-7L TamR tumors are also studied in vivo by implanting MCF-7L TamR cells in vivo into female nude mice as described above. Once the tumors reach a volume between 100 and 300 mm$^3$, mice bearing MCF-7L TamR tumors are randomized into groups according to Table 12 in a separate study. Tumor dimensions are measured before the testing using calipers and the tumor volume approximated using the formula given above. Tumor volume ratio (TVR) is defined as the ratio of the volume of the tumor at week X over the volume of the tumor at week 0. The mice are injected subcutaneously with either vehicle or 100-200 µg/kg of SEQ ID NO: 1, SEQ ID NO: 3, 3× per week for up to 8 weeks. Vehicle and treated group tumor volume is measured before and after the testing and the expected measurements are shown in Table 14, with SEQ ID NO: 1 treatment expected to show significant effects as compared to tamoxifen treatment alone. This is expected since MCF-7L TamR cells are tamoxifen resistant and therefore tamoxifen treatment alone should have little to no impact on tumor growth, whereas SEQ ID NO: 1 treatment, particularly at higher doses is expected to downregulate the insulin receptor on MCF-7L TamR cells resulting in slower tumor growth and lower TVR as compared to tamoxifen treatment alone.

TABLE 14

Test groups and expected outcomes for MCF-7L TamR bearing nude mice using SEQ ID NOs. 1 and 3, tamoxifen, or vehicle; no fasting. Vehicle is PBS or peanut oil. Tam = tamoxifen

| Treatment ID | Treatment Combination | SEQ ID NO. Dose (ug/kg) | Expected Result for TVR (Week8/Week0)# as compared to Vehicle/Vehicle |
|---|---|---|---|
| I | Vehicle/Tam | N/A | 4 |
| J | Group A/Tam | 100 | 5 |
| K | Group A/Tam | 200 | 6 |

0 = increased TVR versus vehicle control (undesirable), 4 = no change versus Vehicle/Tam, 5 = small TVR reduction versus Vehicle/Tam, 6 = significant TVR reduction versus Vehicle/Tam.

Example 12: Exemplary Insulin-Fc Fusion Protein Domains and Sequences

Exemplary insulin-Fc fusion protein domains and sequences used in the above Examples are shown in Table A and FIG. 2 and FIG. 3.

EQUIVALENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprise(s)," "comprising," "contain(s)," and "containing" are intended to be open and the use thereof permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

SEQUENCE LISTING

```
Sequence total quantity: 41
SEQ ID NO: 1            moltype = AA   length = 292
FEATURE                 Location/Qualifiers
source                  1..292
                        mol_type = protein
                        organism = synthetic construct
SEQUENCE: 1
FVNQHLCGSD LVEALALVCG ERGFFYTDPT GGGPRRGIVE QCCHSICSLY QLENYCNGGG   60
GAGGGGDKTH TCPPCPAPEL LGGPSVFLFP PKPKDTLMIS RTPEVTCVVV DVSHEDPEVK  120
FNWYVDGVEV HNAKTKPREE QYNSTYRVVS VLTVLHQDWL NGKEYKCKVS NKALPAPIEK  180
TISKAKGQPR EPQVYTLPPS RDELTKNQVS LTCLVKGFYP SDIAVEWESN GQPENNYKTT  240
PPVLDSDGSF FLYSKLTVDK SRWQQGNVFS CSVMHEALHN HYTQKSLSLS PG          292

SEQ ID NO: 2            moltype = DNA  length = 936
FEATURE                 Location/Qualifiers
source                  1..936
                        mol_type = other DNA
                        organism = synthetic construct
SEQUENCE: 2
atggaatgga gctgggtctt tctcttcttc ctgtcagtaa cgactggtgt ccactccttc   60
gtgaaccagc acctgtgcgg ctccgacctg gtggaagctc tggctctcgt gtgcggcgag  120
cggggcttct tctacaccga tcccactgga ggcggtccac gcagaggcat cgtggaacag  180
tgctgccact ccatctgctc cctgtaccag ctggaaaact actgcaatgg cggaggtggt  240
gcaggaggcg gtggagacaa aactcacaca tgcccaccgt gcccagcacc tgaactcctg  300
gggggaccgt cagtcttcct cttccccccca aaacccaagg acaccctcat gatctcccgg  360
acccctgagg tcacatgcgt ggtggtggac gtgagccacg aagaccctga ggtcaagttc  420
aactggtacg tggacggcgt ggaggtgcat aatgccaaga caaagccgcg ggaggagcag  480
tacaacagca cgtaccgtgt ggtcagcgtc ctcaccgtcc tgcaccagga ctggctgaat  540
ggcaaggagt acaagtgcaa ggtctccaac aaagccctcc cagcccccat cgagaaaacc  600
atctccaaag ccaaagggca gccccgagaa ccacaggtgt acaccctgcc cccatcccgg  660
gatgagctga ccaagaacca ggtcagcctg acctgcctgg tcaaaggctt ctatcccagc  720
gacatcgccg tggagtggga gagcaatggg cagccggaga acaactacaa gaccacgcct  780
cccgtgctgg actccgacgg ctccttcttc ctctacagca agctcaccgt ggacaagagc  840
aggtggcagc agggaacgt cttctcatgc tccgtgatgc atgaggctct gcacaaccac  900
tacacgcaga agagcctctc cctgtctccg ggttag                            936
```

```
SEQ ID NO: 3           moltype = AA  length = 304
FEATURE                Location/Qualifiers
source                 1..304
                       mol_type = protein
                       organism = synthetic construct
SEQUENCE: 3
FVNQHLCGSH LVEALELVCG ERGFHYGGGG GGSGGGGGIV EQCCTSTCSL DQLENYCGGG    60
GGQGGGGQGG GGQGGGGGDK THTCPPCPAP ELLGGPSVFL FPPKPKDTLM ISRTPEVTCV   120
VVDVSHEDPE VKFNWYVDGV EVHNAKTKPR EEQYNSTYRV VSVLTVLHQD WLNGKEYKCK   180
VSNKALPAPI EKTISKAKGQ PREPQVYTLP PSRDELTKNQ VSLTCLVKGF YPSDIAVEWE   240
SNGQPENNYK TTPPVLDSDG SFFLYSKLTV DKSRWQQGNV FSCSVMHEAL HNHYTQKSLS   300
LSPG                                                                304

SEQ ID NO: 4           moltype = DNA  length = 972
FEATURE                Location/Qualifiers
source                 1..972
                       mol_type = other DNA
                       organism = synthetic construct
SEQUENCE: 4
atggaatgga gctgggtctt tctcttcttc ctgtcagtaa cgactggtgt ccactccttc    60
gtgaaccagc acctgtgcgg ctcccacctg gtggaagctc tggaactcgt gtgcggcgag   120
cggggcttcc actacggggg tggcggagga ggttctggtg gcggcggagg catcgtggaa   180
cagtgctgca cctccacctg ctccctggac cagctggaaa actactgcgg tggcggaggt   240
ggtcaaggag gcggtggaca gggtggaggt gggcaggagg gaggcggggg agacaaaact   300
cacacatgcc caccgtgccc agcacctgaa ctcctgggag gaccgtcagt cttcctcttc   360
cccccaaaac ccaaggacac cctcatgatc tcccggaccc ctgaggtcac atgcgtggtg   420
gtggacgtga gccacgaaga ccctgaggtc aagttcaact ggtacgtgga cggcgtggag   480
gtgcataatg ccaagacaaa gccgcgggag gagcagtaca acagcacgta ccgtgtggtc   540
agcgtcctca ccgtcctgca ccaggactgg ctgaatggca aggagtacaa gtgcaaggtc   600
tccaacaaag ccctcccagc ccccatcgag aaaaccatct ccaaagccaa agggcagccc   660
cgagaaccac aggtgtacac cctgccccca tcccgggatg agctgaccaa gaaccaggtc   720
agcctgacct gcctggtcaa aggcttctat cccagcgaca tcgccgtgga gtgggagagc   780
aatgggcagc cggagaacaa ctacaagacc acgcctcccg tgctggactc cgacggctcc   840
ttcttcctct acagcaagct caccgtggac aagagcaggt ggcagcaggg gaacgtcttc   900
tcatgctccg tgatgcatga ggctctgcac aaccactaca cgcagaagag cctctccctg   960
tctccgggtt ag                                                       972

SEQ ID NO: 5           moltype = AA  length = 51
FEATURE                Location/Qualifiers
source                 1..51
                       mol_type = protein
                       organism = Homo sapiens
SEQUENCE: 5
FVNQHLCGSH LVEALYLVCG ERGFFYTPKT GIVEQCCTSI CSLYQLENYC N             51

SEQ ID NO: 6           moltype = AA  length = 57
FEATURE                Location/Qualifiers
source                 1..57
                       mol_type = protein
                       organism = synthetic construct
SEQUENCE: 6
FVNQHLCGSD LVEALALVCG ERGFFYTDPT GGGPRRGIVE QCCHSICSLY QLENYCN       57

SEQ ID NO: 7           moltype = AA  length = 30
FEATURE                Location/Qualifiers
source                 1..30
                       mol_type = protein
                       organism = synthetic construct
SEQUENCE: 7
FVNQHLCGSD LVEALALVCG ERGFFYTDPT                                     30

SEQ ID NO: 8           moltype = AA  length = 26
FEATURE                Location/Qualifiers
source                 1..26
                       mol_type = protein
                       organism = synthetic construct
SEQUENCE: 8
FVNQHLCGSH LVEALELVCG ERGFHY                                         26

SEQ ID NO: 9           moltype = AA  length = 6
FEATURE                Location/Qualifiers
source                 1..6
                       mol_type = protein
                       organism = synthetic construct
SEQUENCE: 9
GGGPRR                                                                6
```

```
SEQ ID NO: 10            moltype = AA   length = 11
FEATURE                  Location/Qualifiers
source                   1..11
                         mol_type = protein
                         organism = synthetic construct
SEQUENCE: 10
GGGGGGSGGG G                                                          11

SEQ ID NO: 11            moltype = AA   length = 21
FEATURE                  Location/Qualifiers
source                   1..21
                         mol_type = protein
                         organism = synthetic construct
SEQUENCE: 11
GIVEQCCHSI CSLYQLENYC N                                               21

SEQ ID NO: 12            moltype = AA   length = 20
FEATURE                  Location/Qualifiers
source                   1..20
                         mol_type = protein
                         organism = synthetic construct
SEQUENCE: 12
GIVEQCCTST CSLDQLENYC                                                 20

SEQ ID NO: 13            moltype = AA   length = 9
FEATURE                  Location/Qualifiers
source                   1..9
                         mol_type = protein
                         organism = synthetic construct
SEQUENCE: 13
GGGGAGGGG                                                              9

SEQ ID NO: 14            moltype = AA   length = 21
FEATURE                  Location/Qualifiers
source                   1..21
                         mol_type = protein
                         organism = synthetic construct
SEQUENCE: 14
GGGGGQGGGG QGGGGQGGGG G                                               21

SEQ ID NO: 15            moltype = AA   length = 226
FEATURE                  Location/Qualifiers
source                   1..226
                         mol_type = protein
                         organism = Homo sapiens
SEQUENCE: 15
DKTHTCPPCP APELLGGPSV FLFPPKPKDT LMISRTPEVT CVVVDVSHED PEVKFNWYVD      60
GVEVHNAKTK PREEQYNSTY RVVSVLTVLH QDWLNGKEYK CKVSNKALPA PIEKTISKAK     120
GQPREPQVYT LPPSRDELTK NQVSLTCLVK GFYPSDIAVE WESNGQPENN YKTTPPVLDS     180
DGSFFLYSKL TVDKSRWQQG NVFSCSVMHE ALHNHYTQKS LSLSPG                    226

SEQ ID NO: 16            moltype = AA   length = 19
FEATURE                  Location/Qualifiers
source                   1..19
                         mol_type = protein
                         organism = synthetic construct
SEQUENCE: 16
MEWSWVFLFF LSVTTGVHS                                                  19

SEQ ID NO: 17            moltype = DNA   length = 57
FEATURE                  Location/Qualifiers
source                   1..57
                         mol_type = other DNA
                         organism = synthetic construct
SEQUENCE: 17
atggaatgga gctgggtctt tctcttcttc ctgtcagtaa cgactggtgt ccactcc         57

SEQ ID NO: 18            moltype = AA   length = 297
FEATURE                  Location/Qualifiers
source                   1..297
                         mol_type = protein
                         organism = synthetic construct
SEQUENCE: 18
FVNQHLCGSD LVEALALVCG ERGFFYTDPT GGGPRRGIVE QCCHSICSLY QLENYCNGGG      60
GAGGGGAGGG GDKTHTCPPC PAPELLGGPS VFLFPPKPKD TLMISRTPEV TCVVVDVSHE     120
DPEVKFNWYV DGVEVHNAKT KPREEQYNST YRVVSVLTVL HQDWLNGKEY KCKVSNKALP     180
APIEKTISKA KGQPREPQVY TLPPSRDELT KNQVSLTCLV KGFYPSDIAV EWESNGQPEN     240
NYKTTPPVLD SDGSFFLYSK LTVDKSRWQQ GNVFSCSVMH EALHNHYTQK SLSLSPG        297
```

```
SEQ ID NO: 19           moltype = DNA  length = 951
FEATURE                 Location/Qualifiers
source                  1..951
                        mol_type = other DNA
                        organism = synthetic construct
SEQUENCE: 19
atggaatgga gctgggtctt tctcttcttc ctgtcagtaa cgactggtgt ccactccttc    60
gtgaaccagc acctgtgcgg ctccgacctg gtggaagctc tggctctcgt gtgcggcgag   120
cggggcttct tctacaccga tcccactgga ggcggtccac gcagaggcat cgtggaacag   180
tgctgccact ccatctgctc cctgtaccag ctggaaaact actgcaatgg tggcggagga   240
gctggcggag gtggtgcagg aggcggtgga gacaaaactc acacatgccc accgtgccca   300
gcacctgaac tcctgggggg accgtcagtc ttcctcttcc ccccaaaacc caaggacacc   360
ctcatgatct cccggacccc tgaggtcaca tgcgtggtgg tggacgtgag ccacgaagac   420
cctgaggtca agttcaactg gtacgtggac ggcgtggagg tgcataatgc caagacaaag   480
ccgcgggagg agcagtacaa cagcacgtac cgtgtggtca gcgtcctcac cgtcctgcac   540
caggactggc tgaatggcaa ggagtacaag tgcaaggtct ccaacaaagc cctcccagcc   600
cccatcgaga aaaccatctc caaagccaaa gggcagccce gagaaccaca ggtgtacacc   660
ctgcccccat cccgggatga gctgaccaag aaccaggtca gcctgacctg cctggtcaaa   720
ggcttctatc ccagcgacat cgccgtggag tgggagagca atgggcagcc ggagaacaac   780
tacaagacca cgcctcccgt gctggactcc gacggctcct tcttcctcta cagcaagctc   840
accgtggaca agagcaggtg gcagcagggg aacgtcttct catgctccgt gatgcatgag   900
gctctgcaca accactacac gcagaagagc ctctccctgt ctccgggtta g             951

SEQ ID NO: 20           moltype = AA  length = 291
FEATURE                 Location/Qualifiers
source                  1..291
                        mol_type = protein
                        organism = synthetic construct
SEQUENCE: 20
FVNQHLCGSD LVEALALVCG ERGFFYTDPT GGGPRRGIVE QCCHSICSLY QLENYCGGGG     60
AGGGGDKTHT CPPCPAPELL GGPSVFLFPP KPKDTLMISR TPEVTCVVVD VSHEDPEVKF    120
NWYVDGVEVH NAKTKPREEQ YNSTYRVVSV LTVLHQDWLN GKEYKCKVSN KALPAPIEKT    180
ISKAKGQPRE PQVYTLPPSR DELTKNQVSL TCLVKGFYPS DIAVEWESNG QPENNYKTTP    240
PVLDSDGSFF LYSKLTVDKS RWQQGNVFSC SVMHEALHNH YTQKSLSLSP G             291

SEQ ID NO: 21           moltype = DNA  length = 933
FEATURE                 Location/Qualifiers
source                  1..933
                        mol_type = other DNA
                        organism = synthetic construct
SEQUENCE: 21
atggaatgga gctgggtctt tctcttcttc ctgtcagtaa cgactggtgt ccactccttc    60
gtgaaccagc acctgtgcgg ctccgacctg gtggaagctc tggctctcgt gtgcggcgag   120
cggggcttct tctacaccga tcccactgga ggcggtccac gcagaggcat cgtggaacag   180
tgctgccact ccatctgctc cctgtaccag ctggaaaact actgcggcgg aggtggtgca   240
ggaggcggtg gagacaaaac tcacacatgc ccaccgtgcc cagcacctga actcctgggg   300
ggaccgtcag tcttcctctt ccccccaaaa cccaaggaca ccctcatgat ctcccggacc   360
cctgaggtca catgcgtggt ggtggacgtg agccacgaag accctgaggt caagttcaac   420
tggtacgtgg acggcgtgga ggtgcataat gccaagacaa agccgcggga ggagcagtac   480
aacagcacgt accgtgtggt cagcgtcctc accgtcctgc accaggactg gctgaatggc   540
aaggagtaca agtgcaaggt ctccaacaaa gccctcccag cccccatcga aaaccatctc   600
caaagccaaa gggcagcccc gagaaccagg tgtacaccct gccccccatc ccgggat      660
gagctgacca agaaccaggt cagcctgacc tgcctggtca aaggcttcta tcccagcgac   720
atcgccgtgg agtgggagag caatgggcag ccggagaaca actacaagac cacgcctccc   780
gtgctggact ccgacggctc cttcttcctc tacagcaagc tcaccgtgga caagagcagg   840
tggcagcagg ggaacgtctt ctcatgctcc gtgatgcatg aggctctgca caaccactac   900
acgcagaaga gcctctccct gtctccgggt tag                                933

SEQ ID NO: 22           moltype = AA  length = 287
FEATURE                 Location/Qualifiers
source                  1..287
                        mol_type = protein
                        organism = synthetic construct
SEQUENCE: 22
FVNQHLCGSD LVEALALVCG ERGFFYTDPT GGGPRRGIVE QCCHSICSLY QLENYCGGG     60
GDKTHTCPPC PAPELLGGPS VFLFPPKPKD TLMISRTPEV TCVVVDVSHE DPEVKFNWYV   120
DGVEVHNAKT KPREEQYNST YRVVSVLTVL HQDWLNGKEY KCKVSNKALP APIEKTISKA   180
KGQPREPQVY TLPPSRDELT KNQVSLTCLV KGFYPSDIAV EWESNGQPEN NYKTTPPVLD   240
SDGSFFLYSK LTVDKSRWQQ GNVFSCSVMH EALHNHYTQK SLSLSPG                  287

SEQ ID NO: 23           moltype = DNA  length = 921
FEATURE                 Location/Qualifiers
source                  1..921
                        mol_type = other DNA
                        organism = synthetic construct
SEQUENCE: 23
atggaatgga gctgggtctt tctcttcttc ctgtcagtaa cgactggtgt ccactccttc    60
gtgaaccagc acctgtgcgg ctccgacctg gtggaagctc tggctctcgt gtgcggcgag   120
```

```
cggggcttct tctacaccga tcccactgga ggcggtccac gcagaggcat cgtggaacag    180
tgctgccact ccatctgctc cctgtaccag ctggaaaaact actgcaatgg aggcggtgga   240
gacaaaactc acacatgccc accgtgccca gcacctgaac tcctggggggg accgtcagtc   300
ttcctcttcc ccccaaaacc caaggacacc ctcatgatct cccggacccc tgaggtcaca    360
tgcgtggtgg tggacgtgag ccacgaagac cctgaggtca agttcaactg gtacgtggac    420
ggcgtggagg tgcataatgc caagacaaag ccgcgggagg agcagtacaa cagcacgtac    480
cgtgtggtca gcgtcctcac cgtcctgcac caggactggc tgaatggcaa ggagtacaag    540
tgcaaggtct ccaacaaagc cctcccagcc cccatcgaga aaaccatctc caaagccaaa    600
gggcagcccc gagaaccaca ggtgtacacc ctgcccccat cccgggatga gctgaccaag    660
aaccaggtca gcctgacctg cctggtcaaa ggcttctatc ccagcgacat cgccgtggag    720
tgggagagca atgggcagcc ggagaacaac tacaagacca cgcctcccgt gctggactcc    780
gacggctcct tcttcctcta cagcaagctc accgtggaca gagcaggtg gcagcagggg     840
aacgtcttct catgctccgt gatgcatgag gctctgcaca accactacac gcagaagagc    900
ctctcccctgt ctccggggtta g                                            921

SEQ ID NO: 24         moltype = AA  length = 283
FEATURE               Location/Qualifiers
source                1..283
                      mol_type = protein
                      organism = synthetic construct
SEQUENCE: 24
FVNQHLCGSD LVEALALVCG ERGFFYTDPT GGGPRRGIVE QCCHSICSLY QLENYCNDKT     60
HTCPPCPAPE LLGGPSVFLF PPKPKDTLMI SRTPEVTCVV VDVSHEDPEV KFNWYVDGVE    120
VHNAKTKPRE EQYNSTYRVV SVLTVLHQDW LNGKEYKCKV SNKALPAPIE KTISKAKGQP    180
REPQVYTLPP SRDELTKNQV SLTCLVKGFY PSDIAVEWES NGQPENNYKT TPPVLDSDGS    240
FFLYSKLTVD KSRWQQGNVF SCSVMHEALH NHYTQKSLSL SPG                      283

SEQ ID NO: 25         moltype = DNA  length = 909
FEATURE               Location/Qualifiers
source                1..909
                      mol_type = other DNA
                      organism = synthetic construct
SEQUENCE: 25
atggaatgga gctgggtctt tctcttcttc ctgtcagtaa cgactggtgt ccactcctttc    60
gtgaaccagc acctgtgcgg ctccgacctg gtgaagctct ggctctcgt gtgcggcgag    120
cggggcttct tctacaccga tcccactgga ggcggtccac gcagaggcat cgtggaacag    180
tgctgccact ccatctgctc cctgtaccag ctggaaaaact actgcaatga caaaactcac   240
acatgcccac cgtgcccagc acctgaactc ctggggggac cgtcagtctt cctcttcccc    300
ccaaaaaccca aggacaccct catgatctcc cggacccctg aggtcacatg cgtggtggtg   360
gacgtgagcc acgaagaccc tgaggtcaag ttcaactggt acgtggacgg cgtggaggtg   420
cataatgcca agacaaagcc gcgggaggag cagtacaaca gcacgtaccg tgtggtcagc   480
gtcctcaccg tcctgcacca ggactggctg aatggcaagg agtacaagtg caaggtctcc   540
aacaaagccc tcccagcccc catcgagaaa accatctcca aagccaaagg gcagccccga   600
gaaccacagg tgtacaccct gcccccatcc cgggatgagc tgaccaagaa ccaggtcagc   660
ctgacctgcc tggtcaaagg cttctatccc agcgacatcg ccgtggagtg ggagagcaat   720
gggcagccgg agaacaacta caagaccacg cctcccgtgc tggactccga cggctccttc   780
ttcctctaca gcaagctcac cgtggacaag agcaggtgg agcaggggaa cgtcttctca   840
tgctccgtga tgcatgaggc tctgcacaac cactacacgc agaagagcct ctccctgtct   900
ccgggttag                                                            909

SEQ ID NO: 26         moltype = AA  length = 292
FEATURE               Location/Qualifiers
source                1..292
                      mol_type = protein
                      organism = synthetic construct
SEQUENCE: 26
FVNQHLCGSH LVEALALVCG ERGFFYTDPT GGGPRRGIVE QCCHSICSLY QLENYCGGG     60
GAGGGGDKTH TCPPCPAPEL LGGPSVFLFP PKPKDTLMIS RTPEVTCVVV DVSHEDPEVK    120
FNWYVDGVEV HNAKTKPREE QYNSTYRVVS VLTVLHQDWL NGKEYKCKVS NKALPAPIEK    180
TISKAKGQPR EPQVYTLPPS RDELTKNQVS LTCLVKGFYP SDIAVEWESN GQPENNYKTT    240
PPVLDSDGSF FLYSKLTVDK SRWQQGNVFS CSVMHEALHN HYTQKSLSLS PG            292

SEQ ID NO: 27         moltype = DNA  length = 936
FEATURE               Location/Qualifiers
source                1..936
                      mol_type = other DNA
                      organism = synthetic construct
SEQUENCE: 27
atggaatgga gctgggtctt tctcttcttc ctgtcagtaa cgactggtgt ccactcctttc    60
gtgaaccagc acctgtgcgg ctccgacctg gtgaagctct ggctctcgt gtgcggcgag    120
cggggcttct tctacaccga tcccactgga ggcggtccac gcagaggcat cgtggaacag    180
tgctgccact ccatctgctc cctgtaccag ctggaaaaact actgcaatgg cggaggtggt   240
gcaggaggcg gtgagacaa actcacacat gcccaccgt gcccagcacc tgaactcctg     300
ggggggaccg tcagtcttcc tcttcccccc aaaacccaag gacaccctca tgatctcccg    360
gacccctgag gtcacatgcg tggtggtgga cgtgagccac gaagaccctg aggtcaagtt   420
caactggtac gtggacggcg tggaggtgca taatgccaag acaaagccgc gggaggagca   480
gtacaacagc acgtaccgtg tggtcagcgt cctcaccgtc ctgcaccagg actggctgaa   540
tggcaaggag tacaagtgca aggtctccaa caaagccctc ccagcccccat cgagaaaacc   600
atctccaaag ccaaagggca gccccgagaa ccacaggtgt acaccctgcc ccatcccgg    660
```

```
gatgagctga ccaagaacca ggtcagcctg acctgcctgg tcaaaggctt ctatcccagc    720
gacatcgccg tggagtggga gagcaatggg cagccggaga acaactacaa gaccacgcct    780
cccgtgctgg actccgacgg ctccttcttc ctctacagca agctcaccgt ggacaagagc    840
aggtggcagc aggggaacgt cttctcatgc tccgtgatgc atgaggctct gcacaaccac    900
tacacgcaga agagcctctc cctgtctccg ggttag                              936

SEQ ID NO: 28           moltype = AA   length = 291
FEATURE                 Location/Qualifiers
source                  1..291
                        mol_type = protein
                        organism = synthetic construct
SEQUENCE: 28
FVNQHLCGSH LVEALALVCG ERGFFYTPKG GGPRRGIVEQ CCTSICSLYQ LENYCNGGGG     60
AGGGGDKTHT CPPCPAPELL GGPSVFLFPP KPKDTLMISR TPEVTCVVVD VSHEDPEVKF    120
NWYVDGVEVH NAKTKPREEQ YNSTYRVVSV LTVLHQDWLN GKEYKCKVSN KALPAPIEKT    180
ISKAKGQPRE PQVYTLPPSR DELTKNQVSL TCLVKGFYPS DIAVEWESNG QPENNYKTTP    240
PVLDSDGSFF LYSKLTVDKS RWQQGNVFSC SVMHEALHNH YTQKSLSLSP G             291

SEQ ID NO: 29           moltype = DNA   length = 933
FEATURE                 Location/Qualifiers
source                  1..933
                        mol_type = other DNA
                        organism = synthetic construct
SEQUENCE: 29
atggaatgga gctgggtctt tctcttcttc ctgtcagtaa cgactggtgt ccactccttc     60
gtgaaccagc acctgtgcgg ctcccacctg gtggaagctc tggctctcgt gtgcggcgag    120
cggggcttct tctacacccc caagggaggc ggtccacgca gaggcatcgt ggaacagtgc    180
tgcacctcca tctgctccct gtaccagctg gaaaactact gcaatggcgg aggtggtgca    240
ggaggcggtg gagacaaaac tcacacatgc ccaccgtgcc cagcacctga actcctgggg    300
ggaccgtcag tcttcctctt ccccccaaaa cccaaggaca cccctcatga tctcccggacc    360
cctgaggtca catgcgtggt ggtggacgtg agccacgaag accctgaggt caagttcaac    420
tggtacgtgg acggcgtgga ggtgcataat gccaagacaa agccgcggga ggagcagtac    480
aacagcacgt accgtgtggt cagcgtcctc accgtcctgc accaggactg gctgaatggc    540
aaggagtaca agtgcaaggt ctccaacaaa gcccccag ccccatcga gaaaaccatc    600
tccaaagcca agggcagcc cgagaacca caggtgtaca ccctgccccc atcccgggat    660
gagctgacca agaaccaggt cagcctgacc tgcctggtca aaggcttcta tcccagcgac    720
atcgccgtgg agtgggagag caatgggcag ccggagaaca actacaagac cacgcctccc    780
gtgctggact ccgacggctc cttcttcctc tacagcaagc tcaccgtgga caagagcagg    840
tggcagcagg gaacgtcttc tcatgctcc gtgatgcatg aggctctgca caaccactac    900
acgcagaaga gcctctccct gtctccgggt tag                                 933

SEQ ID NO: 30           moltype = AA   length = 30
FEATURE                 Location/Qualifiers
source                  1..30
                        mol_type = protein
                        organism = synthetic construct
SEQUENCE: 30
FVNQHLCGSH LVEALALVCG ERGFFYTDPT                                      30

SEQ ID NO: 31           moltype = AA   length = 29
FEATURE                 Location/Qualifiers
source                  1..29
                        mol_type = protein
                        organism = synthetic construct
SEQUENCE: 31
FVNQHLCGSH LVEALALVCG ERGFFYTPK                                       29

SEQ ID NO: 32           moltype = AA   length = 20
FEATURE                 Location/Qualifiers
source                  1..20
                        mol_type = protein
                        organism = synthetic construct
SEQUENCE: 32
GIVEQCCHSI CSLYQLENYC                                                 20

SEQ ID NO: 33           moltype = AA   length = 21
FEATURE                 Location/Qualifiers
source                  1..21
                        mol_type = protein
                        organism = Homo sapiens
SEQUENCE: 33
GIVEQCCTSI CSLYQLENYC N                                               21
```

```
SEQ ID NO: 34            moltype = AA  length = 14
FEATURE                  Location/Qualifiers
source                   1..14
                         mol_type = protein
                         organism = synthetic construct
SEQUENCE: 34
GGGGAGGGGA GGGG                                                           14

SEQ ID NO: 35            moltype = AA  length = 4
FEATURE                  Location/Qualifiers
source                   1..4
                         mol_type = protein
                         organism = synthetic construct
SEQUENCE: 35
GGGG                                                                       4

SEQ ID NO: 36            moltype = AA  length = 57
FEATURE                  Location/Qualifiers
source                   1..57
                         mol_type = protein
                         organism = synthetic construct
SEQUENCE: 36
FVNQHLCGSH LVEALELVCG ERGFHYGGGG GGSGGGGGIV EQCCTSTCSL DQLENYC             57

SEQ ID NO: 37            moltype = AA  length = 56
FEATURE                  Location/Qualifiers
source                   1..56
                         mol_type = protein
                         organism = synthetic construct
SEQUENCE: 37
FVNQHLCGSD LVEALALVCG ERGFFYTDPT GGGPRRGIVE QCCHSICSLY QLENYC              56

SEQ ID NO: 38            moltype = AA  length = 57
FEATURE                  Location/Qualifiers
source                   1..57
                         mol_type = protein
                         organism = synthetic construct
SEQUENCE: 38
FVNQHLCGSH LVEALALVCG ERGFFYTDPT GGGPRRGIVE QCCHSICSLY QLENYCN             57

SEQ ID NO: 39            moltype = AA  length = 56
FEATURE                  Location/Qualifiers
source                   1..56
                         mol_type = protein
                         organism = synthetic construct
SEQUENCE: 39
FVNQHLCGSH LVEALALVCG ERGFFYTPKG GGPRRGIVEQ CCTSICSLYQ LENYCN              56

SEQ ID NO: 40            moltype = AA  length = 86
FEATURE                  Location/Qualifiers
source                   1..86
                         mol_type = protein
                         organism = Homo sapiens
SEQUENCE: 40
FVNQHLCGSH LVEALYLVCG ERGFFYTPKT RREAEDLQVG QVELGGGPGA GSLQPLALEG          60
SLQKRGIVEQ CCTSICSLYQ LENYCN                                               86

SEQ ID NO: 41            moltype = AA  length = 30
FEATURE                  Location/Qualifiers
source                   1..30
                         mol_type = protein
                         organism = Homo sapiens
SEQUENCE: 41
FVNQHLCGSH LVEALYLVCG ERGFFYTPKT                                           30
```

We claim:

1. A method of downregulating insulin receptor or insulin-like growth factor 1 receptor (IGF1R), and/or decreasing phosphorylated Akt in a cancer cell, said method comprising administering an effective amount of fusion protein comprising an insulin polypeptide and an Fc fragment, wherein the insulin polypeptide comprises the amino acid sequence:

```
                                        (SEQ ID NO: 6)
FVNQHLCGSDLVEALALVCGERGFFYTDPTGG

GPRRGIVEQCCHSICSLYQLENYCN
``` or the amino acid sequence:

```
                                       (SEQ ID NO: 37)
FVNQHLCGSDLVEALALVCGERGFFYTDPTGG

GPRRGIVEQCCHSICSLYQLENYC
``` to a mammal in need thereof, and wherein the ratio of IC50 for the fusion protein to IC50 for recombinant human insulin (RHI) is less than or equal to 20, wherein said fusion protein exhibits an anti-tumor effect on said cancer cell in said mammal after said administering, said anti-tumor effect being selected from the group consisting of downregulation of insulin receptor, downregulation of insulin-like growth factor 1 receptor (IGF1R), decreased phosphorylated Akt, and a combination thereof, as compared to an untreated control cancer cell.

2. The method of claim 1, wherein said fusion protein inhibits tumor growth in said mammal after said administration.

3. The method of claim 1, wherein said mammal has a reduction in tumor volume of at least 30% after said administration as compared to an untreated control.

4. The method of claim 1, wherein said fusion protein is administered via a route of administration selected from the group consisting of intravenous, subcutaneous, and intratumoral injection.

5. The method of claim 1, wherein said fusion protein is co-administered with a primary or secondary cancer therapy selected from the group consisting of chemotherapy agents, tamoxifen agonists, or antibodies against the IGF1 receptor.

6. The method of claim 1, wherein said mammal has been diagnosed with a cancer selected from the group consisting of breast cancer, colorectal cancer, and melanoma.

7. The method of claim 1, wherein the Fc fragment of the fusion protein comprises the sequence:

```
                                       (SEQ ID NO: 15)
DKTHTCPPCPAPELLGGPSVFLFPPKPKDTLM

ISRTPEVTCVVVDVSHEDPEVKFNWYVDGVEV

HNAKTKPREEQYNSTYRVVSVLTVLHQDWLNG

KEYKCKVSNKALPAPIEKTISKAKGQPREPQV

YTLPPSRDELTKNQVSLTCLVKGFYPSDIAVE
```

```
-continued
WESNGQPENNYKTTPPVLDSDGSFFLYSKLTV

DKSRWQQGNVFSCSVMHEALHNHYTQKSLSLS.

PG
```

8. The method of claim 1, wherein the insulin polypeptide and the Fc fragment are connected by a linker, wherein the linker comprises the sequence:

```
                                       (SEQ ID NO: 13)
             GGGGAGGGG;
``` or the sequence:

```
                                       (SEQ ID NO: 34)
             GGGGAGGGGAGGGG;
``` or the sequence:

```
                                       (SEQ ID NO: 35)
        GGGG
```

9. The method of claim 1, wherein the fusion protein comprises the sequence:

```
                                        (SEQ ID NO: 1)
FVNQHLCGSDLVEALALVCGERGFFYTDPTGG

GPRRGIVEQCCHSICSLYQLENYCNGGGGAGG

GGDKTHTCPPCPAPELLGGPSVFLFPPKPKDT

LMISRTPEVTCVVVDVSHEDPEVKFNWYVDGV

EVHNAKTKPREEQYNSTYRVVSVLTVLHQDWL

NGKEYKCKVSNKALPAPIEKTISKAKGQPREP

QVYTLPPSRDELTKNQVSLTCLVKGFYPSDIA

VEWESNGQPENNYKTTPPVLDSDGSFFLYSKL

TVDKSRWQQGNVFSCSVMHEALHNHYTQKSLS

LSPG.
```

10. The method of claim 1, wherein the fusion protein is a homodimer.

11. The method of claim 1, wherein the fusion protein comprises domains in the following orientation from N- to C-termini: (N-terminus)—insulin polypeptide—linker—Fc fragment—(C-terminus), and wherein the insulin polypeptide comprises domains in the following orientation from N- to C-termini: (N-terminus)—B-chain—C-peptide—A-chain—(C-terminus).

12. The method of claim 1, wherein the duration of activity of the fusion protein is longer than about 1 day.

13. The method of claim 1, wherein a pharmaceutical composition is administered to said mammal, wherein said composition comprises the effective amount of said fusion protein dispersed in a pharmaceutically acceptable carrier.

* * * * *